United States Patent
Kori et al.

(10) Patent No.: US 12,379,662 B2
(45) Date of Patent: *Aug. 5, 2025

(54) MATERIAL FOR FORMING ORGANIC FILM, PATTERNING PROCESS, COMPOUND, AND POLYMER

(71) Applicant: SHIN-ETSU CHEMICAL CO., LTD., Tokyo (JP)

(72) Inventors: Daisuke Kori, Joetsu (JP); Seiichiro Tachibana, Joetsu (JP); Shiori Nonaka, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 726 days.

This patent is subject to a terminal disclaimer.

(21) Appl. No.: 17/549,965

(22) Filed: Dec. 14, 2021

(65) Prior Publication Data

US 2022/0214617 A1    Jul. 7, 2022

(30) Foreign Application Priority Data

Dec. 25, 2020  (JP) ................. 2020-216966

(51) Int. Cl.
   *G03F 7/11* (2006.01)
   *C07D 519/00* (2006.01)
   (Continued)

(52) U.S. Cl.
   CPC ............. *G03F 7/11* (2013.01); *C07D 519/00* (2013.01); *C08F 34/02* (2013.01); *G03F 7/0045* (2013.01);
   (Continued)

(58) Field of Classification Search
   CPC .......... G03F 7/11; G03F 7/0045; G03F 7/162; C07D 519/00; C08F 34/02
   See application file for complete search history.

(56) References Cited

U.S. PATENT DOCUMENTS

2002/0106909 A1   8/2002  Kato et al.
2003/0036579 A1   2/2003  Momoda et al.
(Continued)

FOREIGN PATENT DOCUMENTS

CN      110546570 A      12/2019
EP       1 293 522 A1     3/2003
(Continued)

OTHER PUBLICATIONS

Hosseinzadeh, Convenient Synthesis of Naphthopyrans using Montmorillonite K-10 as heterogeneous catalyst, J Chem Sci vol. 126, 2014, 1081-1089. (Year: 2014).*

(Continued)

*Primary Examiner* — Mark F. Huff
*Assistant Examiner* — Kevin J Drummey
(74) *Attorney, Agent, or Firm* — Oliff PLC

(57) ABSTRACT

A material for forming organic film contains (A) compound shown by general formula (1) and/or polymer having repeating unit shown by general formula (4), and (B) organic solvent. In formula (1), AR1, AR2, AR3, AR4, AR5, and AR6 each represent benzene ring or naphthalene ring; R1 represents any group shown in following formula (2); "n" represents integer of 1 or 2; and W represents divalent organic group having 2-50 carbon atoms. In formula (4), AR1, AR2, AR3, AR4, AR5, AR6, R1, "n", and W are as defined above; and R2 and R3 each represent hydrogen atom or organic group having 1-20 carbon atoms, and optionally bond to each other within molecule to form cyclic organic group. An object provides a material for forming organic film to enable high etching resistance and excellent twisting resistance without impairing resin-derived carbon content; and compound and polymer suitable for material for forming organic film.

(Continued)

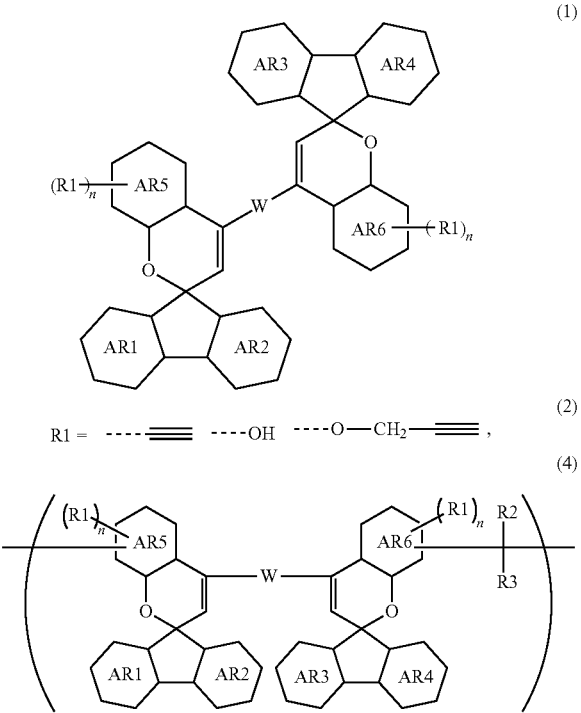

| | | |
|---|---|---|
| 2006/0204891 A1 | 9/2006 | Hatakeyama |
| 2007/0051922 A1 | 3/2007 | Nakatani et al. |
| 2009/0274978 A1 | 11/2009 | Ohashi et al. |
| 2010/0099044 A1 | 4/2010 | Hatakeyama et al. |
| 2013/0302990 A1 | 11/2013 | Watanabe et al. |
| 2014/0246400 A1 | 9/2014 | Higashihara et al. |
| 2019/0094695 A1 | 3/2019 | Nosaka et al. |
| 2019/0300498 A1 | 10/2019 | Tachibana et al. |
| 2020/0356007 A1 | 11/2020 | Kori et al. |
| 2020/0379350 A1 | 12/2020 | Tokunaga et al. |

FOREIGN PATENT DOCUMENTS

| | | |
|---|---|---|
| EP | 3 550 362 A1 | 10/2019 |
| EP | 3 739 387 A1 | 11/2020 |
| JP | H06-118651 A | 4/1994 |
| JP | 2002-334869 A | 11/2002 |
| JP | 2004-205685 A | 7/2004 |
| JP | 2005-128509 A | 5/2005 |
| JP | 2005-250434 A | 9/2005 |
| JP | 2006-227391 A | 8/2006 |
| JP | 2006-285095 A | 10/2006 |
| JP | 2006-293298 A | 10/2006 |
| JP | 2007-199653 A | 8/2007 |
| JP | 2008-158002 A | 7/2008 |
| JP | 2009-269953 A | 11/2009 |
| JP | 2010-122656 A | 6/2010 |
| JP | 2013-253227 A | 12/2013 |
| KR | 10-2019-0114839 A | 10/2019 |
| WO | 2004/066377 A1 | 8/2004 |
| WO | 2013/047106 A1 | 4/2013 |
| WO | 2017/208796 A1 | 12/2017 |

OTHER PUBLICATIONS

Yaws, Handbook of Thermodynamic Properties, Physical Properties and Refractive Index. Retrieved from https://app.knovel.com/hotlink/itble/rcid:kpYHTPPCC4/id:kt002UT9Q2/yaws-handbook-thermodynamic/physical-properties-refractive (Year: 2024).*

Oct. 26, 2023 Office Action issued in Korean Patent Application No. 10-2021-0184057.

May 31, 2022 Extended Search Report issued in European Patent Application No. 21214843.1.

May 20, 2022 Extended Search Report issued in European Patent Application No. 21214858.9.

Russo et al., "Organic conducting polymers: synthesis, characterization and conductivity of polyethynylfluorenol", Polymer, vol. 33, No. 20, pp. 4401-4409, 1992.

U.S. Appl. No. 17/549,987, filed Dec. 14, 2021 in the name of Daisuke Kori et al.

Nov. 13, 2024 Office Action and Search Report issued in Chinese Patent Application No. 202111588128.0.

\* cited by examiner

20 Claims, 1 Drawing Sheet

(51) Int. Cl.
  C08F 34/02   (2006.01)
  G03F 7/004   (2006.01)
  G03F 7/16    (2006.01)
  G03F 7/20    (2006.01)
  G03F 7/34    (2006.01)
  G03F 7/38    (2006.01)
  G03F 7/40    (2006.01)

(52) U.S. Cl.
  CPC .............. *G03F 7/162* (2013.01); *G03F 7/343* (2013.01); *G03F 7/346* (2013.01); *G03F 7/38* (2013.01); *G03F 7/40* (2013.01)

(56) References Cited

U.S. PATENT DOCUMENTS

| | | |
|---|---|---|
| 2005/0255712 A1 | 11/2005 | Kato et al. |
| 2006/0019195 A1 | 1/2006 | Hatakeyama et al. |

[FIG. 1]
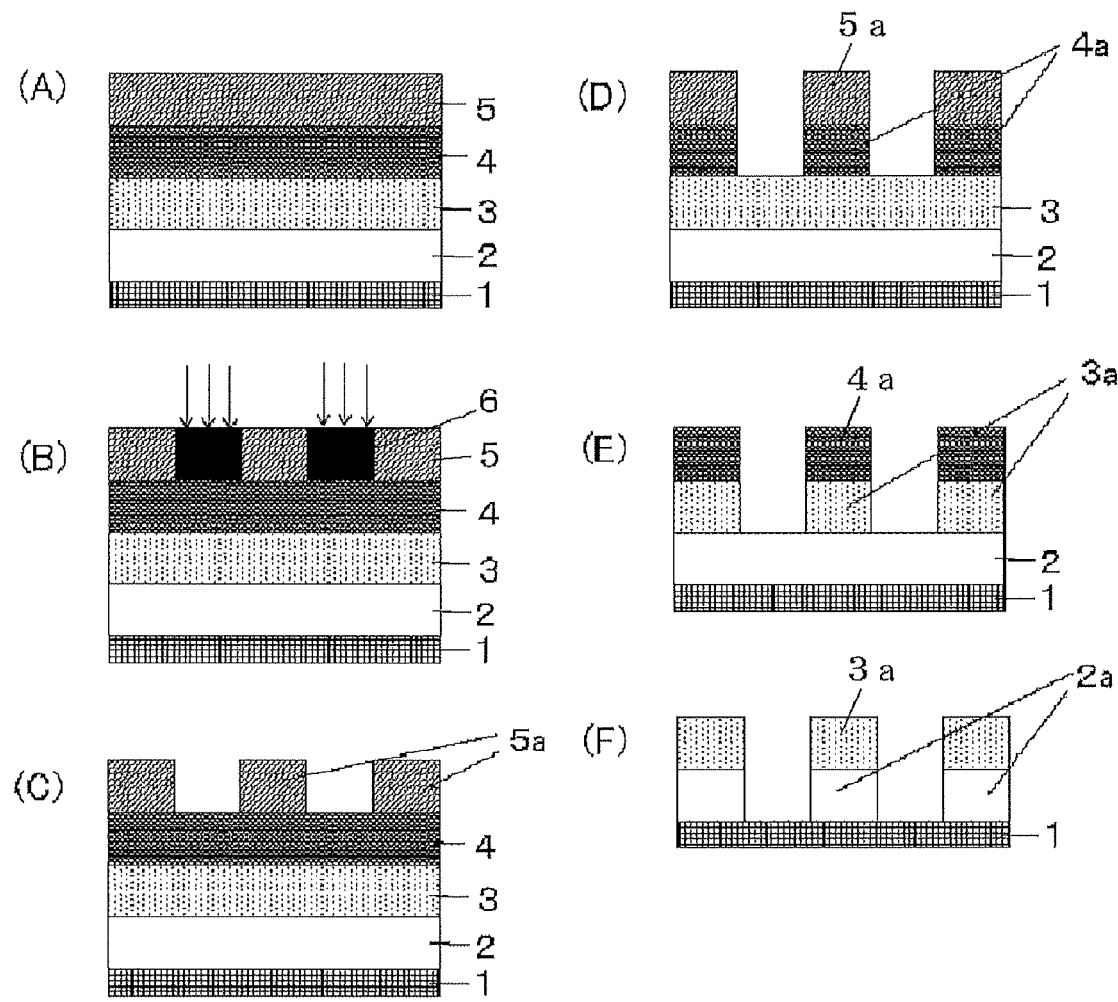
[FIG. 2]
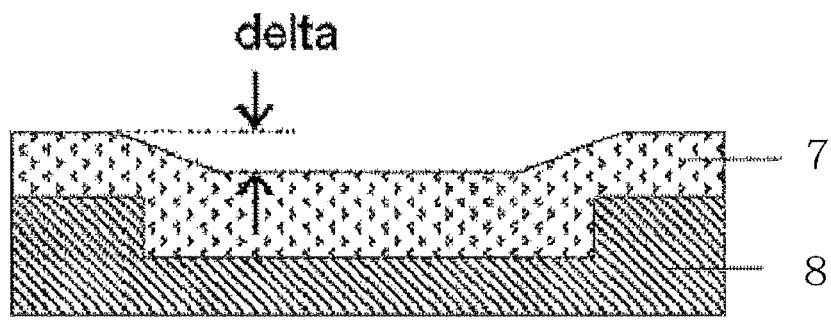

MATERIAL FOR FORMING ORGANIC FILM, PATTERNING PROCESS, COMPOUND, AND POLYMER

TECHNICAL FIELD

The present invention relates to: a coating-type material for forming an organic film employed in fine patterning in processes of manufacturing semiconductor devices and the like; and a patterning process which uses this material and is suitable for exposure with deep ultraviolet ray, KrF excimer laser beam (248 nm), ArF excimer laser beam (193 nm), $F_2$ laser beam (157 nm), $Kr_2$ laser beam (146 nm), $Ar_2$ laser beam (126 nm), extreme ultraviolet ray (EUV, 13.5 nm), electron beam (EB), and X-ray.

BACKGROUND ART

Recently, along with advancements toward higher integration and higher processing speed of semiconductor devices, a finer pattern rule has been required. In this situation, various techniques have been developed in regard to how patterning process can be performed more finely and precisely depending on light sources used in lithography with light exposure, which is a commonly-employed technique at present.

As the light source for lithography employed in resist pattern formation, light exposure using a g-line (436 nm) or an i-line (365 nm) of a mercury lamp as the light source is widely adopted for portions where the degree of integration is low. Meanwhile, for portions where the degree of integration is high and finer patterning is required, lithography using a KrF excimer laser (248 nm) or an ArF excimer laser (193 nm) with shorter wavelengths has also been practically used. Moreover, for the most-advanced generation requiring further finer patterning, lithography with extreme ultraviolet ray (EUV, 13.5 nm) is about to be put into practical use.

It is well known that in a monolayer resist method, which is typically employed as a resist patterning process, as the thinning of resist patterns progresses as described above, the ratio of a pattern height to a pattern line width (aspect ratio) is increased, and pattern collapse occurs due to the surface tension of a developer during development. In this situation, it is known that a multilayer resist method, in which a pattern is formed by laminating films having different dry etching properties, is excellent in forming a pattern with a high aspect ratio on an uneven substrate. There have been developed: a two-layer resist method in which a photoresist layer made of a silicon-containing photosensitive polymer is combined with an underlayer made of an organic polymer containing carbon, hydrogen, and oxygen as main constituent elements, for example, a novolak polymer (Patent Document 1 etc.); and a three-layer resist method in which a photoresist layer made of an organic photosensitive polymer used in a monolayer resist method is combined with an underlayer made of a silicon-based polymer or a silicon-based CVD film, and with an organic layer made of an organic polymer (Patent Document 2 etc.).

In this three-layer resist method, first, a fluorocarbon-based dry etching gas is used to transfer the pattern of the photoresist layer to the silicon-containing underlayer. Then, using the pattern as a mask, dry etching with an oxygen-containing gas is performed to transfer the pattern to the organic film containing carbon and hydrogen as main constituent elements. Further, by dry etching using the resultant as a mask, the pattern is formed on a substrate to be processed. However, in semiconductor device manufacturing processes after the 20-nm generation, when the pattern is transferred to a substrate to be processed by dry etching using such an organic film pattern as a hard mask, phenomena are observed in which the organic film pattern is twisted and/or curved.

The carbon hard mask formed immediately above the substrate to be processed is generally an amorphous carbon (hereinafter CVD-C) film prepared by a CVD method using a methane gas, an ethane gas, an acetylene gas, or the like as raw materials. It is known that the amount of hydrogen atoms in the CVD-C film can be reduced quite small, and the CVD-C film is very effective against the twisting and curving of the pattern as described above. Nevertheless, it is also known that when the substrate to be processed used as a base has a step, it is difficult to fill such a step into a flat state due to the characteristics of the CVD process. As a result, when a substrate to be processed having a step is coated with a CVD-C film and then patterned with a photoresist, the step of the substrate to be processed causes the applied surface of the photoresist to have a step. This makes the photoresist film thickness non-uniform, and consequently the focus margin and the pattern profile degraded during lithography.

On the other hand, it is known that when an organic film serving as the carbon hard mask formed immediately above the substrate to be processed is formed by a spin coating method, there is an advantage that a step(s) of the uneven substrate can be filled into a flat state. Planarizing the substrate by using the organic film material reduces fluctuations in film thicknesses of a silicon-containing underlayer and a photoresist coated on the organic film, can increase the focus margin in lithography, and can form a correct pattern.

Hence, there are demands for: an organic film material which allows formation of an organic film by a spin coating method, the organic film enabling formation of a film having high etching resistance in dry etching a substrate to be processed and high planarizing property on the substrate to be processed; and a method for forming such an organic film.

Conventionally, condensed resins using aromatic alcohols and carbonyl compounds such as ketones and aldehydes as condensing agents for a phenol compound or naphthol compound have been known as the material for forming an organic film such as an organic film material described above in multilayer resist methods. Examples of such condensed resins include a fluorene bisphenol novolak resin described in Patent Document 2, a bisphenol compound and a novolak resin thereof described in Patent Document 3, a novolak resin of an adamantane phenol compound described in Patent Document 4, a bisnaphthol compound and a novolak resin thereof described in Patent Document 5, etc. The main skeletons of the resins used in these materials are constituted of naphthalene, fluorene, adamantane, or the like, each of which has high carbon density. However, their etching resistance is inevitably degraded due to an oxygen atom of the phenolic hydroxyl group.

Further, to prevent the etching resistance degradation, no heteroatom such as oxygen is incorporated into a resin for organic film material. As an example of such a resin, Patent Document 6 describes a resin having a fluorene structure. Nevertheless, a crosslinking agent, such as a methylol compound, is added to the composition, which is used to form a cured film. For this reason, even if the carbon content of the resin is increased, this increase is offset by the low carbon content of the crosslinking agent, resulting in the problem of etching resistance degradation.

Moreover, as an organic film material for improving etching resistance, an organic film material having a benzopyran structure introduced therein has been studied as disclosed in Patent Document 7. However, various properties such as heat resistance and etching resistance demanded for organic film materials need to be improved. Additionally, substrates to be processed have complex profiles, and various types of materials are used as substrates to be processed, too. An organic film material excellent in process margin is demanded.

CITATION LIST

Patent Literature

Patent Document 1: JP H6-118651 A
Patent Document 2: JP 2005-128509 A
Patent Document 3: JP 2006-293298 A
Patent Document 4: JP 2006-285095 A
Patent Document 5: JP 2010-122656 A
Patent Document 6: WO 2013-047106 A1
Patent Document 7: WO 2017-208796 A1

SUMMARY OF INVENTION

Technical Problem

The present invention has been made in view of the above-described circumstances. An object of the present invention is to provide: a material for forming an organic film, the material enabling high etching resistance and excellent twisting resistance without impairing resin-derived carbon content; a patterning process using this material; and a compound and a polymer suitable for such a material for forming an organic film.

Solution to Problem

To achieve the object, the present invention provides a material for forming an organic film, comprising:
(A) a compound shown by the following general formula (1) and/or a polymer comprising a repeating unit shown by the following general formula (4); and
(B) an organic solvent,

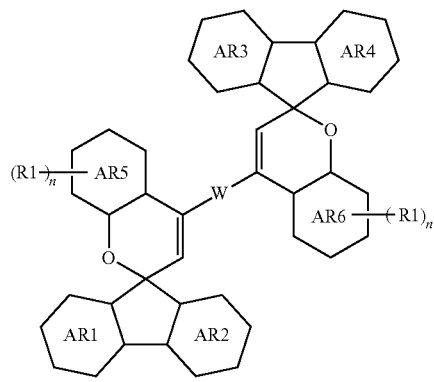

(1)

wherein AR1, AR2, AR3, AR4, AR5, and AR6 each represent a benzene ring or a naphthalene ring; R1 represents any group shown in the following formula (2); "n" represents an integer of 1 or 2; and W represents a divalent organic group having 2 to 50 carbon atoms,

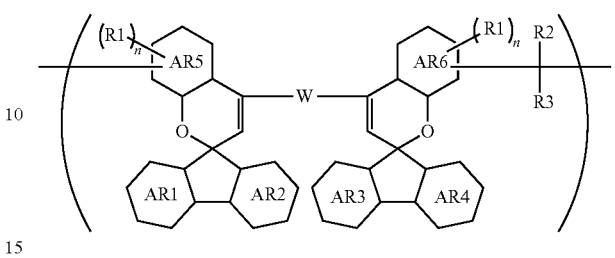

wherein AR1, AR2, AR3, AR4, AR5, AR6, R1, "n", and W are as defined above; and R2 and R3 each represent a hydrogen atom or an organic group having 1 to 20 carbon atoms, and optionally bond to each other within a molecule to form a cyclic organic group.

The main skeleton of the compound shown by the general formula (1) according to the present invention is formed to have a structure containing many condensed aromatic ring structures with high carbon content. Further, the crosslinking reaction of the benzopyran ring structure successfully results in formation of a fine organic film with high carbon density. Accordingly, the inventive material for forming an organic film using the compound is useful when used as an organic film material and capable of forming an organic film having high twisting resistance (curving resistance) and also high dry etching resistance. Moreover, the use of the polymer having a repeating unit as shown by the general formula (4) makes it possible to form a fine organic film by increasing the curability without etching resistance degradation. Further, the material for forming an organic film is capable of forming a film regardless of the material and profile of a substrate. Furthermore, a mixture of the compound of the general formula (1) and the polymer having a repeating unit shown by the general formula (4) allows adjustment of various properties within appropriate ranges, which are required for organic film usages, such as filling property, planarizing property, and outgassing property against sublimation product.

The compound is preferably a compound shown by the following general formula (3),

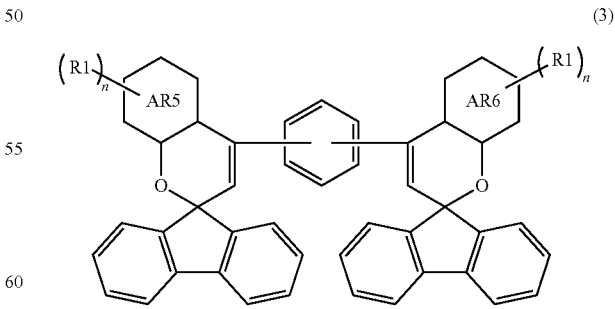

(3)

wherein AR5, AR6, R1, and "n" are as defined above.

Introducing such a structure makes it possible to further enhance the etching resistance and twisting resistance.

The polymer is preferably a polymer comprising a repeating unit shown by the following general formula (5), $$\left(\begin{array}{c}(R1)_n \\ AR5 \\ O \end{array}\middle|\begin{array}{c}(R1)_n \\ AR6 \\ O \end{array}\middle|\begin{array}{c}R2 \\ R3\end{array}\right) \quad (5)$$

wherein AR5, AR6, R1, R2, R3, and "n" are as defined above.

The use of the polymer having such a repeating unit makes it possible to improve the handleability, such as solubility into the organic solvent.

Further preferably, the polymer has a weight-average molecular weight of 1000 to 10000.

When the material for forming an organic film contains the polymer having a weight-average molecular weight within such a range, outgassing can be suppressed during baking without impairing the solubility into the organic solvent.

Additionally, the organic solvent is preferably a mixture of one or more organic solvents each having a boiling point of lower than 180° C. and one or more organic solvents each having a boiling point of 180° C. or higher.

When the organic solvent is a mixture as described above, the addition of the high-boiling-point solvent(s) to the compound and/or the polymer imparts thermal flowability to the organic film. Accordingly, the material for forming an organic film has both high filling and planarizing properties.

The inventive material for forming an organic film preferably further comprises one or more of (C) an acid generator, (D) a surfactant, (E) a crosslinking agent, and (F) a plasticizer.

Incorporating the additive(s) makes the material for forming an organic film more excellent in coatability, filling property, and planarizing property.

The present invention provides a patterning process for forming a pattern in a substrate to be processed, comprising:

forming an organic film by using the above-described material for forming an organic film on a substrate to be processed;

forming a silicon-containing resist underlayer film by using a silicon-containing resist underlayer film material on the organic film;

forming a resist upper layer film by using a photoresist composition on the silicon-containing resist underlayer film;

forming a circuit pattern in the resist upper layer film;

transferring the pattern to the silicon-containing resist underlayer film by etching while using the resist upper layer film having the formed pattern as a mask;

transferring the pattern to the organic film by etching while using the silicon-containing resist underlayer film having the transferred pattern as a mask; and further forming the pattern in the substrate to be processed by etching while using the organic film having the transferred pattern as a mask.

The patterning process according to this three-layer resist process makes it possible to precisely form a fine pattern in a substrate to be processed.

Moreover, the present invention provides a patterning process for forming a pattern in a substrate to be processed, comprising:

forming an organic film by using the above-described material for forming an organic film on a substrate to be processed;

forming a silicon-containing resist underlayer film by using a silicon-containing resist underlayer film material on the organic film;

forming an organic antireflective coating film on the silicon-containing resist underlayer film;

forming a resist upper layer film by using a photoresist composition on the organic antireflective coating film, so that a 4-layered film structure is constructed;

forming a circuit pattern in the resist upper layer film;

transferring the pattern to the organic antireflective coating film and the silicon-containing resist underlayer film by etching while using the resist upper layer film having the formed pattern as a mask;

transferring the pattern to the organic film by etching while using the silicon-containing resist underlayer film having the transferred pattern as a mask; and further forming the pattern in the substrate to be processed by etching the substrate to be processed while using the organic film having the transferred pattern as a mask.

The patterning process according to this four-layer resist process makes it possible to further precisely form a fine pattern in a substrate to be processed.

Further, the present invention provides a patterning process for forming a pattern in a substrate to be processed, including:

forming an organic film by using the above-described material for forming an organic film on a substrate to be processed;

forming an inorganic hard mask selected from a silicon oxide film, a silicon nitride film, and a silicon oxynitride film on the organic film;

forming a resist upper layer film by using a photoresist composition on the inorganic hard mask;

forming a circuit pattern in the resist upper layer film;

transferring the pattern to the inorganic hard mask by etching while using the resist upper layer film having the formed pattern as a mask;

transferring the pattern to the organic film by etching while using the inorganic hard mask having the transferred pattern as a mask; and further forming the pattern in the substrate to be processed by etching the substrate to be processed while using the organic film having the transferred pattern as a mask.

The patterning process according to such a three-layer resist process makes it possible to precisely form a fine pattern in a substrate to be processed.

Furthermore, the present invention provides a patterning process for forming a pattern in a substrate to be processed, comprising:

forming an organic film by using the above-described material for forming an organic film on a substrate to be processed;

forming an inorganic hard mask selected from a silicon oxide film, a silicon nitride film, and a silicon oxynitride film on the organic film;

forming an organic antireflective coating film on the inorganic hard mask;

forming a resist upper layer film by using a photoresist composition on the organic antireflective coating film, so that a 4-layered film structure is constructed;

forming a circuit pattern in the resist upper layer film;

transferring the pattern to the organic antireflective coating film and the inorganic hard mask by etching while using the resist upper layer film having the formed pattern as a mask;

transferring the pattern to the organic film by etching while using the inorganic hard mask having the transferred pattern as a mask; and further forming the pattern in the substrate to be processed by etching the substrate to be processed while using the organic film having the transferred pattern as a mask.

The patterning process according to such a four-layer resist process makes it possible to more precisely form a fine pattern in a substrate to be processed.

In these cases, the inorganic hard mask is preferably formed by a CVD method or an ALD method.

When the inorganic hard mask is formed by a CVD method or an ALD method, a fine pattern can be more precisely formed in a substrate to be processed.

The pattern is preferably formed in the resist upper layer film by a method of a photolithography with a wavelength of 10 nm or more and 300 nm or less, a direct drawing with electron beam, nanoimprinting, or a combination thereof.

By employing the aforementioned methods as a method for forming a circuit pattern in the resist upper layer film, a fine pattern can be more precisely formed in a substrate to be processed.

Preferably, alkaline development or organic solvent development is employed as a development method in the patterning processes.

When the development method is performed using an alkali or organic solvent, it is possible to more precisely form a fine pattern in a substrate to be processed.

The substrate to be processed is preferably a semiconductor device substrate, a metal film, a metal carbide film, a metal oxide film, a metal nitride film, a metal oxycarbide film, or a metal oxynitride film.

In the present invention, the aforementioned substrates to be processed are usable, for example.

The metal is preferably silicon, titanium, tungsten, hafnium, zirconium, chromium, germanium, cobalt, copper, silver, gold, aluminum, indium, gallium, arsenic, palladium, iron, tantalum, iridium, manganese, molybdenum, ruthenium, or an alloy thereof.

These are usable as the metal. As described above, when the inventive material for forming an organic film is used for patterning, it is possible to precisely transfer and form a pattern of an upper layer photoresist into a substrate to be processed.

The present invention provides a compound shown by the following general formula (1),

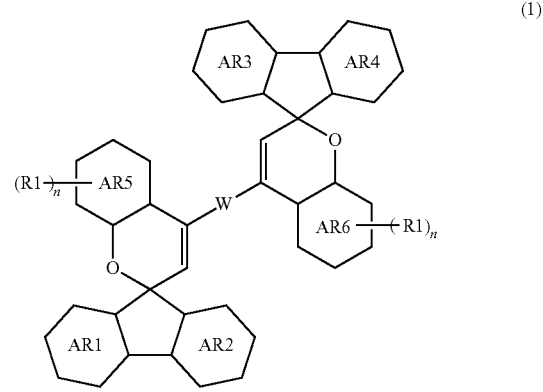

wherein AR1, AR2, AR3, AR4, AR5, and AR6 each represent a benzene ring or a naphthalene ring; R1 represents any group shown in the following formula (2); "n" represents an integer of 1 or 2; and W represents a divalent organic group having 2 to 50 carbon atoms,

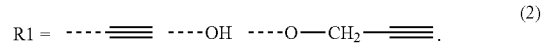

The compound shown by the general formula (1) contains many condensed aromatic ring structures and condensed ring structures. Thus, the compound serves as a material enabling formation of an organic film that is excellent in heat resistance, twisting resistance, and dry etching resistance.

Preferably, the compound is shown by the following general formula (3),

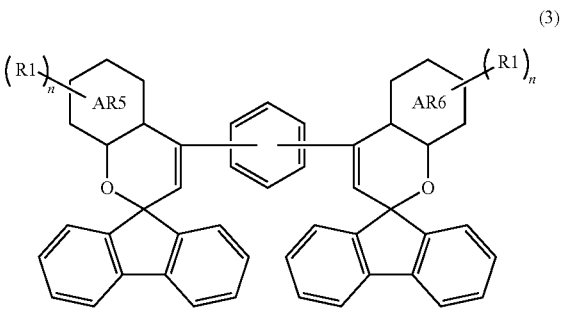

wherein AR5, AR6, R1, and "n" are as defined above.

The use of such a compound enables further enhancements of the etching resistance and twisting resistance.

Moreover, the present invention provides a polymer comprising a repeating unit shown by the following general formula (4),

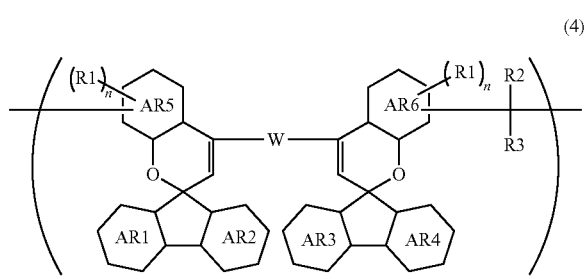

(4)

wherein AR1, AR2, AR3, AR4, AR5, and AR6 each represent a benzene ring or a naphthalene ring; R1 represents any group shown in the following formula (2); "n" represents an integer of 1 or 2; W represents a divalent organic group having 2 to 50 carbon atoms; and R2 and R3 each represent a hydrogen atom or an organic group having 1 to 20 carbon atoms, and optionally bond to each other within a molecule to form a cyclic organic group,

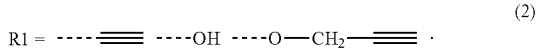

(2)

Since multiple cardo structures are incorporated in such a repeating unit, the use of the polymer in a material for forming an organic film makes it possible to achieve all of properties such as etching resistance, heat resistance, filling property, planarizing property, solvent solubility, and film formability, which are otherwise in trade-off relationships.

The polymer preferably comprises a repeating unit shown by the following general formula (5),

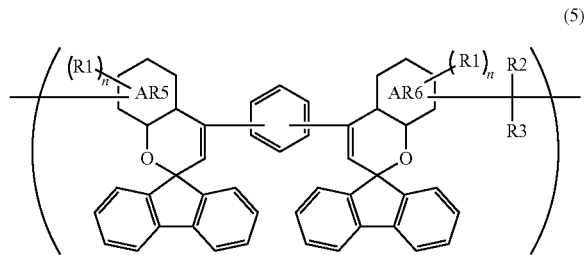

(5)

wherein AR5, AR6, R1, R2, R3, and "n" are as defined above.

Having such a repeating unit increases the carbon density, and the polymer serves as a material for forming an organic film that is excellent in etching resistance and twisting resistance.

Advantageous Effects of Invention

As described above, since the main skeleton of either the inventive compound or polymer is constituted of a structure containing many condensed aromatic rings, these are useful for forming an organic film excellent in etching resistance and twisting resistance. Moreover, the material for forming an organic film containing this compound or polymer is a useful material for forming an organic film having excellent etching resistance and twisting resistance as well as various properties such as heat resistance, filling property, and planarizing property. Thus, the material for forming an organic film is quite useful in multilayer resist processes, for example, a two-layer resist process, a three-layer resist process using a silicon-containing resist underlayer film, or a four-layer resist process using a silicon-containing resist underlayer film and an organic antireflective coating film. Additionally, the inventive patterning processes make it possible to precisely form a fine pattern in a substrate to be processed in such multilayer resist processes.

BRIEF DESCRIPTION OF DRAWINGS

FIG. 1 is an explanatory diagram illustrating an example of an inventive patterning process according to a three-layer resist process; and FIG. 2 is an explanatory diagram illustrating a method for evaluating planarizing property in Examples.

DESCRIPTION OF EMBODIMENTS

There have been demands for: a material for forming an organic film, the material enabling high etching resistance and excellent twisting resistance without impairing the resin-derived carbon content; a patterning process using the material; and a compound and a polymer suitable for such a material for forming an organic film.

The present inventors have found that a compound and a polymer according to the present invention each having the main skeleton constituted of a structure containing many condensed aromatic rings are useful compound and polymer for forming an organic film excellent in etching resistance and twisting resistance. This finding has led to the completion of the present invention.

Specifically, the present invention is a material for forming an organic film, comprising:

(A) a compound shown by the following general formula (1) and/or a polymer comprising a repeating unit shown by the following general formula (4); and (B) an organic solvent,

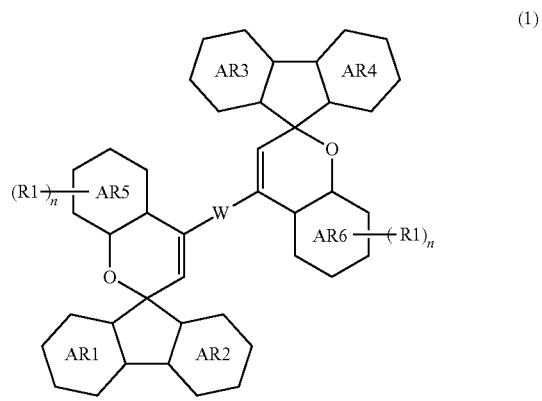

(1)

wherein AR1, AR2, AR3, AR4, AR5, and AR6 each represent a benzene ring or a naphthalene ring; R1 represents any group shown in the following formula (2); "n" represents an integer of 1 or 2; and W represents a divalent organic group having 2 to 50 carbon atoms,

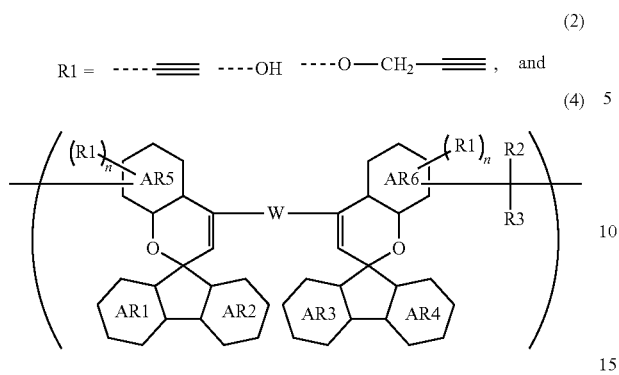

wherein AR1, AR2, AR3, AR4, AR5, AR6, R1, "n", and W are as defined above; and R2 and R3 each represent a hydrogen atom or an organic group having 1 to 20 carbon atoms, and optionally bond to each other within a molecule to form a cyclic organic group.

Hereinafter, embodiments of the present invention will be described, but the present invention is not limited to the following.

<Compound used in Material for Forming Organic Film>

A compound used in the inventive material for forming an organic film is a compound shown by the following general formula (1).

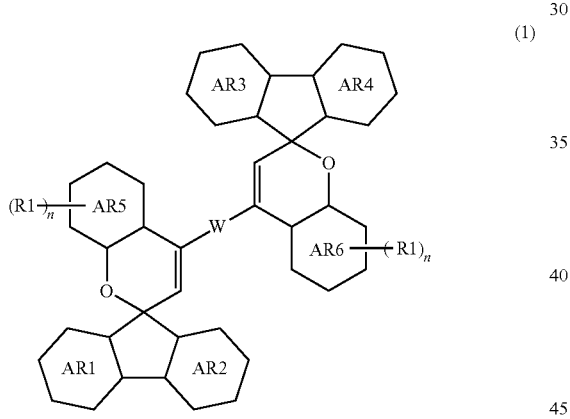

In the general formula (1), AR1, AR2, AR3, AR4, AR5, and AR6 each represent a benzene ring or a naphthalene ring. R1 represents any group shown in the following formula (2). "n" represents an integer of 1 or 2. W represents a divalent organic group having 2 to 50 carbon atoms.

$$R1 = \text{----}\!\!\equiv\quad \text{----OH}\quad \text{----O---CH}_2\text{---}\!\!\equiv \tag{2}$$

In the general formula (1), W is a divalent organic group having 2 to 50 carbon atoms. Specific examples thereof include structures shown below etc.

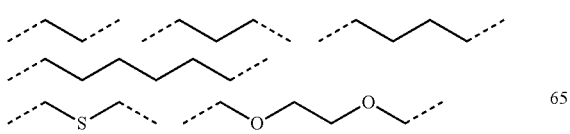

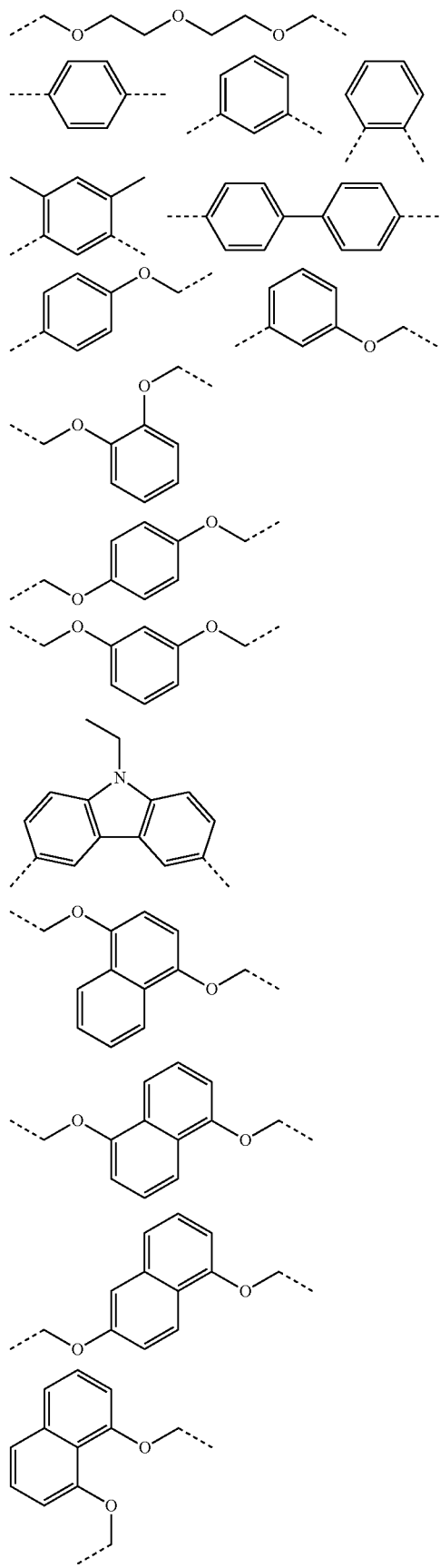

13

-continued

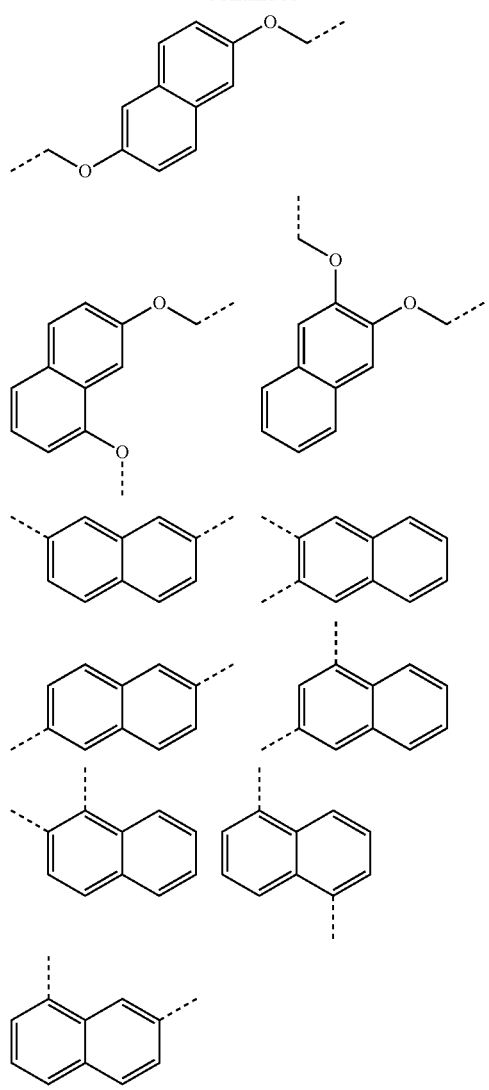

Broken lines represent bonding arms.

Examples of fluorene-based partial structures including AR1 and AR2 or AR3 and AR4 in the general formula (1) include the following etc. Among these, fluorene having benzene rings at AR1, AR2, AR3, and AR4 is particularly preferable.

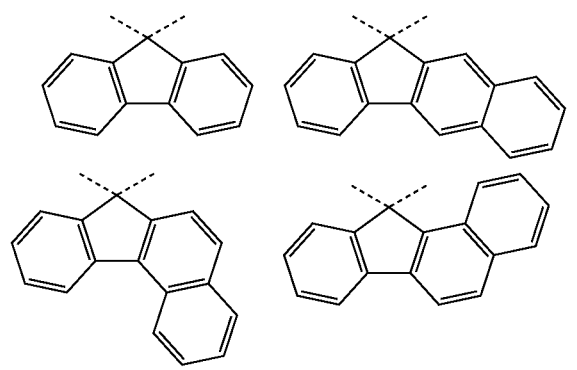

14

-continued

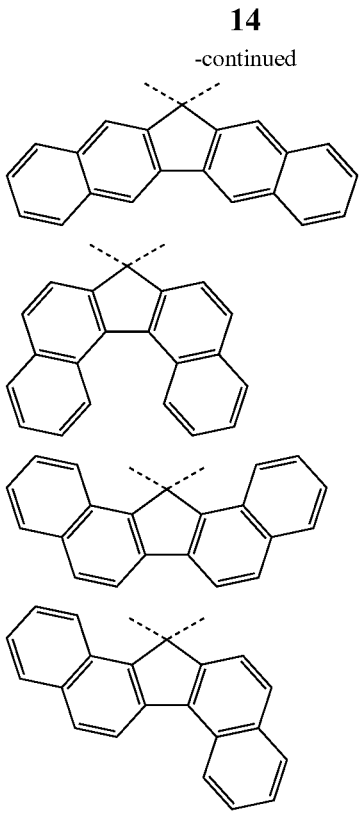

Broken lines represent bonding arms.

In the general formula (1), AR5 and AR6 each represent a benzene ring or a naphthalene ring. AR5 and AR6 each form a benzopyran-type heterocyclic structure including position 9 of the corresponding fluorene. Examples of specific structures thereof include the following etc.

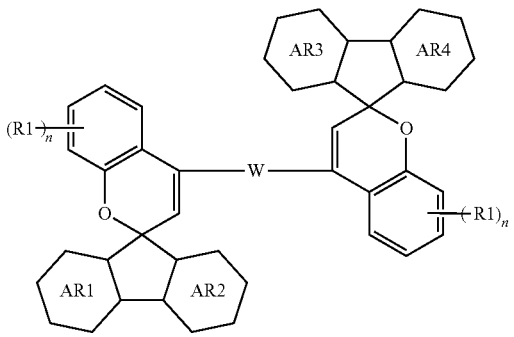

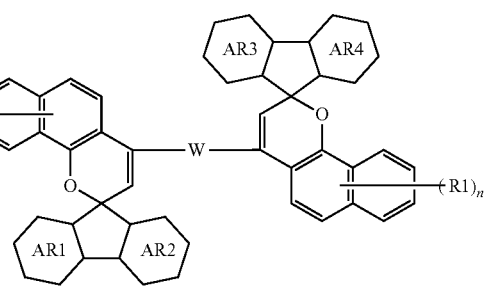

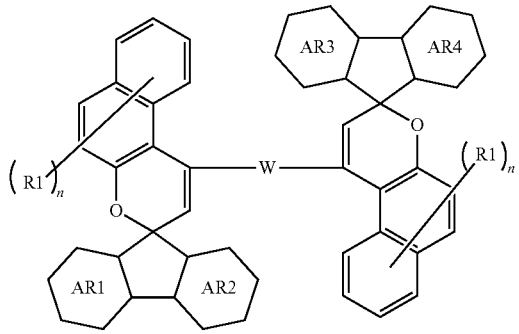

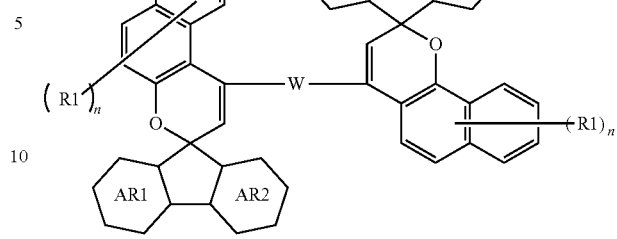

In these formulae, AR1, AR2, AR3, AR4, R1, "n", and W are as defined above.

R1 is any group shown in the formula (2). Additionally, the groups shown in the general formula (2) are substituents for enhancing the solubility into the solvent, polymerization, and curability. From the viewpoint of enhancing the curability, R1 is particularly preferably an ethynyl group or a propargyloxy group.

The inventive compound has condensed aromatic ring structure such as fluorene and benzopyran-type heterocyclic structure. Accordingly, the inventive compound has not only high etching resistance and excellent heat resistance but also thermosetting property, thus enabling fine film formation.

Further, the inventive compound is preferably a compound shown by the following general formula (3).

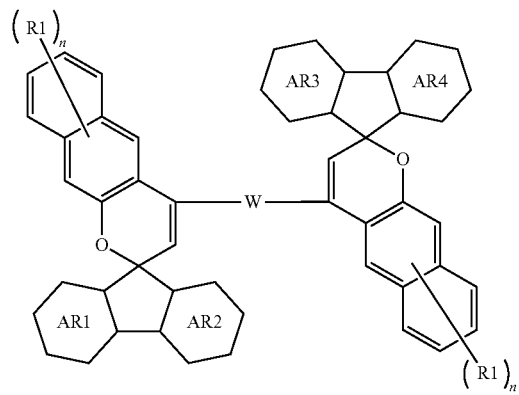

(3)

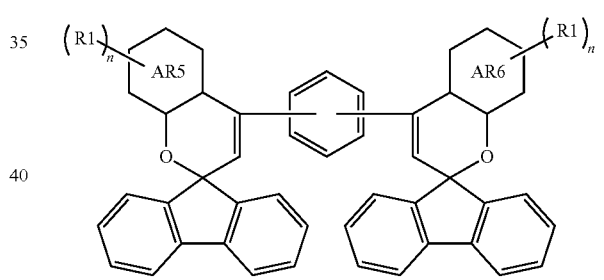

In the general formula (3), AR5, AR6, R1, and "n" are as defined above.

Specific examples of the compound shown by the general formula (3) include the following. Among these, compounds having naphthalene rings at AR5 and AR6 are particularly preferable.

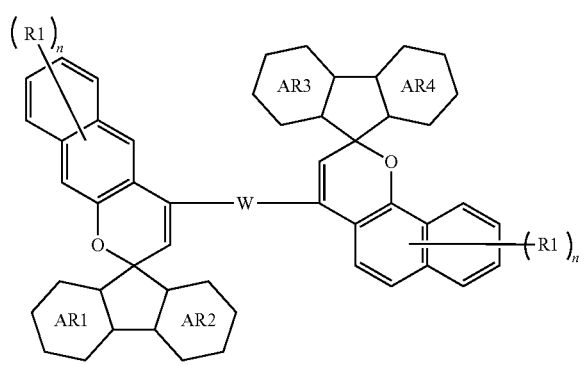

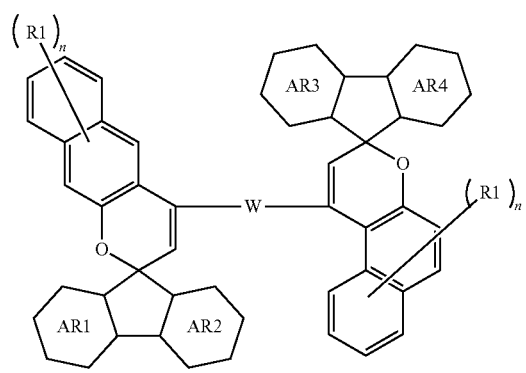

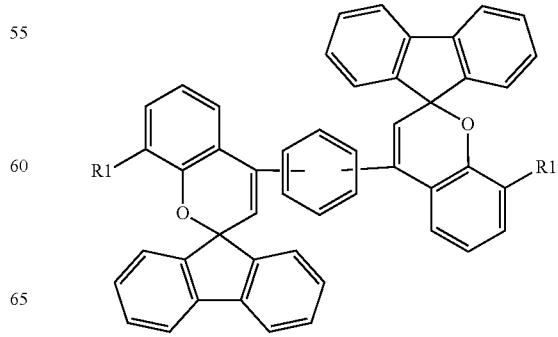

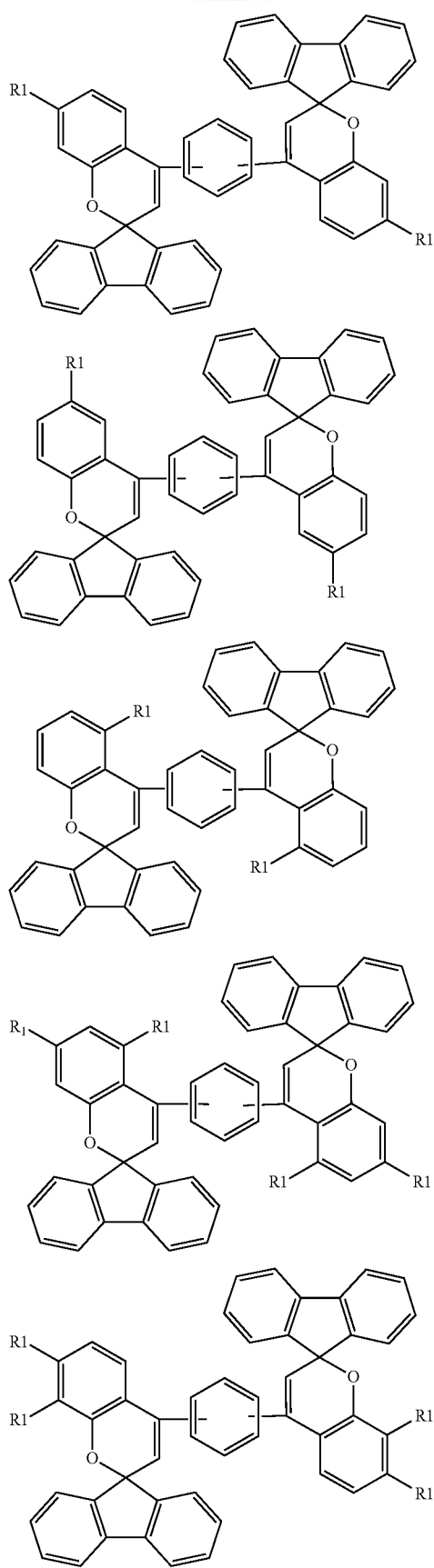
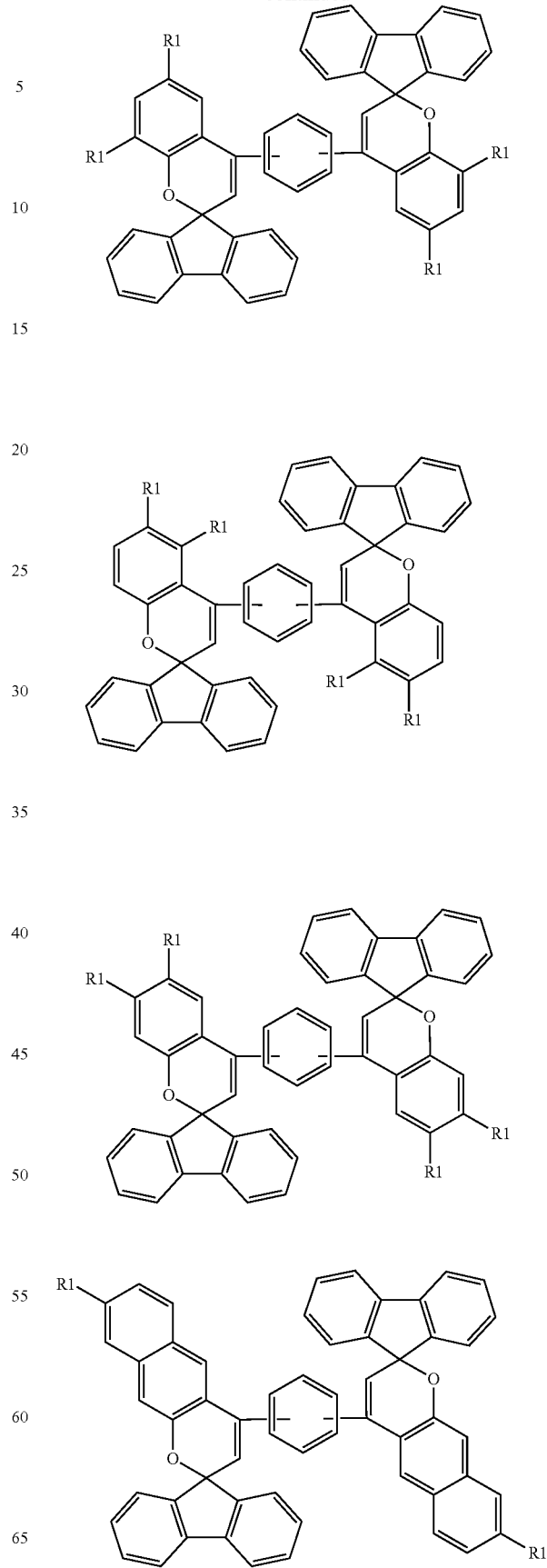

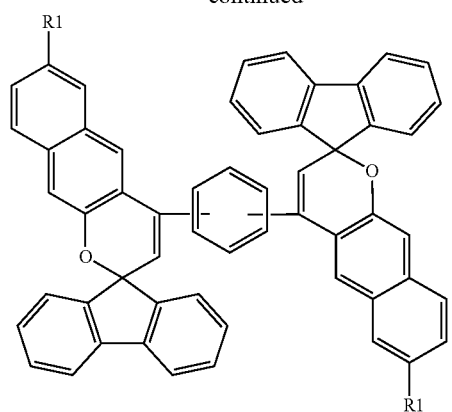
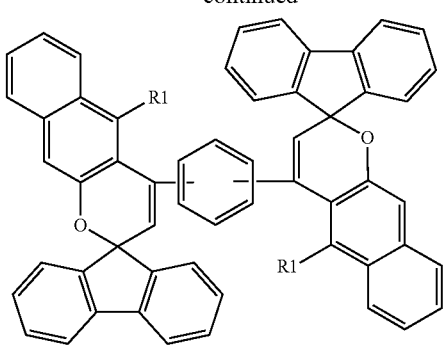
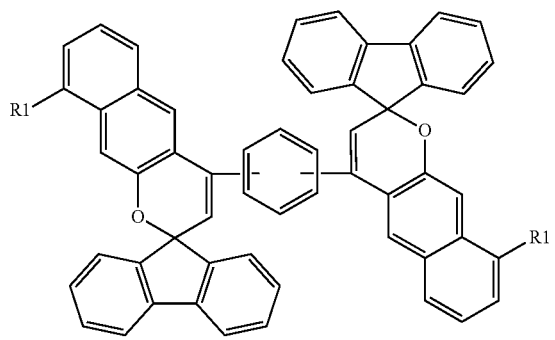
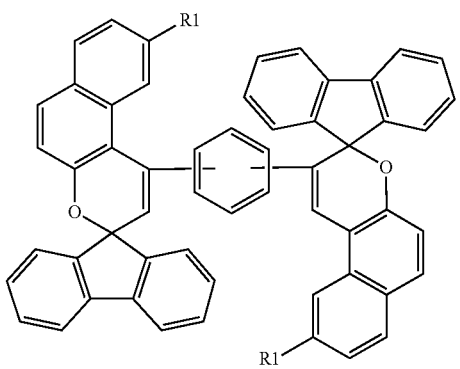
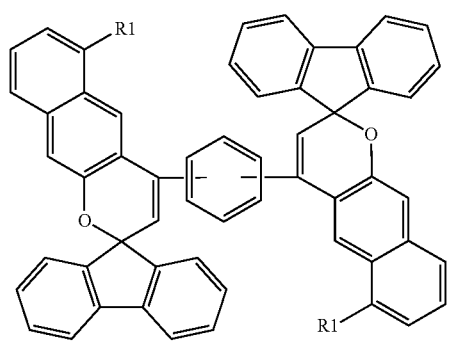
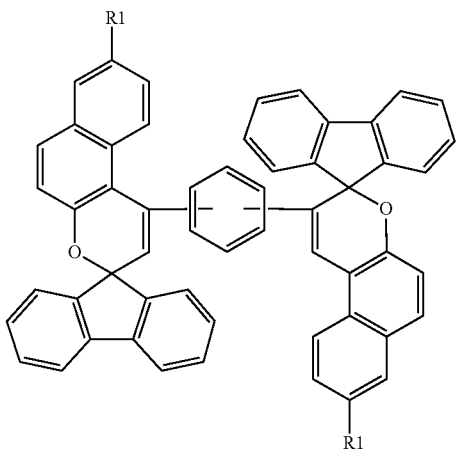
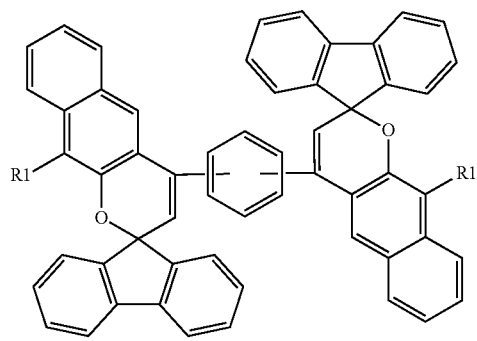
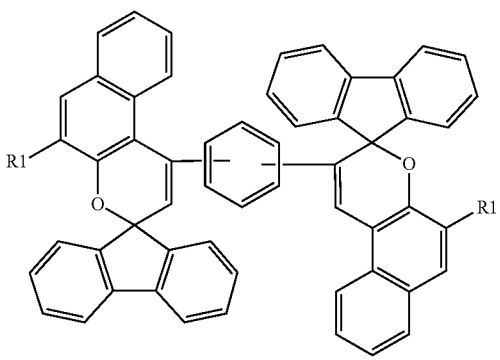

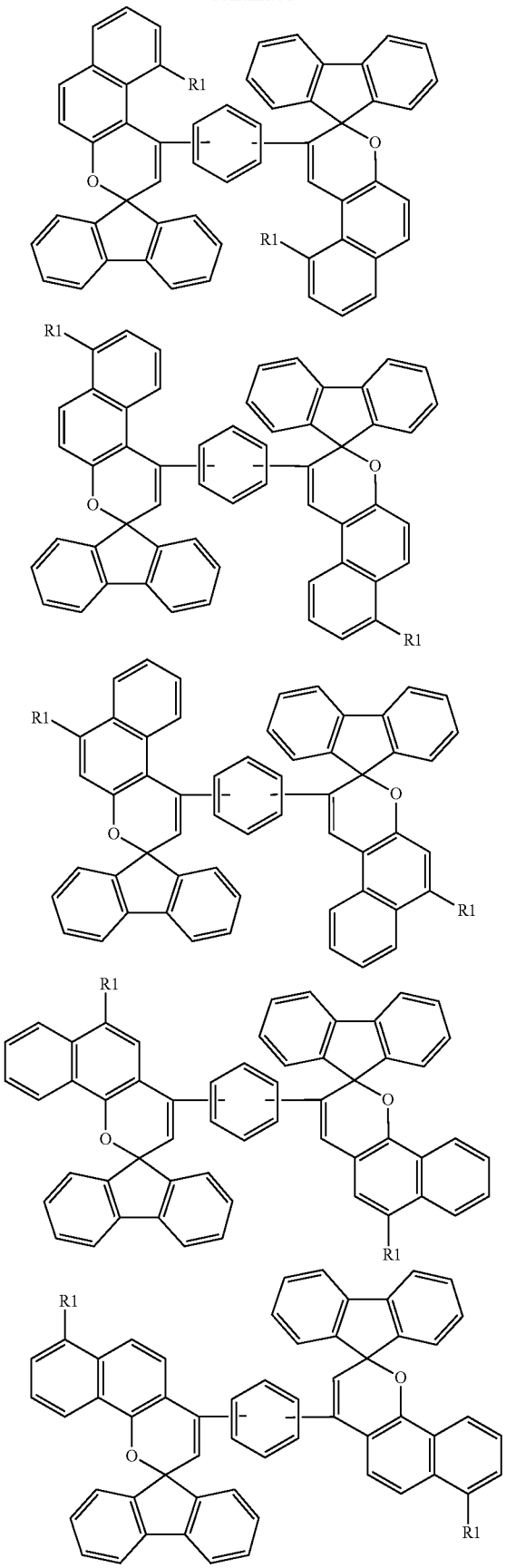

-continued
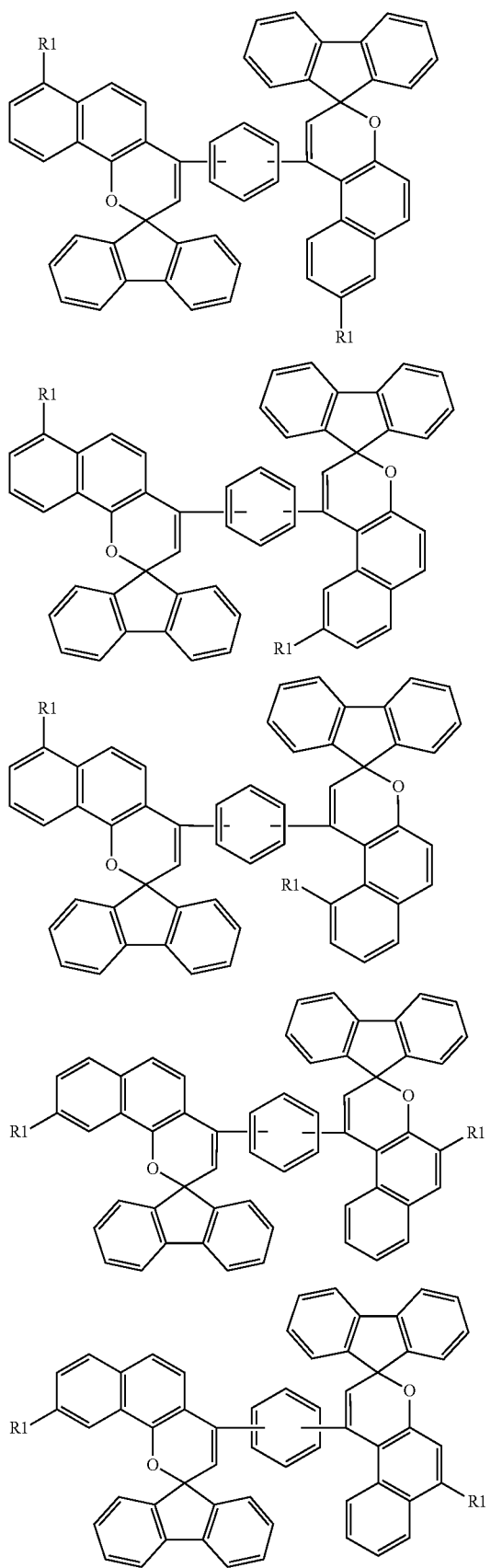
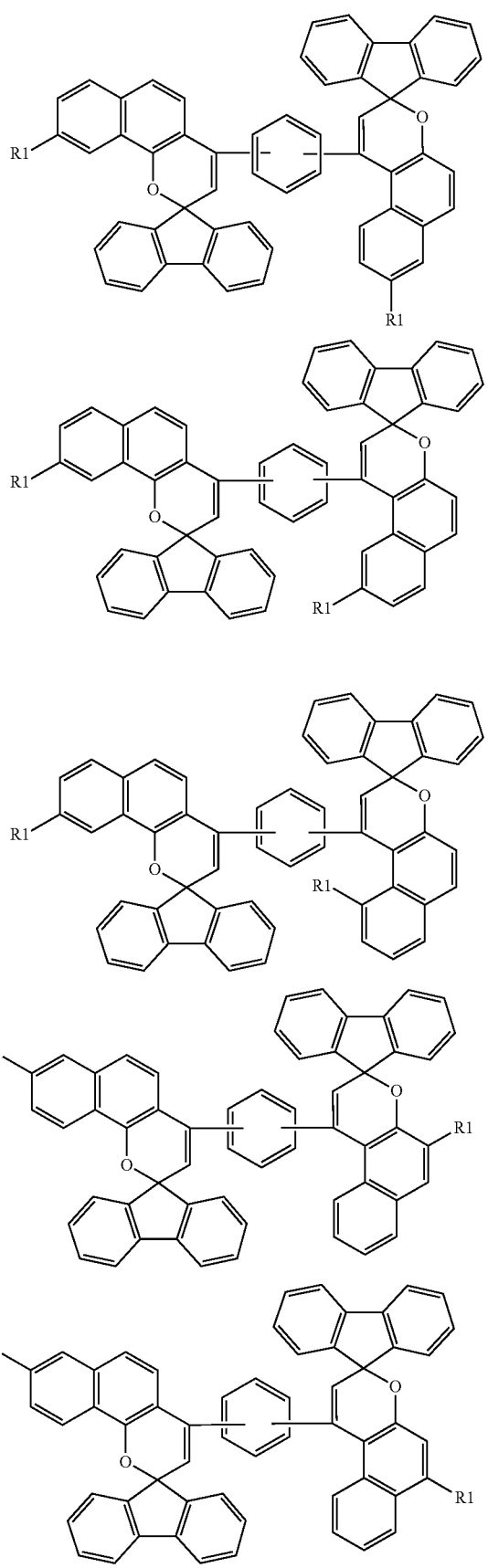

-continued
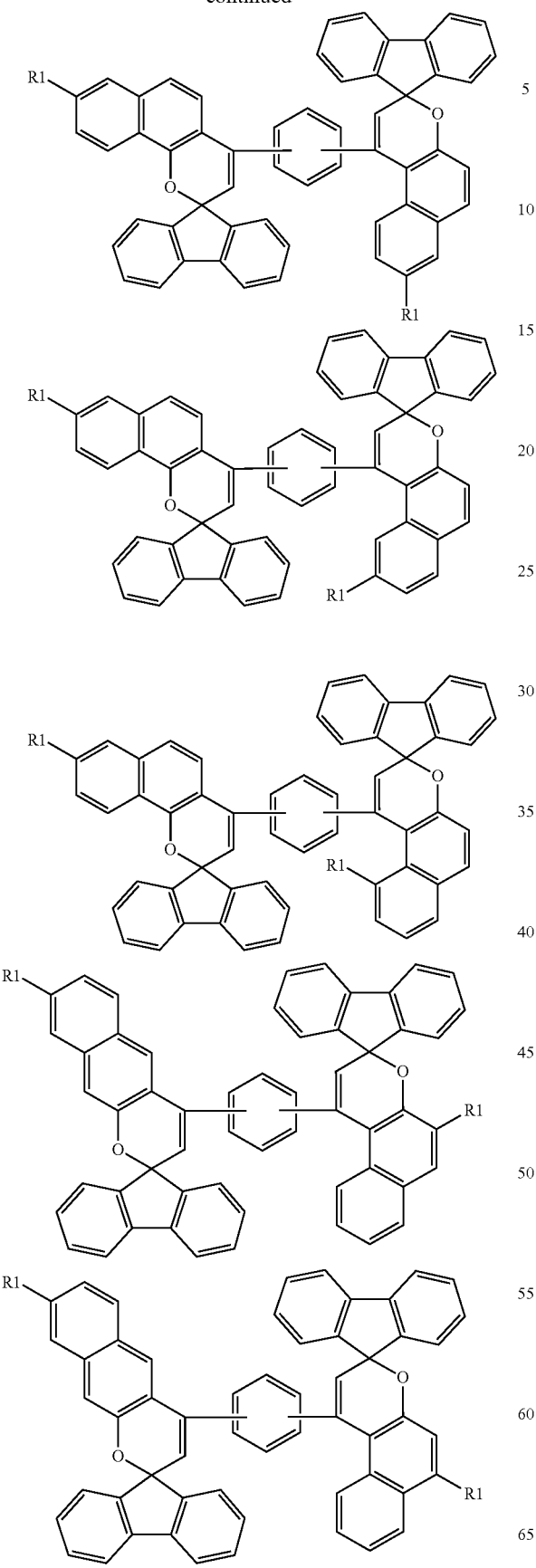
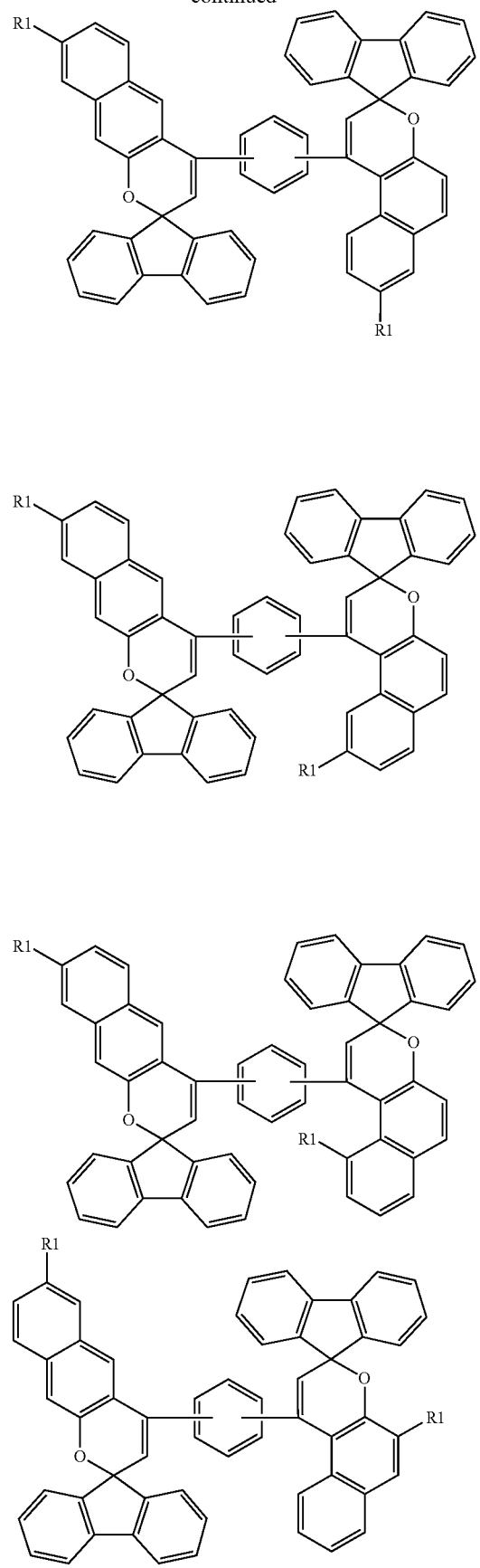

-continued
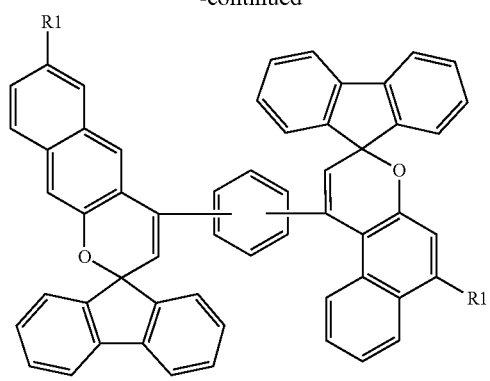
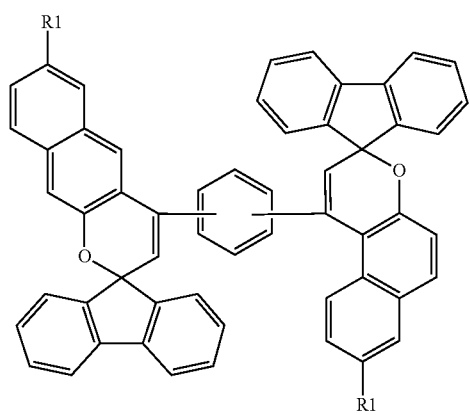
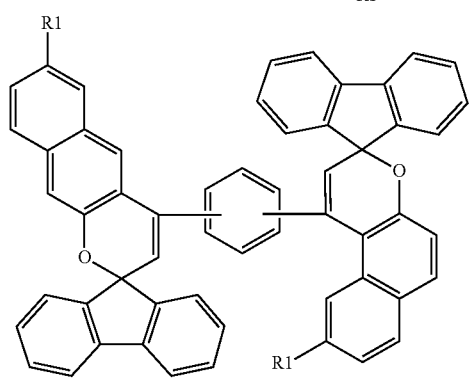
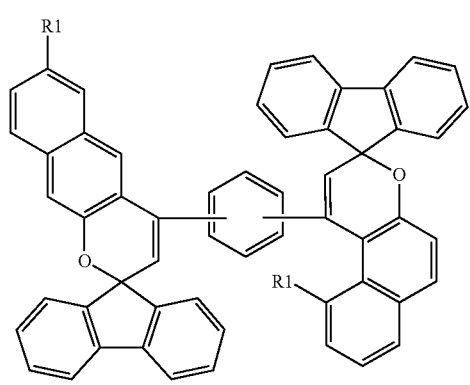
-continued
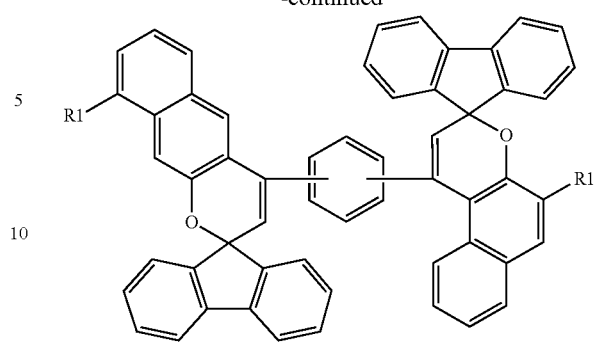
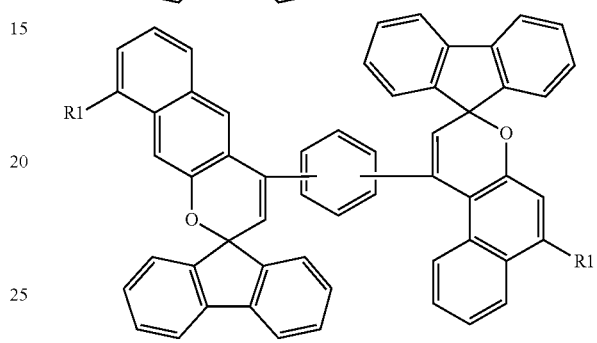
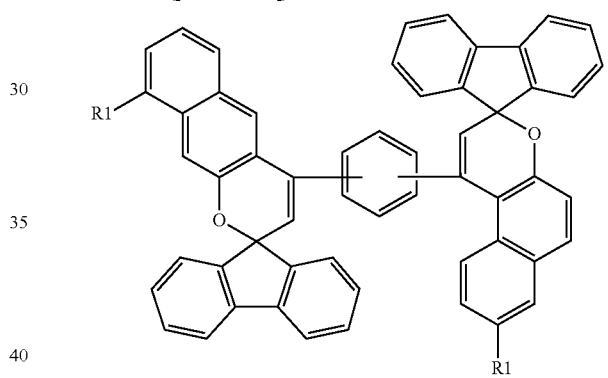
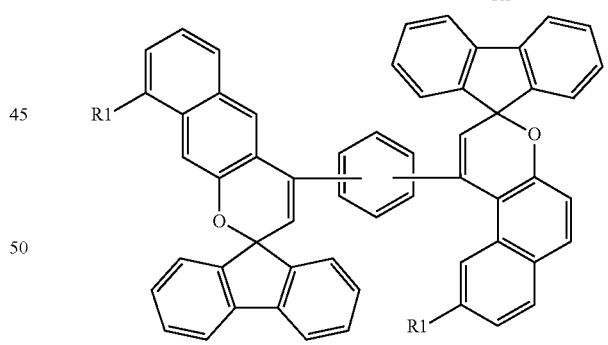
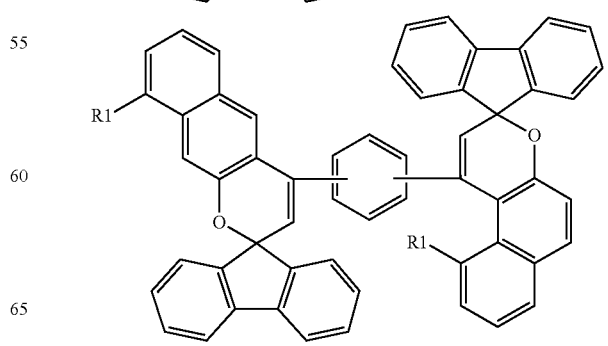

-continued

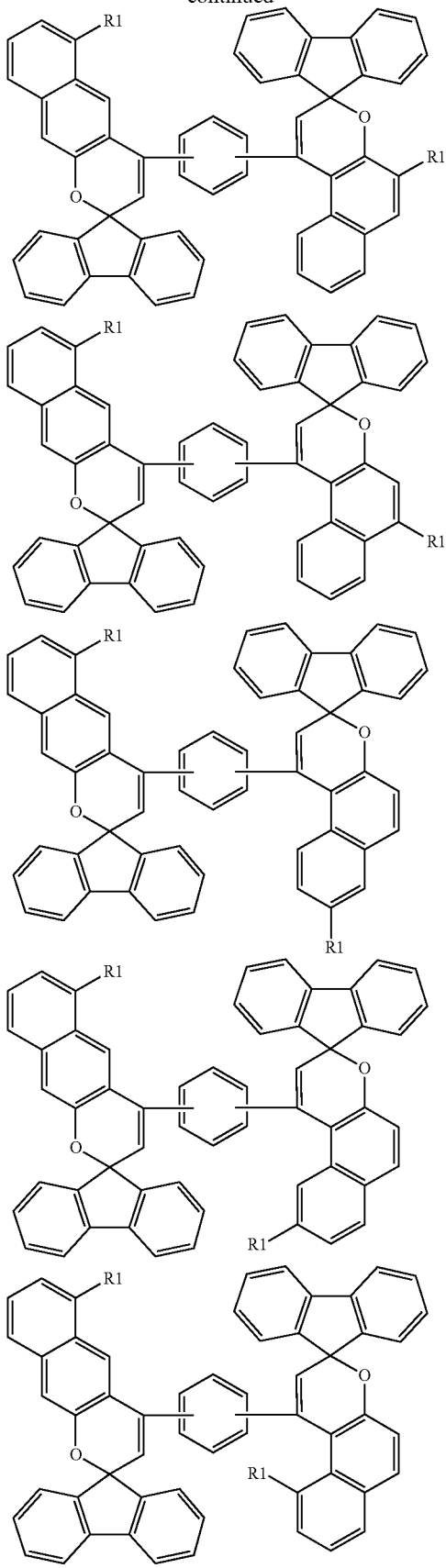

[Compound Production Method]

As an example of the method for producing the inventive compound shown by the general formula (1), the compound can be synthesized by ring formation reaction which is accompanied by dehydration, and which uses a phenol and a fluorenol constituted of AR1, AR2, AR3, AR4, and W as shown below. In the following equation, AR1, AR2, AR3, AR4, R1, "n", and W are as defined above, and ARx represents a benzene ring or a naphthalene ring.

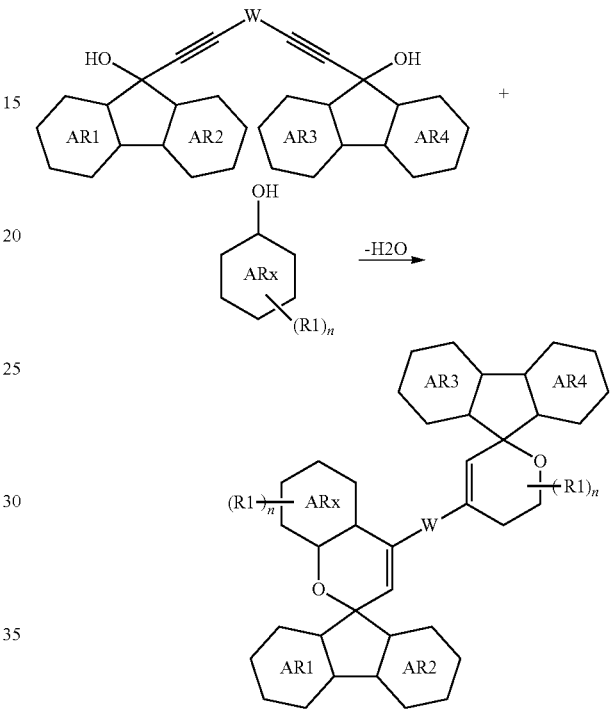

The compound can be obtained generally in an organic solvent in the presence of an acid catalyst at room temperature or under cooling or heating as necessary. Examples of the acid catalyst that can be used include inorganic acids, such as hydrochloric acid, hydrobromic acid, sulfuric acid, nitric acid, phosphoric acid, and heteropoly acid; organic acids, such as oxalic acid, trifluoroacetic acid, methanesulfonic acid, benzenesulfonic acid, p-toluenesulfonic acid, and trifluoromethanesulfonic acid; and Lewis acids, such as aluminum trichloride, aluminum ethoxide, aluminum isopropoxide, boron trifluoride, boron trichloride, boron tribromide, tin tetrachloride, tin tetrabromide, dibutyltin dichloride, dibutyltin dimethoxide, dibutyltin oxide, titanium tetrachloride, titanium tetrabromide, titanium(IV) methoxide, titanium(IV) ethoxide, titanium(IV) isopropoxide, and titanium(IV) oxide.

The solvent to be used is not particularly limited. Examples thereof include: alcohols, such as methanol, ethanol, isopropyl alcohol, butanol, ethylene glycol, propylene glycol, diethylene glycol, glycerol, ethylene glycol monomethyl ether, and propylene glycol monomethyl ether; ethers, such as diethyl ether, dibutyl ether, diethylene glycol diethyl ether, diethylene glycol dimethyl ether, tetrahydrofuran, and 1,4-dioxane; chlorinated solvents, such as methylene chloride, chloroform, dichloroethane, and trichloroethylene; hydrocarbons, such as hexane, heptane, benzene, toluene, xylene, and cumene; nitriles, such as acetonitrile; ketones, such as acetone, ethyl methyl ketone, and isobutyl methyl ketone; esters, such as ethyl acetate, n-butyl acetate, and propylene glycol methyl ether acetate; and non-protic polar solvents, such as dimethylsulfoxide, N,N-dimethylformamide, and hexamethylphosphoric triamide. One of these or a mixture of two or more thereof can be used.

The reaction method include a method in which a phenol, a fluorenol, and an acid catalyst as a catalyst are charged at once; a method in which a phenol and a fluorenol are prepared into a form of dispersion or solution, and then a catalyst is added thereto at once or intermittently, or the catalyst is diluted with a solvent and added dropwise thereto; and a method in which a catalyst is prepared into a form of dispersion or solution, and then a fluorenol and a phenol are added thereto at once or intermittently, or diluted with a solvent and added dropwise thereto. In these events, it is possible to use not only one kind of the phenol and one kind of the fluorenol, but also two or more kinds of each raw material. Although depending on the reactivity of the phenol, the amount of phenol used is preferably 2 mol or more per mol of the fluorenol. After completion of the reaction, the resultant may be diluted with an organic solvent and then subjected to liquid separation and washing to remove the catalyst used for the reaction, and to collect the target product.

The organic solvent used in this event is not particularly limited, as long as it is capable of dissolving the target product and being separated, when mixed with water, into two layers. Examples of the organic solvent include hydrocarbons, such as hexane, heptane, benzene, toluene, and xylene; esters, such as ethyl acetate, n-butyl acetate, and propylene glycol methyl ether acetate; ketones, such as methyl ethyl ketone, methyl amyl ketone, cyclohexanone, and methyl isobutyl ketone; ethers, such as diethyl ether, diisopropyl ether, methyl-t-butyl ether, and ethylcyclopentylmethyl ether; chlorinated solvents, such as methylene chloride, chloroform, dichloroethane, and trichloroethylene; mixtures thereof; etc. As water used for washing in this event, generally, what is called deionized water or ultrapure water may be used. The washing may be performed at least once, preferably once to approximately five times, because washing ten times or more does not always produce the full washing effects thereof.

In the liquid separation and washing, washing with a basic aqueous solution may be performed to remove acidic components in the system. Specific examples of the base include hydroxides of alkaline metals, carbonates of alkaline metals, hydroxides of alkali earth metals, carbonates of alkali earth metals, ammonia, organic ammonium, etc.

Further, in the liquid separation and washing, washing with an acidic aqueous solution may be performed to remove metal impurities or basic components in the system. Specific examples of the acid include inorganic acids, such as hydrochloric acid, hydrobromic acid, sulfuric acid, nitric acid, phosphoric acid, and heteropoly acid; organic acids, such as oxalic acid, fumaric acid, maleic acid, trifluoroacetic acid, methanesulfonic acid, benzenesulfonic acid, p-toluenesulfonic acid, and trifluoromethanesulfonic acid; etc.

The liquid separation and washing may be performed with any one of the basic aqueous solution and the acidic aqueous solution, or can be performed with a combination of the two. The liquid separation and washing is preferably performed with the basic aqueous solution and the acidic aqueous solution in this order from the viewpoint of removing metal impurities.

After the liquid separation and washing with the basic aqueous solution and/or acidic aqueous solution, washing with neutral water may be successively performed. The washing may be performed at least once, preferably once to approximately five times. As the neutral water, deionized water, ultrapure water, or the like mentioned above may be used. The washing may be performed once or more, but if the washing is not performed sufficiently, basic and acidic components cannot be removed in some cases. The washing is preferably performed once to approximately five times because washing ten times or more does not always produce the full washing effects.

Further, after the liquid separation operation, the reaction product can also be collected as a powder by concentrating and drying the solvent or crystallizing the reaction product under reduced pressure or normal pressure. Alternatively, the reaction product can be retained in a solution state with an appropriate concentration to improve the workability in preparing the material for forming an organic film. In this case, the concentration is preferably 0.1 to 50 mass %, more preferably 0.5 to 30 weight %. With such a concentration, the viscosity is hardly high, making it possible to prevent the workability from being impaired; in addition, since the amount of the solvent is not excessive, the solution can be prepared economically.

The solvent used in this event is not particularly limited, as long as it is capable of dissolving the compound. Specific examples of the solvent include ketones, such as cyclohexanone and methyl-2-amyl ketone; alcohols, such as 3-methoxybutanol, 3-methyl-3-methoxybutanol, 1-methoxy-2-propanol, and 1-ethoxy-2-propanol; ethers, such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; and esters, such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate. One of these or a mixture of two or more thereof can be used.

<Polymer used in Material for Forming Organic Film>

A polymer used in the inventive material for forming an organic film is a polymer having a repeating unit shown by the following general formula (4).

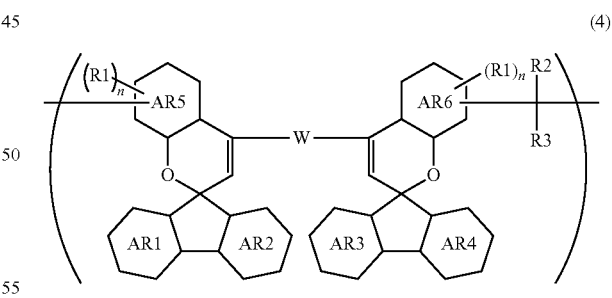

(4)

In the general formula (4), AR1, AR2, AR3, AR4, AR5, AR6, R1, "n", and W are as defined above. R2 and R3 each represent a hydrogen atom or an organic group having 1 to 20 carbon atoms, and optionally bond to each other within a molecule to form a cyclic organic group.

Such polymers can be obtained using a compound shown by the general formula (1). Since the above-described compound is used, the heat resistance, etching resistance, and thermosetting property are excellent. Additionally, since the polymer having a repeating unit is not a monomer, the content of outgassing components is less. Further, the polymer has a molecular weight distribution, so that the degree of crystallinity is lower, and an improvement in the film formability can also be expected.

In the partial structure constituted of R2 and R3 and constituting a part of the repeating unit of the general formula (4), R2 and R3 are each a hydrogen atom or an organic group having 1 to 20 carbon atoms. Alternatively, R2 and R3 may form a cyclic organic group by bonding to each other within a molecule. Specific examples of the partial structure include the following etc. Among the following, a methylene group is preferable in view of availability of the raw material.

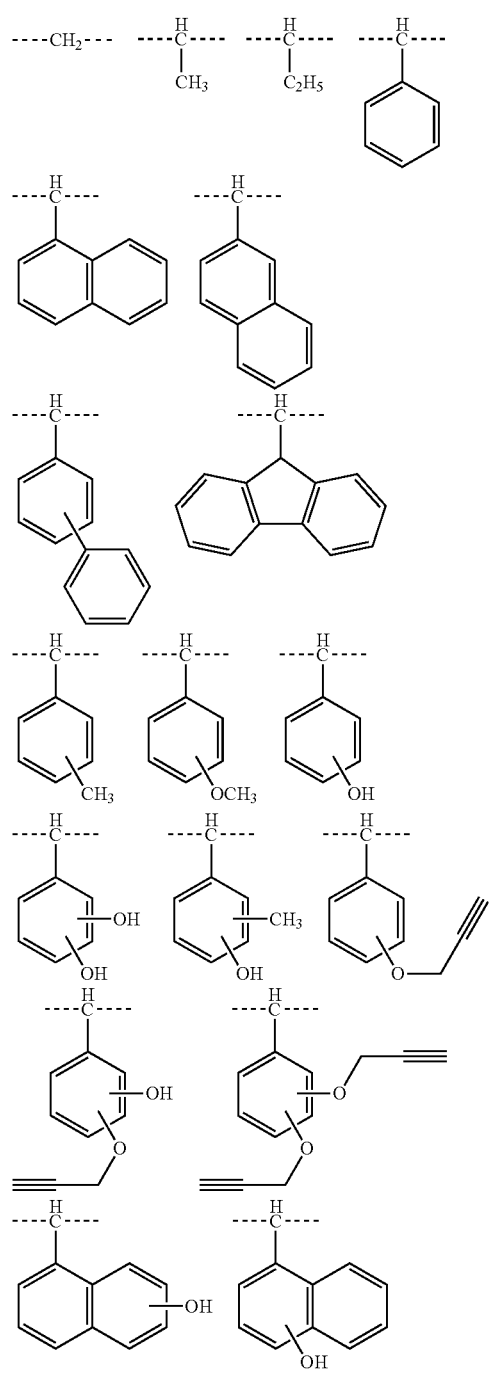

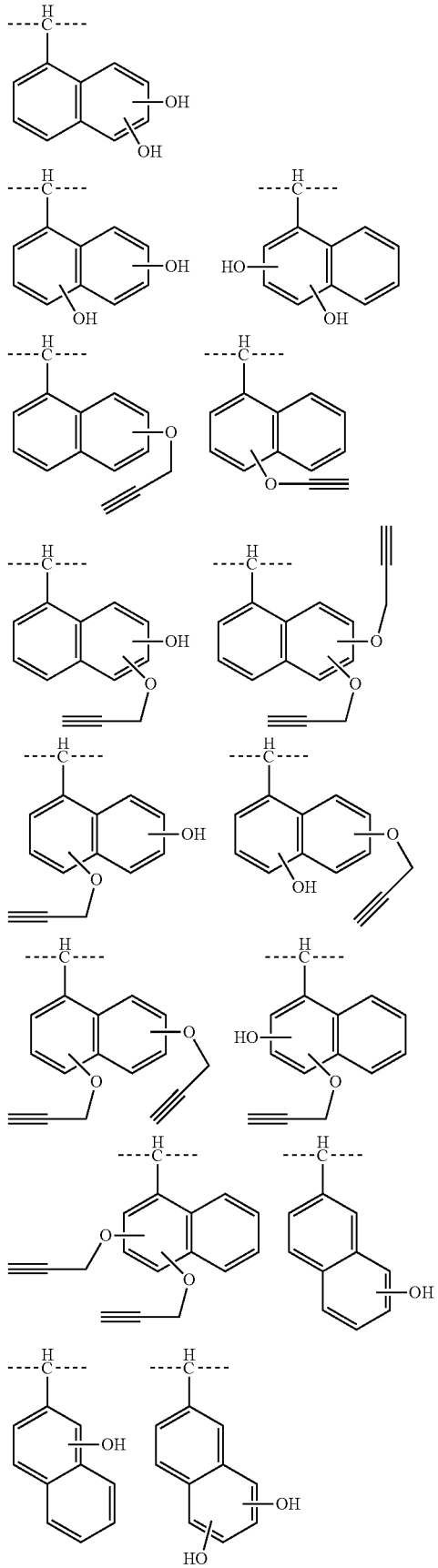

-continued
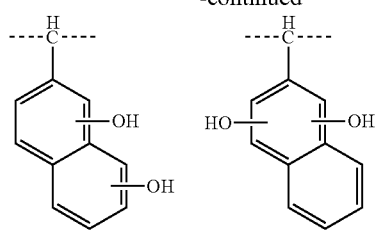
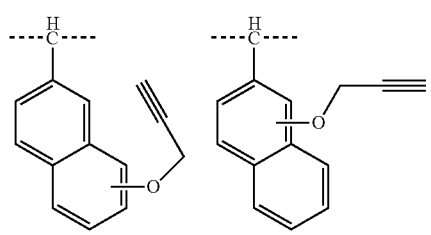
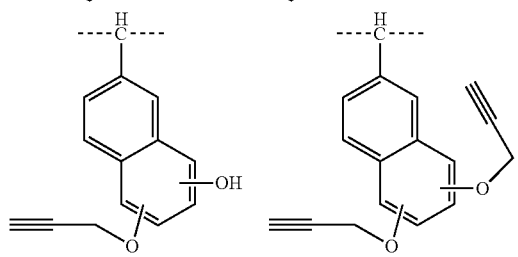
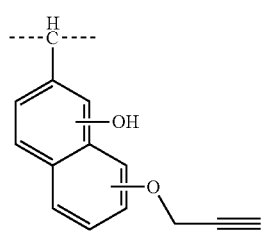
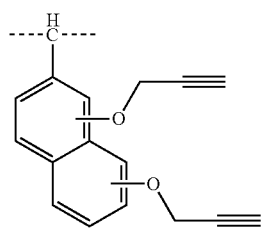
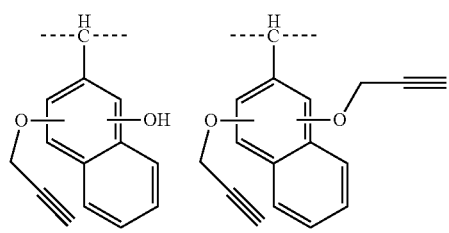
-continued
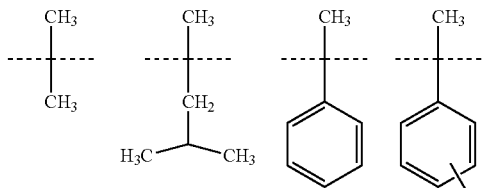
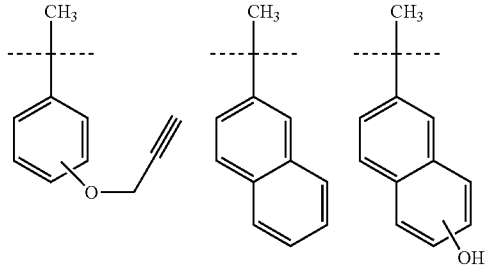
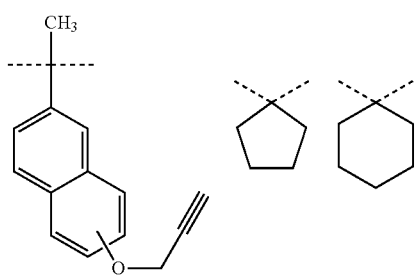
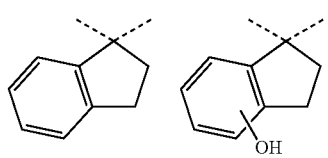
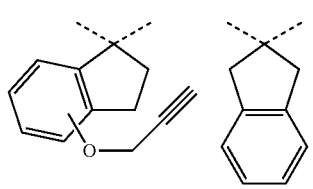
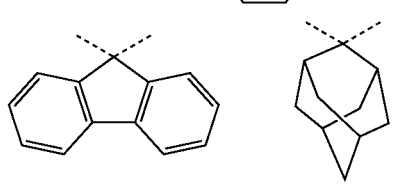

Broken lines represent bonding arms.

Further, the inventive polymer for an organic film material is preferably a polymer having a repeating unit shown by the following general formula (5).

(5)

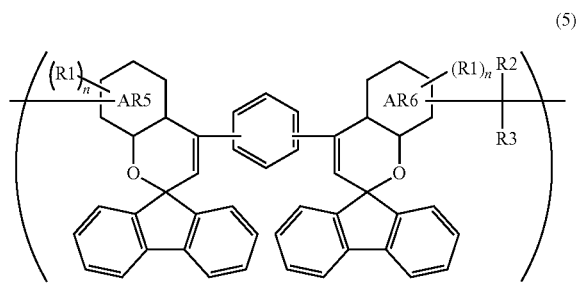

In the general formula (5), AR5, AR6, R1, R2, R3, and "n" are as defined above.

Such polymers can be obtained using a compound shown by the general formula (3).

Further, the above-described polymer has a weight-average molecular weight (Mw) of preferably 1000 to 10000, and the Mw is further preferably 1000 to 5000. Note that the molecular weight can be obtained as a weight-average molecular weight (Mw) in terms of polystyrene by gel permeation chromatography (GPC) using tetrahydrofuran as an eluent.

With the molecular weight within such ranges, the solubility into an organic solvent can be guaranteed, and generation of sublimation product during baking can be suppressed. Moreover, the polymer for an organic film material has favorable thermal flowability. Accordingly, when the polymer is blended into the material, it is possible to not only favorably fill a fine structure formed on a substrate, but also form an organic film that planarizes the entire substrate.

[Polymer Production Method]

As a means for obtaining the inventive polymer for an organic film material, the polymer can be obtained by polycondensation reaction using a compound shown by the general formula (1) and an aldehyde or a ketone. In the following equation, AR1, AR2, AR3, AR4, AR5, AR6, W, R1, R2, R3, and "n" are as defined above (the polycondensation takes place with an aldehyde if at least one of R2 and R3 is a hydrogen atom, or otherwise with a ketone).

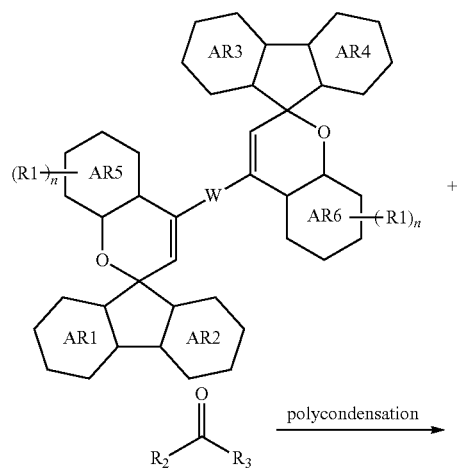

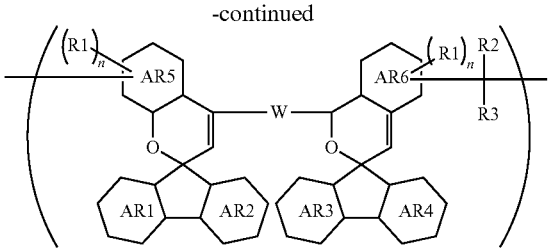

By the polycondensation reaction, the polymer can be obtained generally in an organic solvent in the presence of an acid catalyst at room temperature or under cooling or heating as necessary. Examples of the acid catalyst that can be used include inorganic acids, such as hydrochloric acid, hydrobromic acid, sulfuric acid, nitric acid, phosphoric acid, and heteropoly acid; organic acids, such as oxalic acid, trifluoroacetic acid, methanesulfonic acid, benzenesulfonic acid, p-toluenesulfonic acid, and trifluoromethanesulfonic acid; and Lewis acids, such as aluminum trichloride, aluminum ethoxide, aluminum isopropoxide, boron trifluoride, boron trichloride, boron tribromide, tin tetrachloride, tin tetrabromide, dibutyltin dichloride, dibutyltin dimethoxide, dibutyltin oxide, titanium tetrachloride, titanium tetrabromide, titanium(IV) methoxide, titanium(IV) ethoxide, titanium(IV) isopropoxide, and titanium(IV) oxide.

Examples of the solvent to be used include: alcohols, such as methanol, ethanol, isopropyl alcohol, butanol, ethylene glycol, propylene glycol, diethylene glycol, glycerol, ethylene glycol monomethyl ether, and propylene glycol monomethyl ether; ethers, such as diethyl ether, dibutyl ether, diethylene glycol diethyl ether, diethylene glycol dimethyl ether, tetrahydrofuran, and 1,4-dioxane; chlorinated solvents, such as methylene chloride, chloroform, dichloroethane, and trichloroethylene; hydrocarbons, such as hexane, heptane, benzene, toluene, xylene, and cumene; nitriles, such as acetonitrile; ketones, such as acetone, ethyl methyl ketone, and isobutyl methyl ketone; esters, such as ethyl acetate, n-butyl acetate, and propylene glycol methyl ether acetate; non-protic polar solvents, such as dimethylsulfoxide, N,N-dimethylformamide, and hexamethylphosphoric triamide; etc. One of these or a mixture of two or more thereof can be used.

The polymer can be collected in accordance with the reaction and collection methods described for producing the compound shown by the general formula (1).

[Alternative Methods for Producing Compound and Polymer]

In the case where the substituent represented by R1 is propargyl ether in either the compound or polymer used in the inventive material for forming an organic film, the compound or polymer can be produced by, for example, a method in which a compound or polymer having a hydroxyl group as an intermediate is subjected to propargyl etherification as shown below. This reaction is not particularly limited, as long as the propargyl ether groups can be introduced. Examples of the reaction include a substitution reaction as follows which uses a base catalyst and a halide, tosylate, or mesylate having a propargyl group, etc. In the following equations, X represents a halogen, a tosyl group, or a mesyl group; and AR1, AR2, AR3, AR4, AR5, AR6, W, R2, R3, and "n" are as defined above.

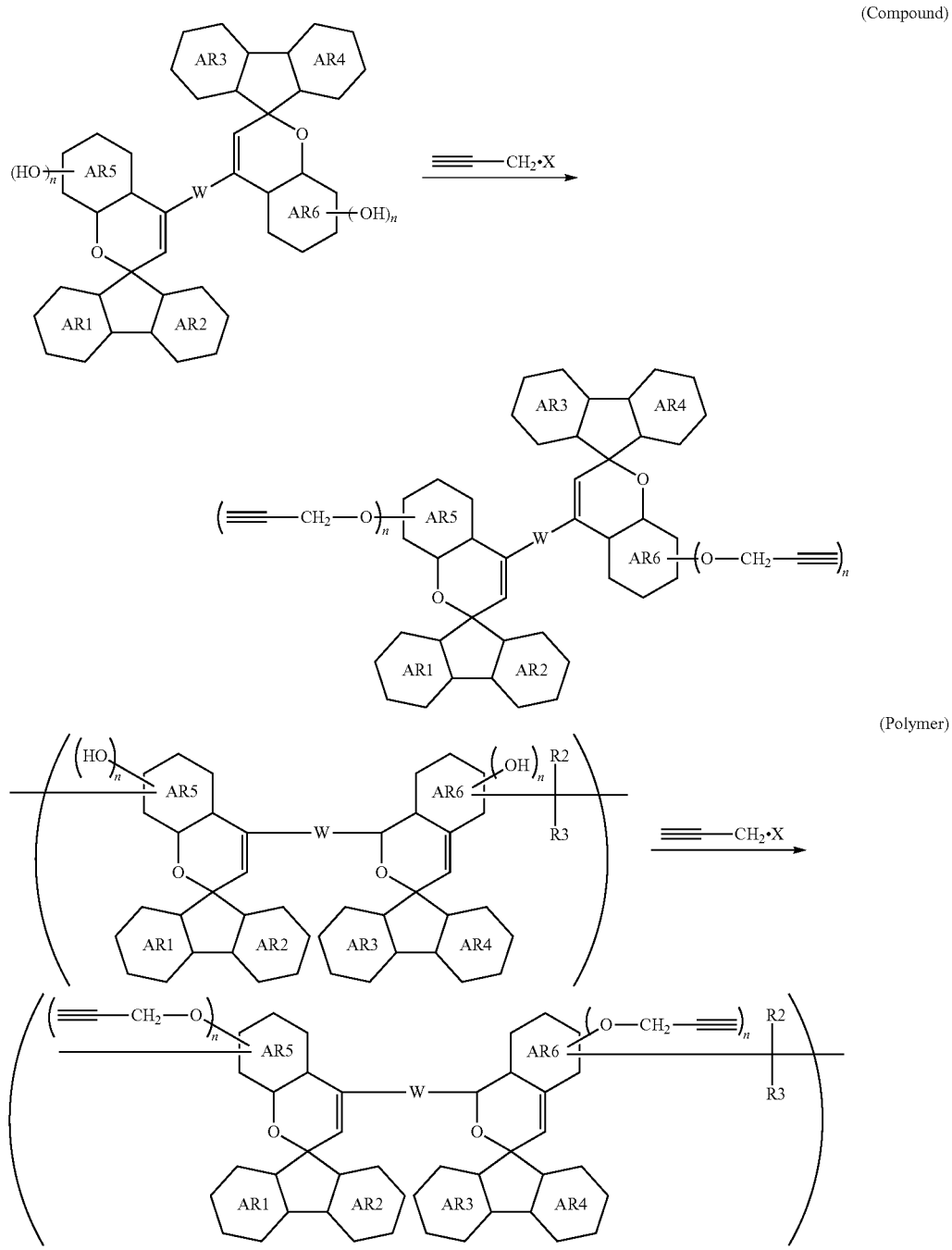

(Compound)

(Polymer)

Examples of the base catalyst used in the substitution reaction include inorganic base compounds, such as sodium hydrogen carbonate, sodium carbonate, potassium carbonate, calcium carbonate, cesium carbonate, sodium hydroxide, potassium hydroxide, sodium hydride, and potassium phosphate; organic amine compounds, such as triethylamine, pyridine, and N-methylmorpholine; etc. One of these or a combination of two or more thereof may be used.

The solvent used in this event is not particularly limited, as long as the solvent is inactive in the reaction. Examples of the solvent include ether-based solvents, such as diethyl ether, tetrahydrofuran, and dioxane; aromatic solvents, such as benzene, toluene, and xylene; acetonitrile, dimethylsulfoxide, N,N-dimethylformamide, N-methylpyrrolidone, water, etc. One of these or a mixture thereof can be used.

The compound and polymer can be collected in accordance with the reaction and collection methods described for producing the compound shown by the general formula (1).

In the preparation of the compound or polymer used in an organic film material obtained according to this method, various halides, tosylates, and mesylates can be used alone or in combination, depending on the required performances. For example, compounds having a side chain structure for enhancing planarizing property, a rigid aromatic ring structure for enhancing etching resistance and heat resistance, and so forth can be combined at a certain ratio. Thus, a material for forming an organic film (organic film material), which uses these polymers, can achieve all of filling property, planarizing property, and etching resistance at high levels.

As described above, the inventive compound and/or polymer used in an organic film material enable the organic film material to exhibit high etching resistance and excellent twisting resistance.

<Material for Forming Organic Film>

The present invention further provides a material for forming an organic film, containing: (A) the inventive compound and/or polymer used for an organic film material described above; and (B) an organic solvent.

[(A) Inventive Compound and/or Polymer]

In the inventive material for forming an organic film, one of the inventive compound and polymer for an organic film material can be used, or a combination thereof can be used.

Further, in the present invention, one or more kinds of each of the compound and polymer for an organic film material are preferably selected and incorporated.

With such mixtures as above, various properties required for organic film usages, such as filling property, planarizing property, and outgassing property against sublimation product, can be adjusted within appropriate ranges.

[(B) Organic Solvent]

The organic solvent usable in the inventive material for forming an organic film is not particularly limited, as long as the organic solvent dissolves the compound and/or the polymer (base polymer) and, if any, an acid generator, a crosslinking agent, and other additives to be described later, for example. Specifically, a solvent having a boiling point of lower than 180° C. can be used, such as solvents disclosed in paragraphs [0091] to [0092] of JP 2007-199653 A. Above all, it is preferable to use propylene glycol monomethyl ether acetate, propylene glycol monomethyl ether, 2-heptanone, cyclopentanone, cyclohexanone, and a mixture of two or more thereof. The organic solvent is blended in an amount of preferably 200 to 10,000 parts, more preferably 300 to 5,000 parts, based on 100 parts of the compound and/or polymer (A).

Such a material for forming an organic film can be applied by spin coating. Since the inventive compound and/or polymer for an organic film material as described above is incorporated, the material for forming an organic film enables all of favorable dry etching resistance, high heat resistance, and high filling and planarizing properties.

Further, in the inventive material for forming an organic film, it is also possible to add, as a component of the organic solvent, a high-boiling-point solvent having a boiling point of 180° C. or higher to the above-described solvent having a boiling point of lower than 180° C. (a mixture of a solvent having a boiling point of lower than 180° C. and a solvent having a boiling point of 180° C. or higher). The high-boiling-point organic solvent is not particularly limited to hydrocarbons, alcohols, ketones, esters, ethers, chlorinated solvents, and so forth, as long as the high-boiling-point organic solvent is capable of dissolving the compound and/or the polymer for an organic film material. Specific examples of the high-boiling-point organic solvent include 1-octanol, 2-ethylhexanol, 1-nonanol, 1-decanol, 1-undecanol, ethylene glycol, 1,2-propylene glycol, 1,3-butylene glycol, 2,4-pentanediol, 2-methyl-2,4-pentanediol, 2,5-hexanediol, 2,4-heptanediol, 2-ethyl-1,3-hexanediol, diethylene glycol, dipropylene glycol, triethylene glycol, tripropylene glycol, glycerin, n-nonyl acetate, ethylene glycol monohexyl ether, ethylene glycol mono-2-ethylhexyl ether, ethylene glycol monophenyl ether, ethylene glycol monobenzyl ether, diethylene glycol monoethyl ether, diethylene glycol monoisopropyl ether, diethylene glycol mono-n-butyl ether, diethylene glycol monoisobutyl ether, diethylene glycol monohexyl ether, diethylene glycol monophenyl ether, diethylene glycol monobenzyl ether, diethylene glycol diethyl ether, diethylene glycol dibutyl ether, diethylene glycol butylmethyl ether, triethylene glycol dimethyl ether, triethylene glycol monomethyl ether, triethylene glycol-n-butyl ether, triethylene glycol butylmethyl ether, triethylene glycol diacetate, tetraethylene glycol dimethyl ether, dipropylene glycol monomethyl ether, dipropylene glycol mono-n-propyl ether, dipropylene glycol mono-n-butyl ether, tripropylene glycol dimethyl ether, tripropylene glycol monomethyl ether, tripropylene glycol mono-n-propyl ether, tripropylene glycol mono-n-butyl ether, ethylene glycol monoethyl ether acetate, ethylene glycol monobutyl ether acetate, diethylene glycol monomethyl ether acetate, diethylene glycol monoethyl ether acetate, diethylene glycol monobutyl ether acetate, triacetin, propylene glycol diacetate, dipropylene glycol monomethyl ether acetate, dipropylene glycol methyl-n-propyl ether, dipropylene glycol methyl ether acetate, 1,4-butanediol diacetate, 1,3-butylene glycol diacetate, 1,6-hexanediol diacetate, triethylene glycol diacetate, γ-butyrolactone, dihexyl malonate, diethyl succinate, dipropyl succinate, dibutyl succinate, dihexyl succinate, dimethyl adipate, diethyl adipate, dibutyl adipate, etc. One or a mixture of these may be used.

The boiling point of the high-boiling-point solvent(s) may be appropriately selected according to the temperature at which the material for forming an organic film is heated. The boiling point of the high-boiling-point solvent(s) to be added is preferably 180° C. to 300° C., more preferably 200° C. to 300° C. Such boiling points prevent the evaporation rate at baking (heating) from becoming excessive, which would otherwise occur if the boiling point is too low. Thus, the boiling points can provide sufficient thermal flowability. Moreover, such boiling points are not too high, so that the high-boiling-point solvent(s) evaporate and do not remain in the film after baking; thus, the boiling points do not adversely affect the film physical properties, such as etching resistance.

Moreover, when the high-boiling-point solvent(s) are used, the high-boiling-point solvent(s) are blended in an amount of preferably 1 to 30 parts by mass based on 100 parts by mass of the solvent(s) having a boiling point of lower than 180° C. Such a formulation amount prevents a failure in providing sufficient thermal flowability during baking, which would otherwise occur if the formulation amount is too small. In addition, degradation of the film physical properties such as etching resistance is prevented, which would otherwise occur if the formulation amount is so large that the solvent(s) remain in the film.

Such a material for forming an organic film has thermal flowability imparted by adding the high-boiling-point solvent to the above-described material for forming an organic film. Thus, the resulting composition for forming an organic film has both high filling and planarizing properties.

[(C) Acid Generator]

In the inventive material for forming an organic film, an acid generator (C) can be added so as to further promote the curing reaction. The acid generator includes a material that generates an acid by thermal decomposition, and a material that generates an acid by light irradiation. Any of these can be added. Specifically, materials disclosed in paragraphs [0061] to [0085] of JP 2007-199653 A can be added, but the present invention is not limited thereto.

One kind of the acid generator can be used singly, or two or more kinds thereof can be used in combination. When an acid generator is added, the acid generator is added in an amount of preferably 0.05 to 50 parts, more preferably 0.1 to 10 parts, based on 100 parts of the compound and/or polymer (A).

[(D) Surfactant]

To the inventive material for forming an organic film, a surfactant (D) can be added so as to enhance the coating property in spin coating. As the surfactant, for example, those disclosed in [0142] to [0147] of JP 2009-269953 A can be used. When a surfactant is added, the surfactant is added in an amount of preferably 0.01 to 10 parts, more preferably 0.05 to 5 parts, based on 100 parts of the compound and/or polymer (A).

[(E) Crosslinking Agent]

Moreover, to the inventive material for forming an organic film, a crosslinking agent can also be added so as to increase the curability and to further suppress intermixing with an upper layer film. The crosslinking agent is not particularly limited, and known various types of crosslinking agents can be widely used. Examples thereof can include methylolated- or alkoxymethylated polynuclear phenol-based crosslinking agents, melamine-based crosslinking agents, glycoluril-based crosslinking agents, benzoguanamine-based crosslinking agents, urea-based crosslinking agents, β-hydroxyalkylamide-based crosslinking agents, isocyanurate-based crosslinking agents, aziridine-based crosslinking agents, oxazoline-based crosslinking agents, and epoxy-based crosslinking agents. When a crosslinking agent is added, the crosslinking agent is added in an amount of preferably 1 to 100 parts, more preferably 5 to 50 parts, based on 100 parts of the compound and/or polymer (A).

Specific examples of the melamine-based crosslinking agents include hexamethoxymethylated melamine, hexabutoxymethylated melamine, alkoxy- and/or hydroxy-substituted derivatives thereof, and partial self-condensates thereof. Specific examples of the glycoluril-based crosslinking agents include tetramethoxymethylated glycoluril, tetrabutoxymethylated glycoluril, alkoxy- and/or hydroxy-substituted derivatives thereof, and partial self-condensates thereof. Specific examples of the benzoguanamine-based crosslinking agents include tetramethoxymethylated benzoguanamine, tetrabutoxymethylated benzoguanamine, alkoxy- and/or hydroxy-substituted derivatives thereof, and partial self-condensates thereof. Specific examples of the urea-based crosslinking agents include dimethoxymethylated dimethoxyethyleneurea, alkoxy- and/or hydroxy-substituted derivatives thereof, and partial self-condensates thereof. A specific example of the β-hydroxyalkylamide-based crosslinking agents includes N,N,N',N'-tetra(2-hydroxyethyl)adipic acid amide. Specific examples of the isocyanurate-based crosslinking agents include triglycidyl isocyanurate and triallyl isocyanurate. Specific examples of the aziridine-based crosslinking agents include 4,4'-bis(ethyleneiminocarbonylamino)diphenylmethane and 2,2-bishydroxymethylbutanol-tris[3-(1-aziridinyl)propionate]. Specific examples of the oxazoline-based crosslinking agents include 2,2'-isopropylidene bis(4-benzyl-2-oxazoline), 2,2'-isopropylidene bis(4-phenyl-2-oxazoline), 2,2'-methylenebis4,5-diphenyl-2-oxazoline, 2,2'-methylenebis-4-phenyl-2-oxazoline, 2,2'-methylenebis-4-tert-butyl-2-oxazoline, 2,2'-bis(2-oxazoline), 1,3-phenylenebis(2-oxazoline), 1,4-phenylenebis(2-oxazoline), and a 2-isopropenyl oxazoline copolymer. Specific examples of the epoxy-based crosslinking agents include diglycidyl ether, ethylene glycol diglycidyl ether, 1,4-butanediol diglycidyl ether, 1,4-cyclohexanedimethanol diglycidyl ether, poly(glycidyl methacrylate), trimethylolethane triglycidyl ether, trimethylolpropane triglycidyl ether, and pentaerythritol tetraglycidyl ether.

Specific examples of the polynuclear phenol-based crosslinking agents include a compound shown by the following general formula (6).

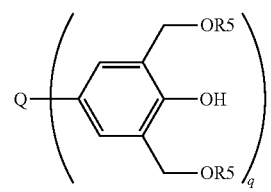

(6)

In the formula, Q represents a single bond, or a hydrocarbon group with a valency of "q" having 1 to 20 carbon atoms. R5 represents a hydrogen atom, or an alkyl group having 1 to 20 carbon atoms. "q" represents an integer of 1 to 5.

Q is a single bond, or a hydrocarbon group having a valency of "q" and 1 to 20 carbon atoms. "q" is an integer of 1 to 5, more preferably 2 or 3. Specific examples of Q include such groups of methane, ethane, propane, butane, isobutane, pentane, cyclopentane, hexane, cyclohexane, methylpentane, methylcyclohexane, dimethylcyclohexane, trimethylcyclohexane, benzene, toluene, xylene, ethylbenzene, ethylisopropylbenzene, diisopropylbenzene, methylnaphthalene, ethylnaphthalene, and eicosane from each of which "q" hydrogen atoms are excluded. R5 is a hydrogen atom, or an alkyl group having 1 to 20 carbon atoms. Specific examples of the alkyl group having 1 to 20 carbon atoms include methyl, ethyl, propyl, isopropyl, butyl, isobutyl, pentyl, isopentyl, hexyl, octyl, ethylhexyl, decyl, and eicosanyl groups. R5 is a preferably hydrogen atom or a methyl group.

Specific examples of the compound shown by the general formula (6) include the following compounds. Among these, triphenolmethane, triphenolethane, 1,1,1-tris(4-hydroxyphenyl)ethane, and tris(4-hydroxyphenyl)-1-ethyl-4-isopropylbenzene that are subjected to hexamethoxymethylation are preferable from the viewpoints of enhancing the curability and film thickness uniformity of the organic film.

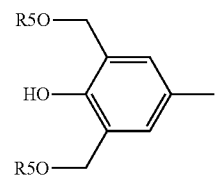

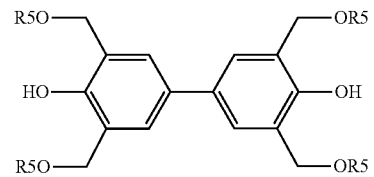

-continued
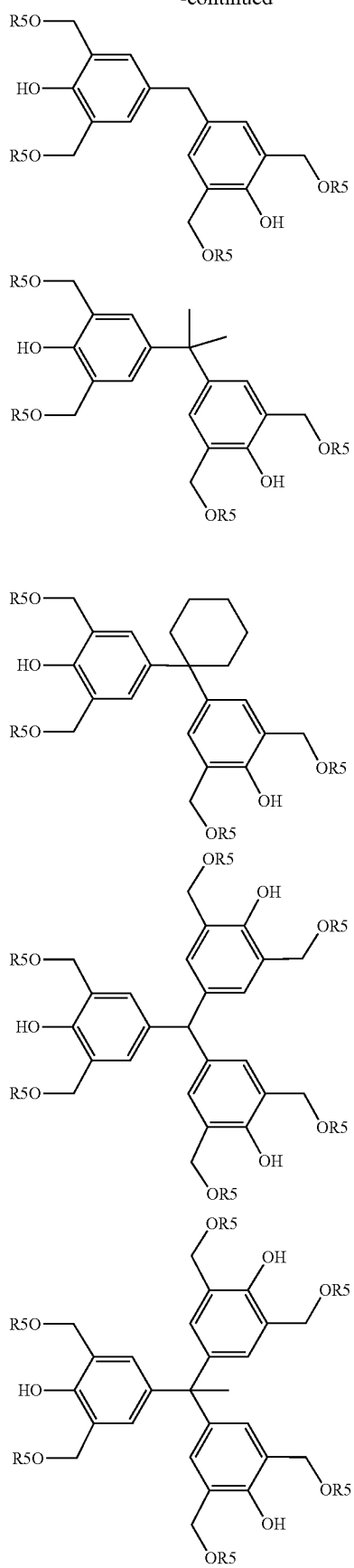
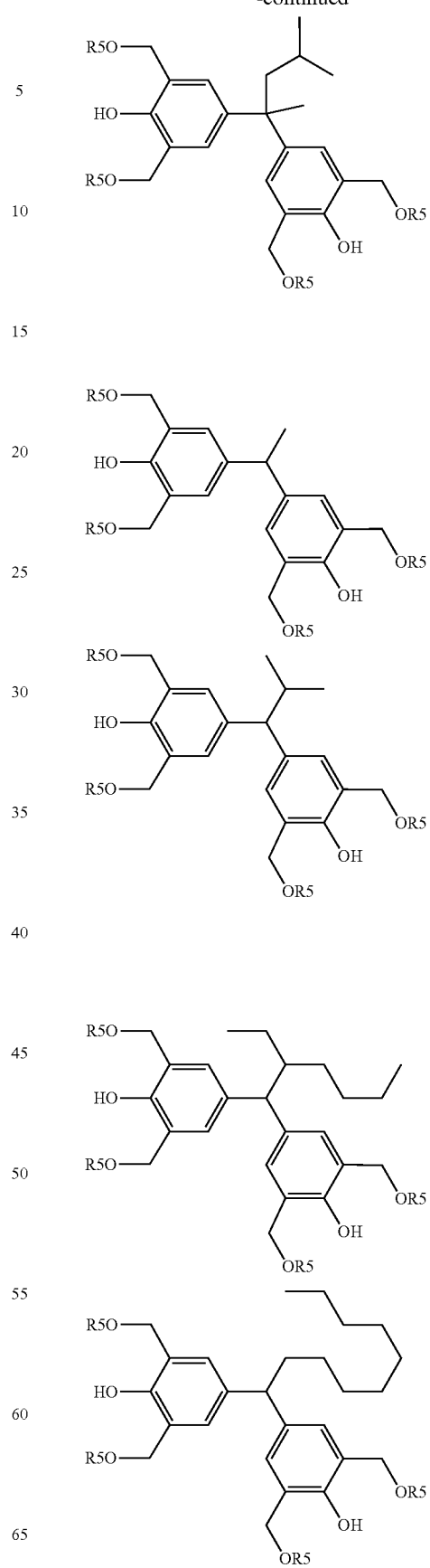

47
-continued
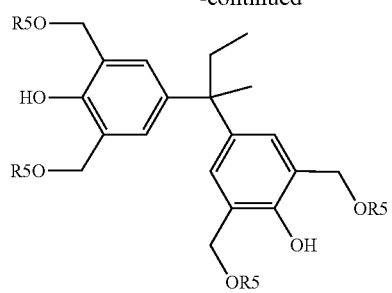
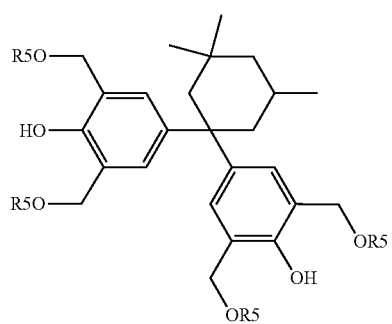
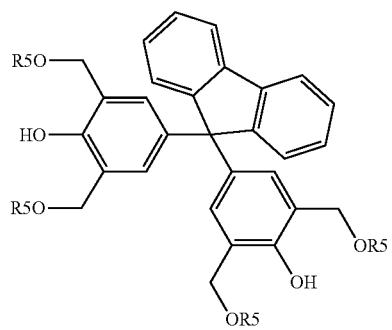
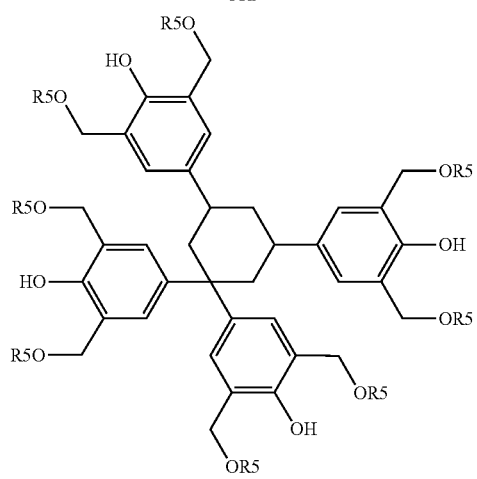
48
-continued
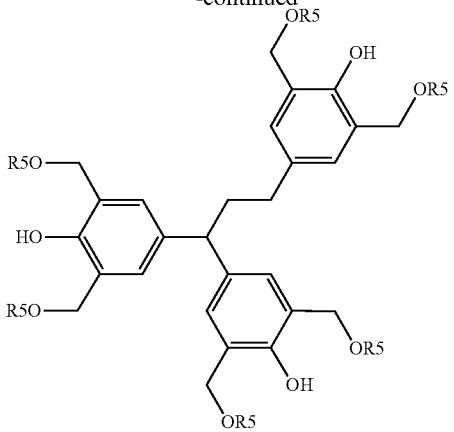
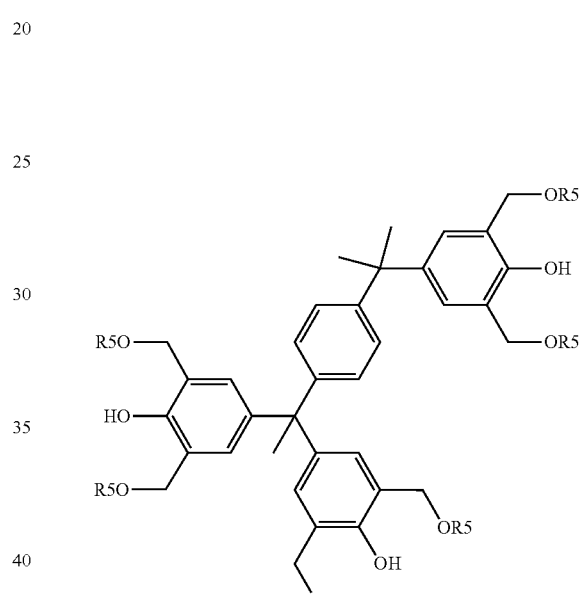
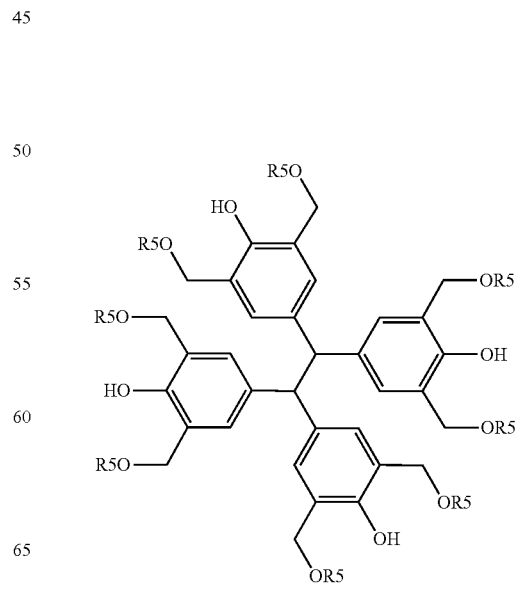

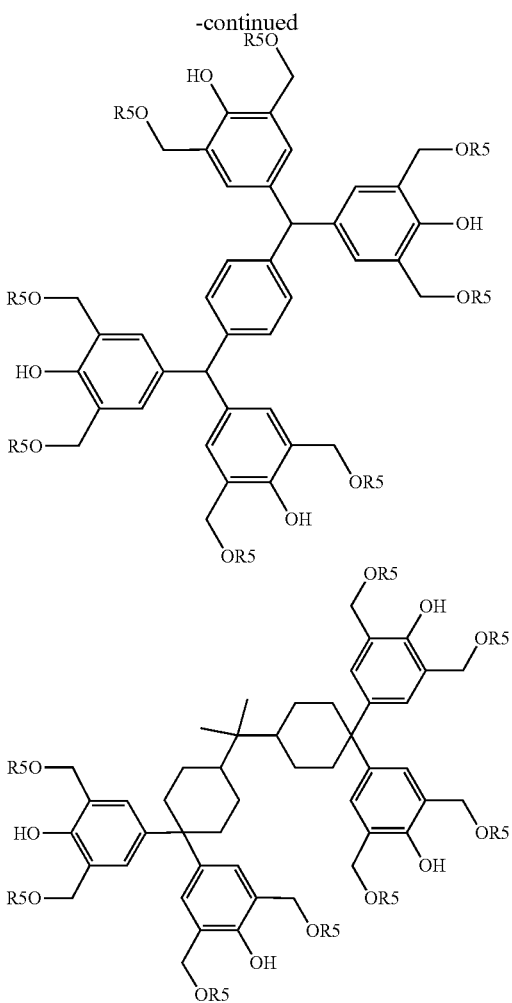

R5 is as defined above.

[(F) Plasticizer]

Further, to the inventive material for forming an organic film, a plasticizer can be added so as to further enhance planarizing and filling properties. The plasticizer is not particularly limited, and known various types of plasticizers can be widely used. Examples thereof can include low-molecular-weight compounds, such as phthalic acid esters, adipic acid esters, phosphoric acid esters, trimellitic acid esters, and citric acid esters; and polymers, such as polyethers, polyesters, and polyacetal-based polymers disclosed in JP 2013-253227 A. When a plasticizer is added, the plasticizer is added in an amount of preferably 1 to 100 parts, more preferably 5 to 30 parts, based on 100 parts of the compound and/or polymer (A).

Further, like the plasticizer, as an additive for imparting the filling and planarizing properties to the inventive material for forming an organic film, it is preferable to use, for example, liquid additives having polyethylene glycol or polypropylene glycol structure, or thermo-decomposable polymers having a weight loss ratio of 40 mass % or more between 30° C. and 250° C. and a weight-average molecular weight of 300 to 200,000. The thermo-decomposable polymers preferably contain a repeating unit having an acetal structure shown by the following general formula (DP1) or (DP1a).

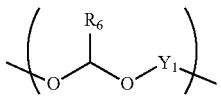
(DP1)

In the formula, $R_6$ represents a hydrogen atom or a saturated or unsaturated monovalent organic group which has 1 to 30 carbon atoms and may be substituted. Yi represents a saturated or unsaturated divalent organic group having 2 to 30 carbon atoms.

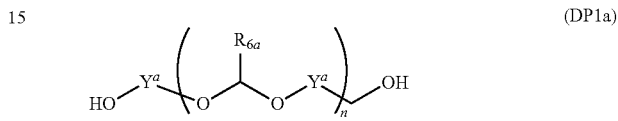
(DP1a)

In the formula, $R_{6a}$ represents an alkyl group having 1 to 4 carbon atoms. $Y^a$ represents a saturated or unsaturated divalent hydrocarbon group which has 4 to 10 carbon atoms and may have an ether bond. "n" represents an average repeating unit number of 3 to 500.

[(G) Other Components]

The inventive material for forming an organic film may be further blended with a different compound or polymer. The blend compound or blend polymer mixed with the inventive material for forming an organic film serves to improve the film formability by spin-coating and/or the filling property for a stepped substrate.

Examples of such materials include novolak resins of phenol, o-cresol, m-cresol, p-cresol, 2,3-dimethylphenol, 2,5-dimethylphenol, 3,4-dimethylphenol, 3,5-dimethylphenol, 2,4-dimethylphenol, 2,6-dimethylphenol, 2,3,5-trimethylphenol, 3,4,5-trimethylphenol, 2-tert-butylphenol, 3-tert-butylphenol, 4-tert-butylphenol, 2-phenylphenol, 3-phenylphenol, 4-phenylphenol, 3,5-diphenylphenol, 2-naphthylphenol, 3-naphthylphenol, 4-naphthylphenol, 4-tritylphenol, resorcinol, 2-methylresorcinol, 4-methylresorcinol, 5-methylresorcinol, catechol, 4-tert-butylcatechol, 2-methoxyphenol, 3-methoxyphenol, 2-propylphenol, 3-propylphenol, 4-propylphenol, 2-isopropylphenol, 3-isopropylphenol, 4-isopropylphenol, 2-methoxy-5-methylphenol, 2-tert-butyl-5-methylphenol, pyrogallol, thymol, isothymol, 4,4'-(9H-fluorene-9-ylidene)bisphenol, 2,2'dimethyl-4,4'-(9H-fluorene-9-ylidene)bisphenol, 2,2'diallyl-4,4'-(9H-fluorene-9-ylidene)bisphenol, 2,2'difluoro-4,4'-(9H-fluorene-9-ylidene)bisphenol, 2,2'diphenyl-4,4'-(9H-fluorene-9-ylidene)bisphenol, 2,2'dimethoxy-4,4'-(9H-fluorene-9-ylidene)bisphenol, 2,3,2',3'-tetrahydro-(1,1')-spirobiindene-6,6'-diol, 3,3,3',3'-tetramethyl-2,3,2',3'-tetrahydro-(1,1')-spirobiindene-6,6'-diol, 3,3,3',3',4,4'-hexamethyl-2,3,2',3'-tetrahydro-(1,1')-spirobiindene-6,6'-diol, 2,3,2',3'-tetrahydro-(1,1')-spirobiindene-5,5'-diol, 5,5'-dimethyl-3,3,3',3'-tetramethyl-2,3,2',3'-tetrahydro-(1,1')-spirobiindene-6,6'-diol, 1-naphthol, 2-naphthol, 2-methyl-1-naphthol, 4-methoxy-1-naphthol, and 7-methoxy-2-naphthol, dihydroxynaphthalenes such as 1,5-dihydroxynaphthalene, 1,7-dihydroxynaphthalene, and 2,6-dihydroxynaphthalene, methyl 3-hydroxynaphthalene-2-carboxylate, indene, hydroxyindene, benzofuran, hydroxyanthracene, acenaphthylene, biphenyl, bisphenol, trisphenol, dicyclopentadiene, tetrahydroindene, 4-vinylcyclohexene, norbornadiene, 5-vinylnorborna-2-ene, α-pinene, β-pinene, limonene, etc.; and polyhydroxystyrene, polystyrene, polyvinylnaphthalene, polyvinylanthracene, polyvinylcarbazole, polyindene, polyacenaphthylene, polynorbornene, polycyclodecene, polytetracyclododecene, polynortricyclene, poly(meth)acrylate, and copolymers thereof. It is also possible to blend a naphthol dicyclopentadiene copolymer disclosed in JP 2004-205685 A, a fluorene bisphenol novolak resin disclosed in JP 2005-128509 A, an acenaphthylene copolymer disclosed in JP 2005-250434 A, fullerene having a phenol group disclosed in JP 2006-227391 A, a bisphenol compound and a novolak resin thereof disclosed in JP 2006-293298 A, a novolak resin of an adamantane phenol compound disclosed in JP 2006-285095 A, a bisnaphthol compound and a novolak resin thereof disclosed in JP 2010-122656 A, a fullerene resin compound disclosed in JP 2008-158002 A, etc.

The blendable compound or blendable polymer is blended in an amount of preferably 0 to 1,000 parts by mass, more preferably 0 to 500 parts by mass, based on 100 parts by mass of the inventive material for forming an organic film.

Note that one kind of the inventive material for forming an organic film can be used, or two or more kinds thereof can be used in combination. The material for forming an organic film can be used as an organic film material or a planarizing material for manufacturing a semiconductor device.

Moreover, the inventive material for forming an organic film is quite useful as an organic film material for multilayer resist processes, such as a two-layer resist process, a three-layer resist process using a silicon-containing underlayer film, and a four-layer resist process using a silicon-containing inorganic hard mask underlayer film and an organic antireflective coating film.

(Method for Forming Organic Film)

The present invention provides a method for forming an organic film by using the above-described material for forming an organic film. The resulting organic film can serve as an organic film in a multilayer resist film used in lithography or a planarizing film for manufacturing a semiconductor.

In the method for forming an organic film by using the inventive material for forming an organic film, a substrate to be processed is coated with the material for forming an organic film by a spin coating method etc. By employing a method like spin coating method, favorable filling property can be obtained. After the spin coating, the solvent is evaporated, and baking (heating) is performed to promote the crosslinking reaction, thereby preventing the mixing with a resist upper layer film or a resist underlayer film. The baking is preferably performed at 100° C. or more and 600° C. or less within 10 to 600 seconds, more preferably at 200° C. or more and 500° C. or less within 10 to 300 seconds. In considering the influences of device damage and wafer deformation, the upper limit of the heating temperature in lithographic wafer process is preferably 600° C. or less, more preferably 500° C. or less.

Moreover, in the method for forming an organic film by using the inventive material for forming an organic film, after a substrate to be processed is coated with the inventive material for forming an organic film by the spin coating method or the like as described above, an organic film can be formed by curing the material for forming an organic film by baking in an atmosphere with an oxygen concentration of 0.1% or more and 21% or less.

A sufficiently cured film can be obtained by baking the inventive material for forming an organic film in such an oxygen atmosphere. The atmosphere during the baking may be in air. Nevertheless, it is preferable to introduce an inert gas such as N2, Ar, or He to reduce oxygen amount from the viewpoint of preventing oxidation of the organic film. To prevent the oxidation, the oxygen concentration needs to be controlled, and is preferably 1000 ppm or less, more preferably 100 ppm or less. Preventing the oxidation of the organic film during baking is preferable because an increase in absorption and a decrease in etching resistance are prevented.

Such a method for forming an organic film by using the inventive material for forming an organic film makes it possible to obtain a flat cured film regardless of unevenness of a substrate to be processed, because of the excellent filling and planarizing properties. Accordingly, the method is quite useful in forming a flat cured film on a substrate to be processed which has a structure or step with a height of 30 nm or more.

Note that the thickness of the organic film such as a planarizing film for manufacturing a semiconductor device is appropriately determined and preferably 30 to 20,000 nm, particularly preferably 50 to 15,000 nm.

(Patterning Processes)

The present invention provides a patterning process according to a three-layer resist process using such a material for forming an organic film as described above. The patterning process is a patterning process for forming a pattern in a substrate to be processed, and includes at least:

forming an organic film by using the inventive material for forming an organic film on a substrate to be processed;

forming a silicon-containing resist underlayer film by using a resist underlayer film material containing silicon atoms on the organic film;

forming a resist upper layer film by using a photoresist composition as a resist upper layer film material on the silicon-containing resist underlayer film, so that a multilayer resist film is formed;

subjecting a pattern circuit region of the resist upper layer film to exposure and then development with a developer to form a resist pattern in the resist upper layer film;

transferring the pattern to the silicon-containing resist underlayer film by etching while using the obtained resist pattern as an etching mask;

transferring the pattern to the organic film by etching while using the obtained pattern in the silicon-containing resist underlayer film as an etching mask; and further transferring the pattern to the substrate to be processed by etching while using the obtained organic film pattern as an etching mask.

The silicon-containing resist underlayer film in this three-layer resist process exhibits resistance to etching with an oxygen gas or a hydrogen gas. Hence, when the organic film is dry-etched using the silicon-containing resist underlayer film as a mask in the three-layer resist process, the dry etching is performed preferably with an etching gas mainly containing an oxygen gas or a hydrogen gas.

As the silicon-containing resist underlayer film in the three-layer resist process, a polysiloxane-based underlayer film is also preferably used. The silicon-containing resist underlayer film having antireflective effect can suppress the reflection. Particularly, for 193-nm light exposure, a material containing many aromatic groups and having high etching selectivity relative to the substrate is used as an organic film, so that the k-value and thus the substrate reflection are increased. Meanwhile, the reflection can be suppressed by imparting absorption to the silicon-containing resist underlayer film so as to have an appropriate k-value, and the substrate reflection can be reduced to 0.5% or less. As the silicon-containing resist underlayer film having antireflective effect, a polysiloxane is preferably used which has anthracene for 248-nm and 157-nm light exposure, or a phenyl group or a light-absorbing group having a silicon-silicon bond for 193-nm light exposure in a pendant structure, and which is crosslinked by an acid or heat.

Moreover, the present invention is suitable for a four-layer resist process using an organic antireflective coating film. In this case, a semiconductor-device circuit pattern can be formed in a substrate by a patterning process including at least:

forming an organic film by using the inventive material for forming an organic film on a substrate to be processed;

forming a silicon-containing resist underlayer film by using a silicon-containing resist underlayer film material on the organic film;

forming an organic antireflective coating film on the silicon-containing resist underlayer film;

forming a resist upper layer film by using a photoresist composition as a resist upper layer film material on the organic antireflective coating film, so that a multilayer resist film is formed;

subjecting a pattern circuit region of the resist upper layer film to exposure and then development with a developer to form a resist pattern in the resist upper layer film;

transferring the pattern to the organic antireflective coating film and the silicon-containing resist underlayer film by etching while using the obtained resist pattern as an etching mask;

transferring the pattern to the organic film by etching while using the obtained pattern in the silicon-containing resist underlayer film as an etching mask; and further transferring the pattern to the substrate to be processed by etching the substrate to be processed while using the obtained organic film pattern as an etching mask.

Alternatively, an inorganic hard mask may be formed instead of the silicon-containing resist underlayer film. In this case, a semiconductor-device circuit pattern can be formed in a substrate by a patterning process including at least:

forming an organic film by using the inventive material for forming an organic film on a substrate to be processed;

forming an inorganic hard mask selected from a silicon oxide film, a silicon nitride film, and a silicon oxynitride film on the organic film;

forming a resist upper layer film by using a photoresist composition as a resist upper layer film material on the inorganic hard mask;

subjecting a pattern circuit region of the resist upper layer film to exposure and then development with a developer to form a resist pattern in the resist upper layer film;

transferring the pattern to the inorganic hard mask by etching while using the obtained resist pattern as an etching mask;

transferring the pattern to the organic film by etching while using the obtained inorganic hard mask pattern as an etching mask; and further transferring the pattern to the substrate to be processed by etching while using the obtained organic film pattern as an etching mask.

As described above, when an inorganic hard mask is formed on an organic film, a silicon oxide film, a silicon nitride film, and a silicon oxynitride film (SiON film) can be formed by a CVD method, an ALD method, etc. The method for forming a silicon nitride film is described, for example, in JP 2002-334869 A and WO 2004/066377 A1. The film thickness of the inorganic hard mask is preferably 5 to 200 nm, more preferably 10 to 100 nm. As the inorganic hard mask, a SiON film is most preferably used which is effective as an antireflective film. When the SiON film is formed, the substrate temperature reaches 300 to 500° C. Hence, the organic film needs to withstand the temperature of 300 to 500° C. Since the material for forming an organic film used in the present invention has high heat resistance and can withstand high temperatures of 300° C. to 500° C., this enables the combination of the inorganic hard mask formed by a CVD method or an ALD method with the organic film formed by a spin coating method.

Furthermore, the present invention is suitable for a four-layer resist process using an organic antireflective coating film. In this case, a semiconductor-device circuit pattern can be formed in a substrate by a patterning process including at least:

forming an organic film by using the inventive material for forming an organic film on a substrate to be processed;

forming an inorganic hard mask selected from a silicon oxide film, a silicon nitride film, and a silicon oxynitride film on the organic film;

forming an organic antireflective coating film on the inorganic hard mask;

forming a resist upper layer film by using a photoresist composition as a resist upper layer film material on the organic antireflective coating film, so that a multilayer resist film is formed;

subjecting a pattern circuit region of the resist upper layer film to exposure and then development with a developer to form a resist pattern in the resist upper layer film;

transferring the pattern to the organic antireflective coating film and the inorganic hard mask by etching while using the obtained resist pattern as an etching mask;

transferring the pattern to the organic film by etching while using the obtained inorganic hard mask pattern as an etching mask; and further transferring the pattern to the substrate to be processed by etching while using the obtained organic film pattern as an etching mask.

Although a photoresist film may be formed as a resist upper layer film on an inorganic hard mask, it is also possible to form an organic antireflective coating film (BARC) on the inorganic hard mask by spin coating and then form the photoresist film on the BARC as described above. Particularly, when a SiON film is used as the inorganic hard mask, two antireflective films including the SiON film and the BARC make it possible to suppress the reflection even in immersion exposure at a high NA exceeding 1.0. Another merit of the BARC formation is having an effect of reducing footing of the photoresist pattern immediately above the SiON film.

The resist upper layer film in the 3-layer resist process may be a positive type or a negative type, and generally-used photoresist compositions can be employed. After spin-coating of the photoresist composition, pre-baking is performed preferably at 60 to 180° C. for 10 to 300 seconds. Then, light exposure, post-exposure bake (PEB), and development are performed according to conventional methods to obtain the resist pattern. Note that the thickness of the resist upper layer film is not particularly limited, but is preferably 30 to 500 nm, and 50 to 400 nm is particularly preferable.

Additionally, examples of exposure light can include a high-energy beam with a wavelength of 300 nm or less, specifically, excimer laser of 248 nm, 193 nm, and 157 nm, soft X-ray of 3 to 20 nm, electron beam, X-ray, etc.

A pattern is formed in the resist upper layer film by a method of preferably a photolithography with a wavelength of 10 nm or more and 300 nm or less, a direct drawing with electron beam, nanoimprinting, or a combination thereof.

Moreover, as the development method in the patterning processes, alkaline development or organic solvent development is preferably employed.

Next, etching is performed using the obtained resist pattern as a mask. In the three-layer resist process, the silicon-containing resist underlayer film or the inorganic hard mask can be etched using a fluorocarbon-based gas and using the upper layer resist pattern as the mask. Thereby, a silicon-containing resist underlayer film pattern or an inorganic hard mask pattern is formed.

Next, using the obtained silicon-containing resist underlayer film pattern or inorganic hard mask pattern as a mask, the organic film is processed by etching.

Subsequently, the substrate to be processed can be etched according to a conventional method. For example, the substrate to be processed made of $SiO_2$, SiN, or silica low-dielectric insulating film is etched mainly with a fluorocarbon-based gas; and the substrate to be processed made of p-Si, Al, or W is etched mainly with a chlorine- or bromine-based gas. When the substrate is processed by etching with a fluorocarbon-based gas, the silicon-containing resist underlayer film pattern in the three-layer resist process is removed when the substrate is processed. Meanwhile, when the substrate is etched with a chlorine- or bromine-based gas, the silicon-containing resist underlayer film pattern needs to be removed by additional dry etching with a fluorocarbon-based gas after the substrate processing.

The organic film obtained from the inventive material for forming an organic film is characterized by excellent etching resistance when the substrate to be processed is etched as described above.

Note that the substrate to be processed is not particularly limited, and examples thereof include: substrates made of Si, a-Si, p-Si, $SiO_2$, SiN, SiON, W, TiN, Al, or the like; these substrates coated with a layer to be processed; etc. Examples of the layer to be processed include: various Low-k films made of Si, $SiO_2$, SiON, SiN, p-Si, a-Si, W, W—Si, Al, Cu, Al—Si, or the like; and stopper films thereof. The layer can be formed to have a thickness of generally 50 to 10,000 nm, particularly 100 to 5,000 nm. Note that when the layer to be processed is formed, the substrate and the layer to be processed are formed from different materials.

As the substrate to be processed, it is preferable to use a semiconductor device substrate or the semiconductor device substrate coated with any of a metal film, a metal carbide film, a metal oxide film, a metal nitride film, a metal oxycarbide film, and a metal oxynitride film. More specifically, although the substrate to be processed is not particularly limited, examples thereof include substrates made of Si, a-Si, p-Si, $SiO_2$, SiN, SiON, W, TiN, Al, or the like; these substrates coated with any film of the aforementioned metal films, or the like as a layer to be processed; etc.

Examples of the layer to be processed include various Low-k films made of Si, $SiO_2$, SiON, SiN, p-Si, a-Si, W, W—Si, Al, Cu, Al—Si, or the like; and stopper films thereof. The layer can be formed to have a thickness of generally 50 to 10,000 nm, particularly 100 to 5,000 nm. Note that when the layer to be processed is formed, the substrate and the layer to be processed are formed from different materials.

Note that the metal constituting the substrate to be processed is preferably silicon, titanium, tungsten, hafnium, zirconium, chromium, germanium, copper, silver, gold, aluminum, indium, gallium, arsenic, palladium, iron, tantalum, iridium, cobalt, manganese, molybdenum, ruthenium, or an alloy thereof.

Moreover, as the substrate to be processed, it is preferable to use a substrate to be processed which has a structure or step with a height of 30 nm or more.

Hereinbelow, an example of the three-layer resist process will be specifically described with reference to FIG. 1. As shown in FIG. 1 (A), in the three-layer resist process, an organic film 3 is formed by using the inventive material for forming an organic film on a layer 2 to be processed that has been stacked on a substrate 1. Then, a silicon-containing resist underlayer film 4 is formed, and a resist upper layer film 5 is formed thereon.

Next, as shown in FIG. 1 (B), a predetermined portion 6 of the resist upper layer film 5 is exposed to light, followed by PEB and development to form a resist pattern 5a (FIG. 1 (C)). While using the obtained resist pattern 5a as a mask, the silicon-containing resist underlayer film 4 is etched with a CF-based gas. Thereby, a silicon-containing resist underlayer film pattern 4a is formed (FIG. 1 (D)). After the resist pattern 5a is removed, the organic film 3 is etched with oxygen plasma while using the obtained silicon-containing resist underlayer film pattern 4a as a mask. Thereby, an organic film pattern 3a is formed (FIG. 1 (E)). Further, after the silicon-containing resist underlayer film pattern 4a is removed, the layer 2 to be processed is etched while using the organic film pattern 3a as a mask. Thus, a pattern 2a is formed (FIG. 1 (F))

When an inorganic hard mask is used, the inorganic hard mask is formed in place of the silicon-containing resist underlayer film 4. When a BARC is formed, the BARC layer is provided between the silicon-containing resist underlayer film 4 and the resist upper layer film 5. The etching of the BARC starts before the etching of the silicon-containing resist underlayer film 4, but these etchings may be performed continuously. Alternatively, after the BARC is etched alone, the etching apparatus is changed, for example, and then the silicon-containing resist underlayer film 4 may be etched.

As described above, the inventive patterning processes make it possible to precisely form a fine pattern in a substrate to be processed in multilayer resist processes.

EXAMPLE

Hereinafter, the present invention will be more specifically described with reference to Synthesis Examples, Examples, and Comparative Examples. Nevertheless, the present invention is not limited thereto. Note that regarding molecular weight and dispersity, gel permeation chromatography (GPC) was performed using tetrahydrofuran as an eluent to determine weight-average molecular weight (Mw) and number-average molecular weight (Mn) in terms of polystyrene, and dispersity (Mw/Mn) was obtained therefrom.

Synthesis Examples: Synthesis of Compounds and Polymers for Organic Film Material Compounds (A1) to (A7) for organic film materials as well as Compound (R1) for Comparative Examples were synthesized using the following Phenols (B1) to (B5) and Fluorenols (C1) to (C4).

Phenols:

(B1) 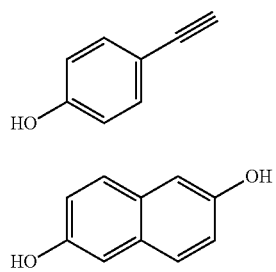

(B2) 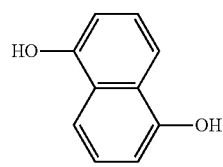

(B3) 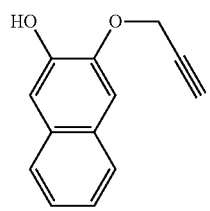

(B4) 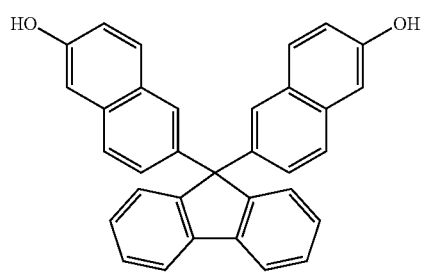

(B5) 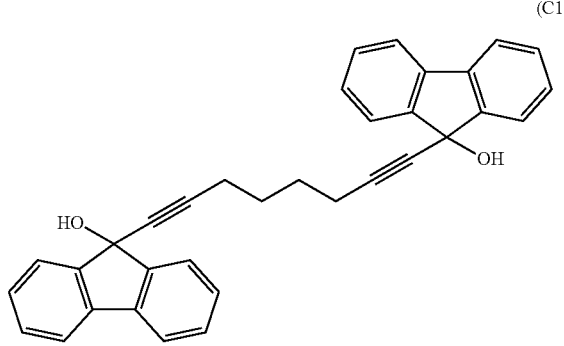

Fluorenols:

(C1)

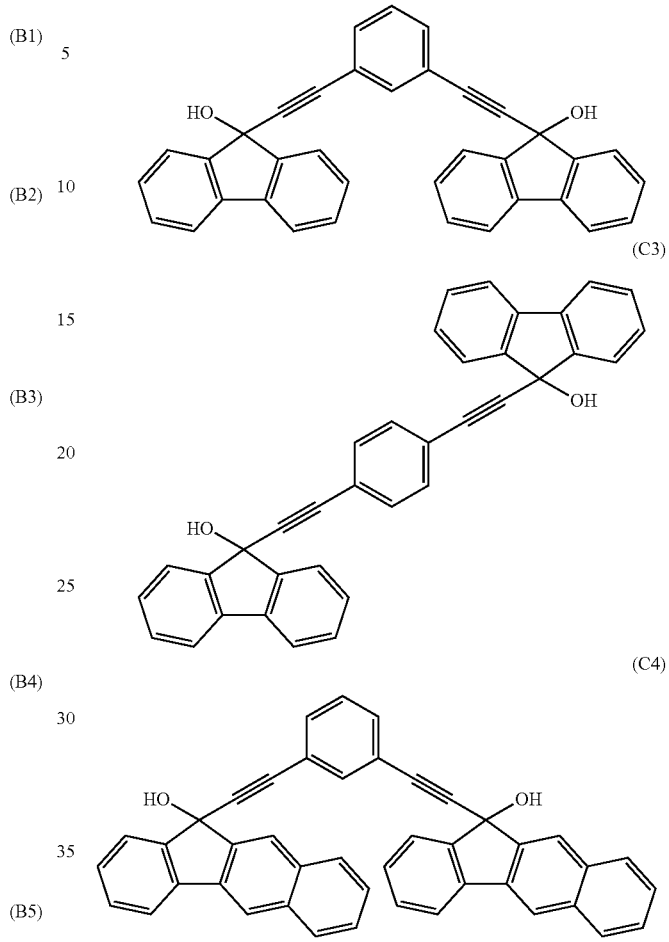

(C2)

(C3)

(C4)

Synthesis Example 1

Synthesis of Compound (A1)

(A1)

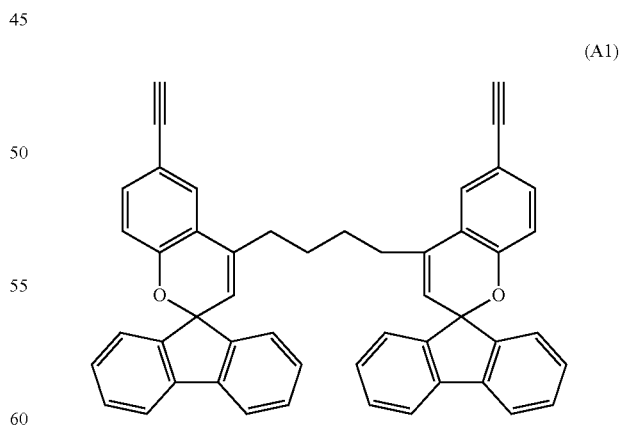

Under nitrogen atmosphere, 22.8 g of Phenol (B1), 30.0 g of Fluorenol (C1), and 200 g of 1,2-dichloroethane were added together to prepare a homogeneous dispersion with an inner temperature of 50° C. Then, 15.4 g of methanesulfonic acid was slowly added thereto, and the reaction was allowed to proceed with the inner temperature of 50° C. for 6 hours.

After completion of the reaction, the resultant was cooled to room temperature, mixed with 400 ml of MIBK (methyl isobutyl ketone), and washed six times with 100 ml of pure water. The organic layer was dried under reduced pressure. To the residue, 150 g of THE was added and a homogeneous solution was prepared. Subsequently, a crystal was precipitated with 500 g of methanol. The precipitated crystal was separated by filtration, washed twice with 200 g of methanol, and collected. The collected crystal was vacuum dried at 70° C. Thus, Compound (A1) was obtained.

When the weight-average molecular weight (Mw) and dispersity (Mw/Mn) were determined by GPC, the following results were obtained.

(A1): Mw=720, Mw/Mn=1.04

Synthesis Example 2

Synthesis of Compound (A2)

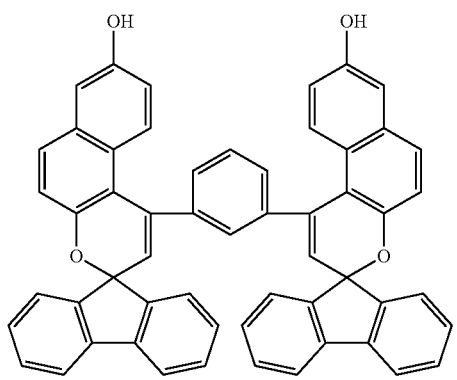

(A2)

Under nitrogen atmosphere, 32.9 g of Phenol (B2), 20.0 g of Fluorenol (C2), and 200 g of 1,2-dichloroethane were added together to prepare a homogeneous dispersion with an inner temperature of 50° C. Then, 9.9 g of methanesulfonic acid was slowly added thereto, and the reaction was allowed to proceed with the inner temperature of 50° C. for 6 hours. After completion of the reaction, the resultant was cooled to room temperature, mixed with 400 ml of MIBK, and washed six times with 100 ml of pure water. The organic layer was dried under reduced pressure. To the residue, 150 g of THE was added and a homogeneous solution was prepared. Subsequently, a crystal was precipitated with 500 g of IPE (diisopropyl ether). The precipitated crystal was separated by filtration, washed twice with 300 g of methanol, and collected. The collected crystal was vacuum dried at 70° C. Thus, Compound (A2) was obtained. When the weight-average molecular weight (Mw) and dispersity (Mw/Mn) were determined by GPC, the following results were obtained.

(A2): Mw=840, Mw/Mn=1.06

Synthesis Example 3

Synthesis of Compound (A3)

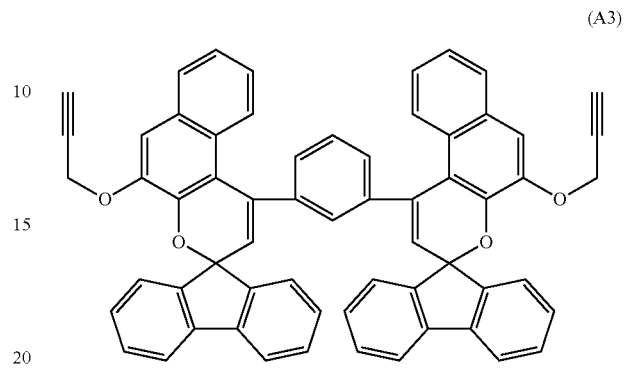

(A3)

Under nitrogen atmosphere, 24.4 g of Phenol (B4), 20.0 g of Fluorenol (C2), and 200 g of 1,2-dichloroethane were added together to prepare a homogeneous dispersion with an inner temperature of 50° C. Then, 9.9 g of methanesulfonic acid was slowly added thereto, and the reaction was allowed to proceed with the inner temperature of 50° C. for 6 hours. After completion of the reaction, the resultant was cooled to room temperature, mixed with 350 ml of MIBK, and washed six times with 100 ml of pure water. The organic layer was dried under reduced pressure. To the residue, 180 g of THF was added and a homogeneous solution was prepared. Subsequently, a crystal was precipitated with 500 g of methanol. The precipitated crystal was separated by filtration, washed twice with 200 g of methanol, and collected. The collected crystal was vacuum dried at 70° C. Thus, Compound (A3) was obtained. When the weight-average molecular weight (Mw) and dispersity (Mw/Mn) were determined by GPC, the following results were obtained.

(A3): Mw=890, Mw/Mn=1.04

Synthesis Example 4

Synthesis of Compound (A4)

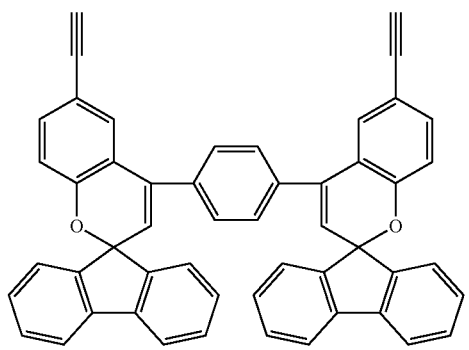

(A4)

Under nitrogen atmosphere, 21.9 g of Phenol (B1), 30.0 g of Fluorenol (C3), and 100 g of 1,2-dichloroethane were added together to prepare a homogeneous dispersion with an inner temperature of 50° C. Then, 14.8 g of methanesulfonic acid was slowly added thereto, and the reaction was allowed to proceed with the inner temperature of 50° C. for 6 hours. After completion of the reaction, the resultant was cooled to room temperature, mixed with 400 ml of MIBK, and washed six times with 100 ml of pure water. The organic layer was dried under reduced pressure. To the residue, 200 g of THF was added and a homogeneous solution was prepared. Subsequently, a crystal was precipitated with 500 g of methanol. The precipitated crystal was separated by filtration, washed twice with 200 g of methanol, and collected. The collected crystal was vacuum dried at 70° C. Thus, Compound (A4) was obtained.

When the weight-average molecular weight (Mw) and dispersity (Mw/Mn) were determined by GPC, the following results were obtained.
(A4): Mw=710, Mw/Mn=1.03

Synthesis Example 5

Synthesis of Compound (A5)

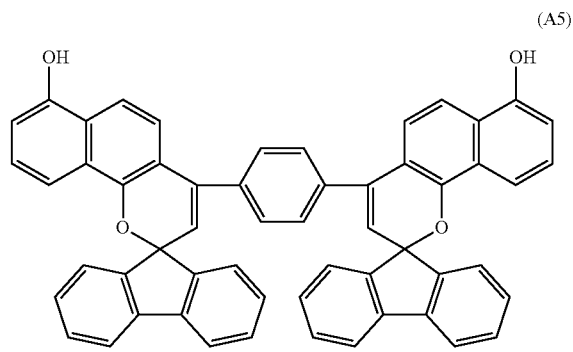 [SMILES: Oc1cccc2c3c(ccc12)C(c1ccc(C2=CC4(Oc5c2ccc2c(O)cccc52)c2ccccc2-c2ccccc24)cc1)=CC1(O3)c2ccccc2-c2ccccc21]
(A5)

Under nitrogen atmosphere, 32.9 g of Phenol (B3), 20.0 g of Fluorenol (C3), and 100 g of 1,2-dichloroethane were added together to prepare a homogeneous dispersion with an inner temperature of 50° C. Then, 9.9 g of methanesulfonic acid was slowly added thereto, and the reaction was allowed to proceed with the inner temperature of 50° C. for 6 hours. After completion of the reaction, the resultant was cooled to room temperature, mixed with 400 ml of MIBK, and washed six times with 100 ml of pure water. The organic layer was dried under reduced pressure. To the residue, 100 g of THE was added and a homogeneous solution was prepared. Subsequently, a crystal was precipitated with 500 g of IPE. The precipitated crystal was separated by filtration, washed twice with 200 g of methanol, and collected. The collected crystal was vacuum dried at 70° C. Thus, Compound (A5) was obtained.

When the weight-average molecular weight (Mw) and dispersity (Mw/Mn) were determined by GPC, the following results were obtained.
(A5): Mw=900, Mw/Mn=1.06

Synthesis Example 6

Synthesis of Compound (A6)

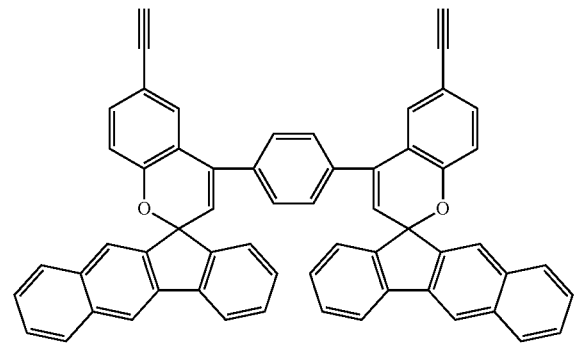
(A6)

Under nitrogen atmosphere, 18.1 g of Phenol (B1), 30.0 g of Fluorenol (C4), and 100 g of 1,2-dichloroethane were added together to prepare a homogeneous dispersion with an inner temperature of 50° C. Then, 12.3 g of methanesulfonic acid was slowly added thereto, and the reaction was allowed to proceed with the inner temperature of 50° C. for 6 hours. After completion of the reaction, the resultant was cooled to room temperature, mixed with 400 ml of MIBK, and washed six times with 100 ml of pure water. The organic layer was dried under reduced pressure. To the residue, 200 g of THE was added and a homogeneous solution was prepared. Subsequently, a crystal was precipitated with 500 g of methanol. The precipitated crystal was separated by filtration, washed twice with 200 g of methanol, and collected. The collected crystal was vacuum dried at 70° C. Thus, Compound (A6) was obtained.

When the weight-average molecular weight (Mw) and dispersity (Mw/Mn) were determined by GPC, the following results were obtained.
(A6): Mw=850, Mw/Mn=1.05

Synthesis Example 7

Synthesis of Compound (A7)

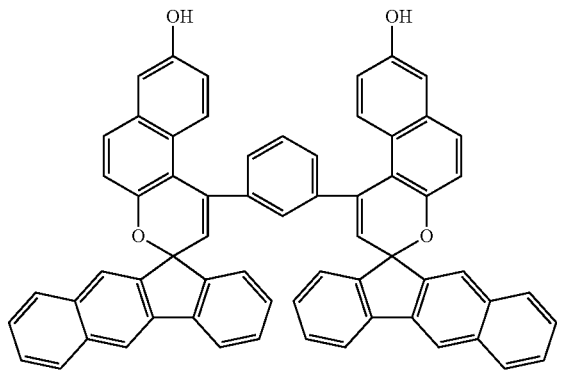
(A7)

Under nitrogen atmosphere, 27.3 g of Phenol (B2), 20.0 g of Fluorenol (C4), and 200 g of 1,2-dichloroethane were added together to prepare a homogeneous dispersion with an inner temperature of 50° C. Then, 8.2 g of methanesulfonic acid was slowly added thereto, and the reaction was allowed to proceed with the inner temperature of 50° C. for 6 hours. After completion of the reaction, the resultant was cooled to room temperature, mixed with 400 ml of MIBK, and washed six times with 100 ml of pure water. The organic layer was dried under reduced pressure. To the residue, 200 g of THE was added and a homogeneous solution was prepared. Subsequently, a crystal was precipitated with 500 g of IPE. The precipitated crystal was separated by filtration, washed twice with 200 g of methanol, and collected. The collected crystal was vacuum dried at 70° C. Thus, Compound (A7) was obtained.

When the weight-average molecular weight (Mw) and dispersity (Mw/Mn) were determined by GPC, the following results were obtained.

(A7): Mw=950, Mw/Mn=1.07

Synthesis Example 8

Synthesis of Polymer (A8)

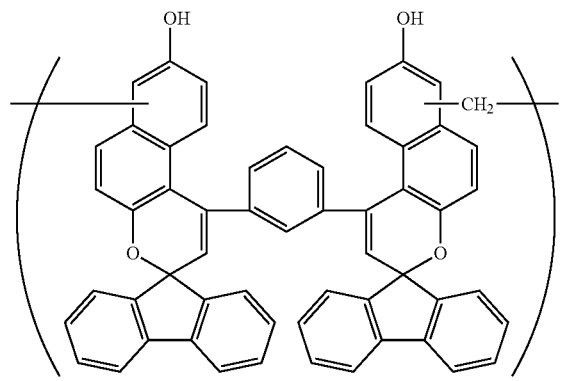

(A8)

Under nitrogen atmosphere, 20.0 g of Compound (A2), 1.47 g of a 37% formalin aqueous solution, and 100 g of 1,2-dichloroethane were added together to prepare a homogeneous solution with an inner temperature of 50° C. Then, 2.5 g of methanesulfonic acid was slowly added thereto, and the reaction was allowed to proceed with the inner temperature of 50° C. for 8 hours. After completion of the reaction, the resultant was cooled to room temperature, mixed with 300 ml of MIBK, and washed six times with 100 ml of pure water. The organic layer was dried under reduced pressure. To the residue, 100 g of THE was added and a homogeneous solution was prepared. Subsequently, a crystal was precipitated with 300 g of hexane. The precipitated crystal was separated by filtration, washed twice with 200 g of hexane, and collected. The collected crystal was vacuum dried at 70° C. Thus, Polymer (A8) was obtained.

When the weight-average molecular weight (Mw) and dispersity (Mw/Mn) were determined by GPC, the following results were obtained.

(A8): Mw=3300, Mw/Mn=1.68

Synthesis Example 9

Synthesis of Polymer (A9)

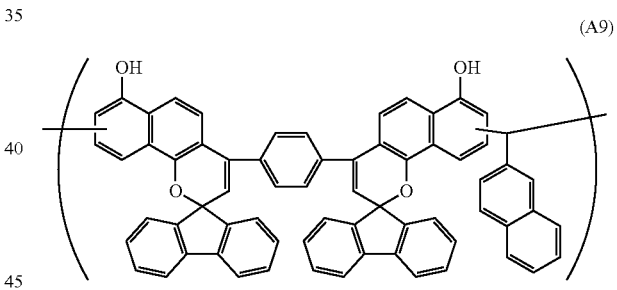

(A9)

Under nitrogen atmosphere, 20.0 g of Compound (A5), 2.84 g of 2-naphthoaldehyde, and 100 g of 1,2-dichloroethane were added together to prepare a homogeneous solution with an inner temperature of 50° C. Then, 2.5 g of methanesulfonic acid was slowly added thereto, and the reaction was allowed to proceed with the inner temperature of 50° C. for 8 hours. After completion of the reaction, the resultant was cooled to room temperature, mixed with 300 ml of MIBK, and washed six times with 100 ml of pure water. The organic layer was dried under reduced pressure. To the residue, 100 g of THE was added and a homogeneous solution was prepared. Subsequently, a crystal was precipitated with 300 g of hexane. The precipitated crystal was separated by filtration, washed twice with 200 g of hexane, and collected. The collected crystal was vacuum dried at 70° C. Thus, Polymer (A9) was obtained.

When the weight-average molecular weight (Mw) and dispersity (Mw/Mn) were determined by GPC, the following results were obtained.

(A9): Mw=3400, Mw/Mn=1.76

Synthesis Example 10

Synthesis of Polymer (A10)

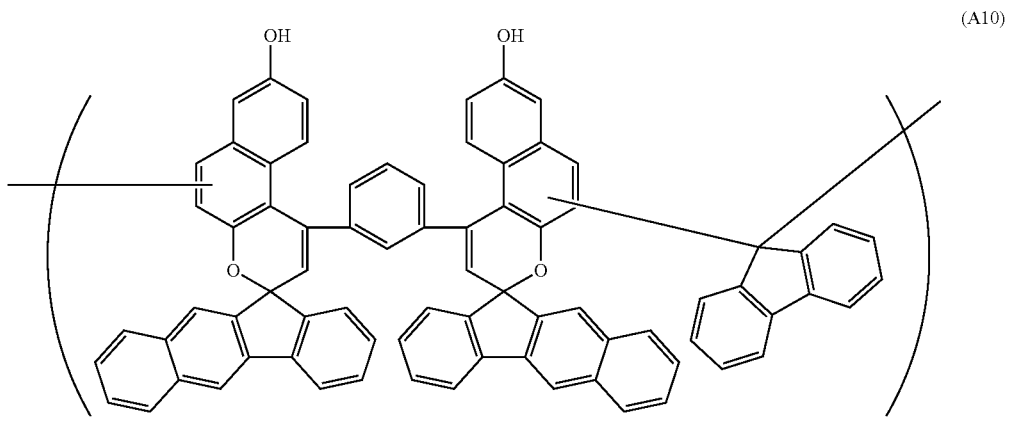

Under nitrogen atmosphere, 20.0 g of Compound (A7), 3.31 g of 9-fluorenone, and 100 g of 1,2-dichloroethane were added together to prepare a homogeneous dispersion with an inner temperature of 50° C. Then, a mixture solution prepared in advance from 2.2 g of methanesulfonic acid and 0.73 g of 3-mercaptopropionic acid was slowly added thereto, and the reaction was allowed to proceed with the inner temperature of 70° C. for 12 hours. After completion of the reaction, the resultant was cooled to room temperature, mixed with 300 ml of MIBK, and washed six times with 100 ml of pure water. The organic layer was dried under reduced pressure. To the residue, 100 g of THF was added and a homogeneous solution was prepared. Subsequently, a crystal was precipitated with 300 g of IPE. The precipitated crystal was separated by filtration, washed twice with 200 g of IPE, and collected. The collected crystal was vacuum dried at 70° C. Thus, Polymer (A10) was obtained.

When the weight-average molecular weight (Mw) and dispersity (Mw/Mn) were determined by GPC, the following results were obtained.

(A10): Mw=4300, Mw/Mn=1.86

Synthesis Example 11

Synthesis of Polymer (A11)

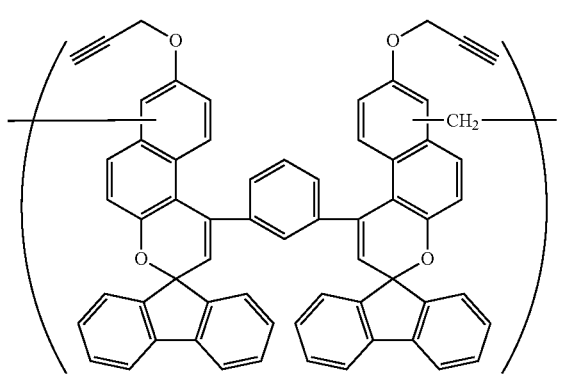

Under nitrogen atmosphere, 10.0 g of Polymer (A8), 7.1 g of potassium carbonate, and 50 g of dimethylformamide were added together to prepare a homogeneous dispersion with an inner temperature of 50° C. Then, 4.6 g of propargyl bromide was slowly added thereto, and the reaction was allowed to proceed with the inner temperature of 50° C. for 24 hours. After completion of the reaction, the resultant was cooled to room temperature, mixed with 200 ml of MIBK, and washed six times with 100 ml of pure water. The organic layer was dried under reduced pressure. To the reaction solution, 200 ml of methyl isobutyl ketone and 100 g of pure water were added to dissolve deposited salt. Thereafter, the separated aqueous layer was removed. Further, after the organic layer was washed twice with 50 g of a 3% nitric acid aqueous solution and six times with 50 g of pure water, the organic layer was dried under reduced pressure. To the residue, 40 g of THF was added and a homogeneous solution was prepared. Subsequently, a crystal was precipitated with 150 g of methanol. The precipitated crystal was separated by filtration, washed twice with 100 g of methanol, and collected. The collected crystal was vacuum dried at 70° C. Thus, Polymer (A11) was obtained.

When the weight-average molecular weight (Mw) and dispersity (Mw/Mn) were determined by GPC, the following results were obtained.

(A11): Mw=3700, Mw/Mn=1.73

Synthesis Example 12

Synthesis of Polymer (A12)

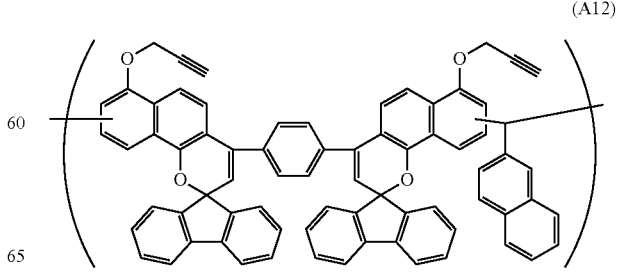

Under nitrogen atmosphere, 10.0 g of Polymer (A9), 6.1 g of potassium carbonate, and 50 g of dimethylformamide were added together to prepare a homogeneous dispersion with an inner temperature of 50° C. Then, 3.9 g of propargyl bromide was slowly added thereto, and the reaction was allowed to proceed with the inner temperature of 50° C. for 24 hours. After completion of the reaction, the resultant was cooled to room temperature, mixed with 200 ml of MIBK, and washed six times with 100 ml of pure water. The organic layer was dried under reduced pressure. To the reaction solution, 200 ml of methyl isobutyl ketone and 100 g of pure water were added to dissolve deposited salt. Thereafter, the separated aqueous layer was removed. Further, after the organic layer was washed twice with 50 g of a 3% nitric acid aqueous solution and six times with 50 g of pure water, the organic layer was dried under reduced pressure. To the residue, 40 g of THF was added and a homogeneous solution was prepared. Subsequently, a crystal was precipitated with 150 g of methanol. The precipitated crystal was separated by filtration, washed twice with 100 g of methanol, and collected. The collected crystal was vacuum dried at 70° C. Thus, Polymer (A12) was obtained.

When the weight-average molecular weight (Mw) and dispersity (Mw/Mn) were determined by GPC, the following results were obtained.
(A12): Mw=3800, Mw/Mn=1.85

Synthesis Example 13

Synthesis of Compound (R1) for Comparative Examples

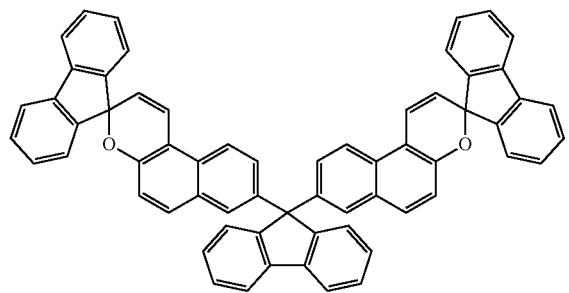

(R1)

Under nitrogen atmosphere, a homogeneous solution with a liquid temperature of 80° C. was prepared from 10.0 g of Phenol (B5), which is a diol compound, 13.8 g of 9-ethynyl-9-fluorenol, 14.1 g of trimethyl orthoformate, and 250 g of 1,2-dichloroethane. Then, 3.4 g of pyridinium p-toluenesulfonate was added thereto, and the reaction was allowed to proceed with the liquid temperature of 80° C. for 12 hours. The resultant was cooled to room temperature and then mixed with 300 ml of MIBK. After the organic layer was washed five times with 100 g of pure water, the organic layer was dried under reduced pressure. To the residue, 50 g of THF was added and a homogeneous solution was prepared. Subsequently, a crystal was deposited with 200 g of methanol. The precipitated crystal was separated by filtration and dried under reduced pressure. Thus, Compound (R1) was obtained.

When the weight-average molecular weight (Mw) and dispersity (Mw/Mn) were determined by GPC, the following results were obtained.
(R1): Mw=900, Mw/Mn=1.04

Synthesis Example 14

Synthesis of Compound (R2) for Comparative Examples

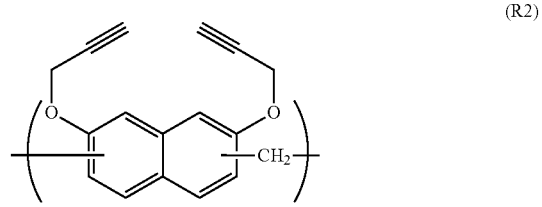

(R2)

Under nitrogen atmosphere, a homogeneous solution with a liquid temperature of 70° C. was prepared from 80 g of 2,7-dipropargyloxynaphthalene, 22 g of a 37% formalin solution, and 250 g of 1,2-dichloroethane. Then, 5 g of methanesulfonic acid was slowly added thereto, and the reaction was allowed to proceed with the liquid temperature of 80° C. for 12 hours. The resultant was cooled to room temperature and then mixed with 500 ml of MIBK. After the organic layer was washed five times with 200 g of pure water, the organic layer was dried under reduced pressure. To the residue, 300 g of THF was added and a homogeneous solution was prepared. Subsequently, the polymer was reprecipitated with 2000 g of hexane. The precipitated polymer was separated by filtration and dried under reduced pressure. Thus, Compound (R2) was obtained.

When the weight-average molecular weight (Mw) and dispersity (Mw/Mn) were determined by GPC, the following results were obtained.
(R2): Mw=2900, Mw/Mn=1.57

Tables 1 to 4 list the results of Mw and Mw/Mn of Compounds and Polymers (A1) to (A12) used in Examples and Compounds (R1) and (R2) used in Comparative Examples.

TABLE 1

| Synthesis Example | Product | Mw | Mw/Mn |
|---|---|---|---|
| 1 | | 720 | 1.04 |

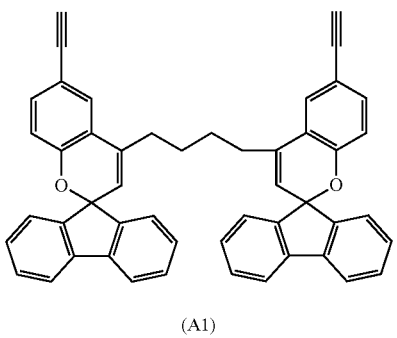

(A1)

TABLE 1-continued
| Synthesis Example | Product | Mw | Mw/Mn |
|---|---|---|---|
| 2 | (A2) 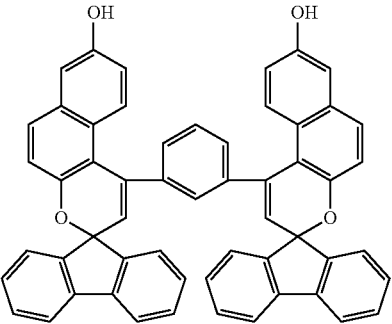 | 840 | 1.06 |
| 3 | (A3) 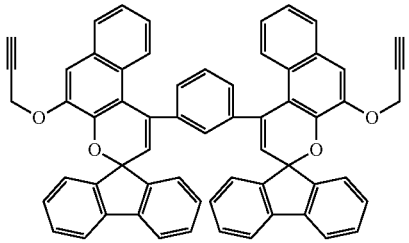 | 890 | 1.04 |
| 4 | (A4) 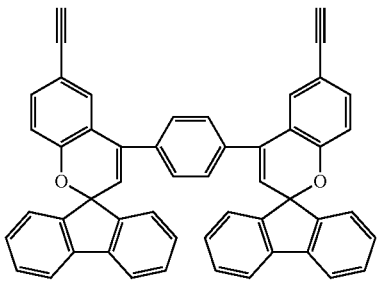 | 710 | 1.03 |
TABLE 2
| Synthesis Example | Product | Mw | Mw/Mn |
|---|---|---|---|
| 5 | (A5) 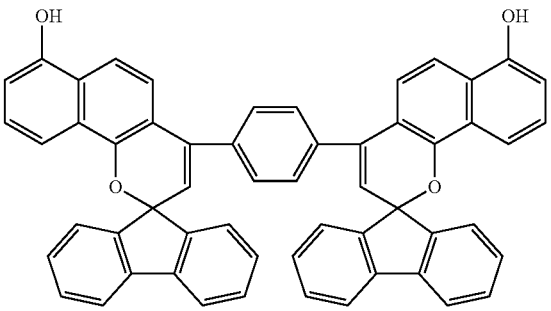 | 900 | 1.06 |
| 6 | (A6) 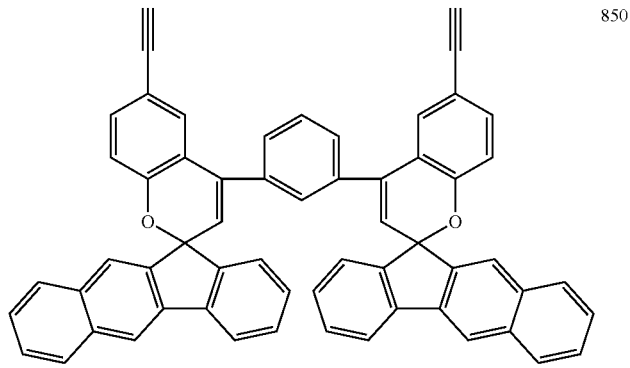 | 850 | 1.05 |

TABLE 2-continued
| Synthesis Example | Product | Mw | Mw/Mn |
|---|---|---|---|
| 7 | 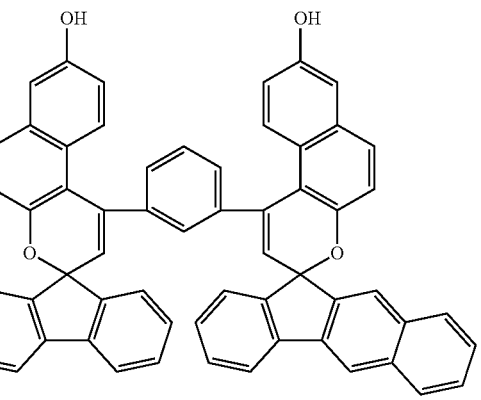 (A7) | 950 | 1.07 |
| 8 | 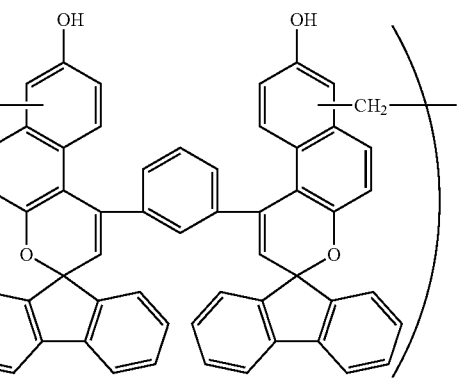 (A8) | 3300 | 1.68 |
TABLE 3
| Synthesis Example | Product | Mw | Mw/Mn |
|---|---|---|---|
| 9 | 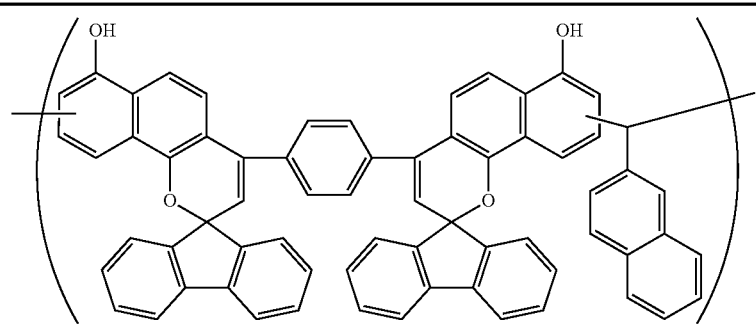 (A9) | 3400 | 1.76 |

TABLE 3-continued

| Synthesis Example | Product | Mw | Mw/Mn |
|---|---|---|---|
| 10 | (A10) | 4300 | 1.86 |
| 11 | (A11) | 3700 | 1.73 |
| 12 | (A12) | 3800 | 1.85 |

TABLE 4

| Synthesis Example | Product | Mw | Mw/Mn |
|---|---|---|---|
| 13 | 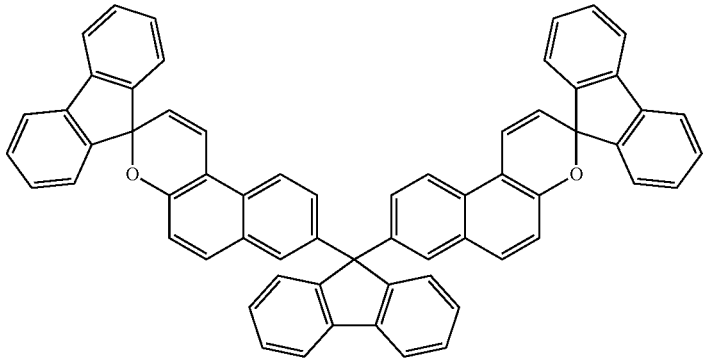 (R1) | 900 | 1.04 |
| 14 | 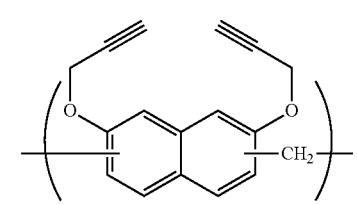 (R2) | 2900 | 1.57 |

Preparation of Materials (UDL-1 to -16, Comparative UDL-1 to -2) for forming Organic Film According to proportions shown in Table 5, Compounds and/or Polymers (A1) to (A12), (R1), and (R2) were dissolved using propylene glycol monomethyl ether acetate (PGMEA) containing 0.1 mass % PF-6320 (manufactured by OMNOVA Solutions Inc.) and optionally a high-boiling-point solvent of (S1) 1,6-diacetoxyhexane: boiling point of 260° C. or (S2) tripropylene glycol monomethyl ether: boiling point of 242° C. The resulting solutions were filtered through a 0.1-μm filter made of a fluorinated resin. Thus, materials (UDL-1 to -16, Comparative UDL-1 to -2) for forming an organic film were prepared.

TABLE 5

| Material for forming organic film | Polymer or compound (parts by mass) | High-boiling-point solvent (parts by mass) | PGMEA (parts by mass) |
|---|---|---|---|
| UDL-1 | A1 (10) | — | 90 |
| UDL-2 | A3 (10) | — | 90 |
| UDL-3 | A4 (10) | — | 90 |
| UDL-4 | A6 (10) | — | 90 |
| UDL-5 | A8 (10) | — | 90 |
| UDL-6 | A9 (10) | — | 90 |
| UDL-7 | A10 (10) | — | 90 |
| UDL-8 | A11 (10) | — | 90 |
| UDL-9 | A12 (10) | — | 90 |
| UDL-10 | A2 (3) A8 (7) | — | 90 |
| UDL-11 | A5 (3) A9 (7) | — | 90 |
| UDL-12 | A7 (5) A10 (5) | — | 90 |
| UDL-13 | A3 (10) | S1 (10) | 80 |
| UDL-14 | A4 (10) | S2 (10) | 80 |
| UDL-15 | A8 (10) | S1 (10) | 80 |
| UDL-16 | A11 (10) | S2 (10) | 80 |
| Comparative UDL-1 | R1 (10) | — | 90 |
| Comparative UDL-2 | R2 (10) | — | 90 |

Example 1: Solvent Resistance Measurement (Examples 1-1 to 1-16, Comparative Examples 1-1 to 1-2)

UDL-1 to -16 and Comparative UDL-1 to -2 prepared above were respectively applied onto silicon substrates, and baked in the atmosphere at 350° C. for 60 seconds. Then, the film thicknesses were measured. A PGMEA solvent was dispensed on each film and allowed to stand for 30 seconds. The resultant was spin dried and baked at 100° C. for 60 seconds to evaporate the PGMEA. The film thickness was measured to find the film thicknesses before and after the PGMEA treatment. The film thickness after the film formation and the film thickness after the PGMEA treatment were used to determine a film remaining ratio. Table 6 shows the result.

TABLE 6

| | Material for forming organic film | Film thickness after film formation: a (Å) | Film thickness after PGMEA treatment: b (Å) | b/a x 100 (%) |
|---|---|---|---|---|
| Example 1-1 | UDL-1 | 1992 | 1987 | 99.7 |
| Example 1-2 | UDL-2 | 1998 | 1996 | 99.9 |
| Example 1-3 | UDL-3 | 1998 | 1996 | 99.9 |
| Example 1-4 | UDL-4 | 1993 | 1990 | 99.8 |
| Example 1-5 | UDL-5 | 1995 | 1992 | 99.8 |
| Example 1-6 | UDL-6 | 2005 | 2003 | 99.9 |
| Example 1-7 | UDL-7 | 2000 | 1999 | 100.0 |
| Example 1-8 | UDL-8 | 2004 | 2003 | 100.0 |
| Example 1-9 | UDL-9 | 1998 | 1998 | 100.0 |
| Example 1-10 | UDL-10 | 1993 | 1992 | 99.9 |
| Example 1-11 | UDL-11 | 1995 | 1993 | 99.9 |
| Example 1-12 | UDL-12 | 1998 | 1997 | 99.9 |
| Example 1-13 | UDL-13 | 2004 | 2001 | 99.9 |
| Example 1-14 | UDL-14 | 1997 | 1995 | 99.9 |
| Example 1-15 | UDL-15 | 2005 | 2003 | 99.9 |
| Example 1-16 | UDL-16 | 2000 | 1999 | 100.0 |
| Comparative Example 1-1 | Comparative UDL-1 | 1990 | 1978 | 99.4 |
| Comparative Example 1-2 | Comparative UDL-2 | 1998 | 1996 | 99.9 |

As shown in Table 6, the organic films (Examples 1-1 to 1-16) obtained by using the inventive compounds and/or polymers had a film remaining ratio of 99.5% or more after the PGMEA treatment. This indicates that the crosslinking reaction took place by heating and sufficient solvent resistance was exhibited. Particularly, in comparison between Examples 1-1 to 1-4, 1-13, 1-14 and Comparative Example 1-1, which are all monomer compounds, the compound of Comparative Example 1-1 had crosslinkable moieties only at the benzopyran rings; in contrast, crosslinkable moieties of the inventive compounds were present also as the substituents at the terminals. Hence, the film thicknesses were reduced less in Examples 1-1 to 1-4, 1-13, 1-14. This indicates that the curing by heating proceeded efficiently.

Example 2: Heat Resistance Evaluation (Examples 2-1 to 2-16, Comparative Examples 2-1 to 2-2)

The materials (UDL-1 to -16, Comparative UDL-1 to -2) for forming an organic film were respectively applied onto silicon substrates, and baked in the atmosphere at 350° C. for 60 seconds. Thus, 200-nm coating films were formed, and each film thickness A was measured. The substrate was further baked at 450° C. for another 10 minutes under a nitrogen stream with the oxygen concentration being controlled to 0.2% or less. The resulting film thickness B was measured. Table 7 shows these results.

TABLE 7

| | Material for forming organic film | Film thickness at 350° C. A(Å) | Film thickness at 450° C. B(Å) | Film remaining ratio: % (B/A) |
|---|---|---|---|---|
| Example 2-1 | UDL-1 | 2000 | 1924 | 96.2 |
| Example 2-2 | UDL-2 | 2001 | 1988 | 99.4 |
| Example 2-3 | UDL-3 | 2002 | 1998 | 99.8 |
| Example 2-4 | UDL-4 | 1993 | 1987 | 99.7 |
| Example 2-5 | UDL-5 | 2002 | 1988 | 99.3 |
| Example 2-6 | UDL-6 | 1991 | 1988 | 99.8 |
| Example 2-7 | UDL-7 | 1996 | 1993 | 99.8 |
| Example 2-8 | UDL-8 | 2003 | 1987 | 99.2 |
| Example 2-9 | UDL-9 | 1994 | 1982 | 99.4 |
| Example 2-10 | UDL-10 | 1994 | 1988 | 99.7 |
| Example 2-11 | UDL-11 | 2002 | 1982 | 99.0 |
| Example 2-12 | UDL-12 | 2000 | 1980 | 99.0 |
| Example 2-13 | UDL-13 | 1998 | 1994 | 99.8 |
| Example 2-14 | UDL-14 | 2000 | 1985 | 99.3 |
| Example 2-15 | UDL-15 | 1991 | 1986 | 99.7 |
| Example 2-16 | UDL-16 | 1994 | 1993 | 99.9 |
| Comparative Example 2-1 | Comparative UDL-1 | 1993 | 1776 | 89.1 |
| Comparative Example 2-2 | Comparative UDL-2 | 1994 | 1567 | 78.6 |

As shown in Table 7, the film thicknesses of the inventive materials (Examples 2-1 to 2-16) for forming an organic film were reduced by less than 5% even after the baking at 450° C. It is understood that the film thicknesses before the high-temperature baking were maintained even after the 450° C. baking, and the inventive materials for forming an organic film were excellent in heat resistance. Particularly, in Examples 2-2 to 2-16, in which not an alkyl group but an aromatic ring structure was introduced as a linking group, the film remaining ratio was kept at 99% or more. This indicates that the heat resistance is improved. Meanwhile, Comparative Example 2-1 resulted in poor heat resistance due to insufficient crosslinking density in comparison with Examples 2-1 to 2-16, as expected from the result of Example 1. In Comparative Example 2-2, the film had sufficient curability as in the result of Example 1, but the polymer had poor heat resistance due to low rigidity of the partial structure constituting the repeating unit.

Example 3: Hardness Measurement (Examples 3-1 to 3-16, Comparative Examples 3-1 to 3-2)

UDL-1 to -16 and Comparative UDL-1 to -2 prepared above were respectively applied onto silicon substrates, and baked in the atmosphere at 350° C. for 60 seconds. Thus, coating films each having a film thickness of 200 nm were formed. These films were subjected to a nano-indentation test with a SA2 nanoindenter instrument manufactured by TOYO Corporation, and the hardness of each coating film was measured. Table 8 shows the result.

TABLE 8

| | Material for forming organic film | Hardness (GPa) |
|---|---|---|
| Example 3-1 | UDL-1 | 0.65 |
| Example 3-2 | UDL-2 | 0.62 |
| Example 3-3 | UDL-3 | 0.71 |
| Example 3-4 | UDL-4 | 0.72 |
| Example 3-5 | UDL-5 | 0.69 |
| Example 3-6 | UDL-6 | 0.65 |
| Example 3-7 | UDL-7 | 0.63 |
| Example 3-8 | UDL-8 | 0.61 |
| Example 3-9 | UDL-9 | 0.61 |
| Example 3-10 | UDL-10 | 0.69 |
| Example 3-11 | UDL-11 | 0.68 |
| Example 3-12 | UDL-12 | 0.66 |
| Example 3-13 | UDL-13 | 0.63 |
| Example 3-14 | UDL-14 | 0.70 |
| Example 3-15 | UDL-15 | 0.68 |

TABLE 8-continued

| | Material for forming organic film | Hardness (GPa) |
|---|---|---|
| Example 3-16 | UDL-16 | 0.61 |
| Comparative Example 3-1 | Comparative UDL-1 | 0.54 |
| Comparative Example 3-2 | Comparative UDL-2 | 0.63 |

As shown in Table 8, films having a hardness of 0.6 or more were formed in Examples 3-1 to 3-16. This verified that finer and stronger films than that in Comparative Example 3-1 were surely formed. This result is suggested from the result in Example 1. Meanwhile, in Comparative Example 3-2, since the curability is sufficient as in the result of Example 1, the film had a hardness of 0.6 or more, although the heat resistance was low as indicated by the result of Example 2.

Example 4: Etching Test (Examples 4-1 to 4-16, Comparative Examples 4-1 to 4-2)

[Etching Test with $CF_4/CHF_3$-based Gas]

UDL-1 to -16 and Comparative UDL-1 to -2 prepared above were respectively applied onto silicon substrates, and baked in the atmosphere at 350° C. for 60 seconds to form organic films each having a film thickness of 200 nm. Then, an etching test was conducted with $CF_4/CHF_3$-based gases under the following conditions. In this case, a dry etching apparatus TE-8500 manufactured by Tokyo Electron Limited was used. The film thickness difference of each polymer film between before and after the etching was found to calculate an etching rate (nm/min.). Table 9 shows the result.

The etching conditions were as follows.

| Chamber pressure | 40.0 Pa |
|---|---|
| RF power | 1,000 W |
| $CHF_3$ gas flow rate | 10 ml/min |
| $CF_4$ gas flow rate | 100 ml/min |
| He gas flow rate | 200 ml/min |
| Time | 20 sec |

[Etching Test with $O_2$-Based Gas]

As in the above case, UDL-1 to -16 and Comparative UDL-1 to -2 were respectively applied onto silicon substrates, and baked in the atmosphere at 350° C. for 60 seconds to form organic films each having a film thickness of 200 nm. Then, an etching test was conducted with $O_2$-based gas under the following conditions. In this case, a dry etching apparatus TE-8500 manufactured by Tokyo Electron Limited was used, and the film thickness difference of each polymer film between before and after the etching was found to calculate an etching rate (nm/min.). Table 9 shows the result together with the result of the $CF_4/CHF_3$-based gas.

The etching conditions were as follows.

| Chamber pressure | 40.0 Pa |
|---|---|
| RF power | 100 W |
| $O_2$ gas flow rate | 30 ml/min |
| $N_2$ gas flow rate | 70 ml/min |
| Time | 60 sec |

In the etching tests with $CF_4/CHF_3$-based gas and $O_2$-based gas, the lower the etching rate, the more excellent the etching resistance of the film.

TABLE 9

| | Material for forming organic film | $CF_4/CHF_3$—based gas Etching rate (nm/min.) | $O_2$-based gas Etching rate (nm/min.) |
|---|---|---|---|
| Example 4-1 | UDL-1 | 99 | 224 |
| Example 4-2 | UDL-2 | 94 | 218 |
| Example 4-3 | UDL-3 | 93 | 215 |
| Example 4-4 | UDL-4 | 88 | 210 |
| Example 4-5 | UDL-5 | 93 | 216 |
| Example 4-6 | UDL-6 | 90 | 211 |
| Example 4-7 | UDL-7 | 86 | 207 |
| Example 4-8 | UDL-8 | 90 | 214 |
| Example 4-9 | UDL-9 | 89 | 210 |
| Example 4-10 | UDL-10 | 94 | 217 |
| Example 4-11 | UDL-11 | 92 | 214 |
| Example 4-12 | UDL-12 | 90 | 213 |
| Example 4-13 | UDL-13 | 93 | 218 |
| Example 4-14 | UDL-14 | 93 | 216 |
| Example 4-15 | UDL-15 | 94 | 216 |
| Example 4-16 | UDL-16 | 91 | 213 |
| Comparative Example 4-1 | Comparative UDL-1 | 101 | 228 |
| Comparative Example 4-2 | Comparative UDL-2 | 121 | 239 |

As shown in Table 9, the comparison between Examples 4-1 to 4-16 and Comparative Examples 4-1 to 4-2 shows that in both the etching tests with $CF_4/CHF_3$-based gas and $O_2$-based gas, the etching rates in Examples were lower than those in Comparative Examples. This indicates that films excellent in etching resistance were formed in Examples.

Example 5: Pattern Etching Test (Examples 5-1 to 5-16, Comparative Examples 5-1 to 5-2)

UDL-1 to -16 and Comparative UDL-1 to -2 prepared above were respectively applied onto Si wafer substrates. Each of the Si wafer substrates had a diameter of 300 mm, and a $SiO_2$ film having a film thickness of 200 nm had been formed thereon. Then, the resultant was baked in the atmosphere at 350° C. for 60 seconds to thus form an organic film having a film thickness of 200 nm. A silicon-containing resist underlayer film material (SOG-1) was applied thereon and baked at 220° C. for 60 seconds to form a silicon-containing resist underlayer film having a film thickness of 35 nm. A resist upper layer film material (SL resist for ArF) was applied thereon and baked at 105° C. for 60 seconds to form a resist upper layer film having a film thickness of 100 nm. A liquid immersion top coat material (TC-1) was applied on the resist upper layer film and baked at 90° C. for 60 seconds to form a top coat having a film thickness of 50 nm.

The resist upper layer film material (SL resist for ArF) was prepared by: dissolving a polymer (RP1), an acid generator (PAG1), and a basic compound (Amine1) in a solvent containing 0.1 mass % FC-430 (manufactured by Sumitomo 3M Ltd.) according to proportions in Table 10; and filtering the solution through a 0.1-μm filter made of a fluorinated resin.

TABLE 10

| | Polymer (parts by mass) | Acid generator (parts by mass) | Basic compound (parts by mass) | Solvent (parts by mass) |
|---|---|---|---|---|
| SL resist for ArF | RP1 (100) | PAG1 (6.6) | Amine1 (0.8) | PGMEA (2500) |

The structural formulae of the polymer (RP1), acid generator (PAG1), and basic compound (Amine1) thus used are shown below.

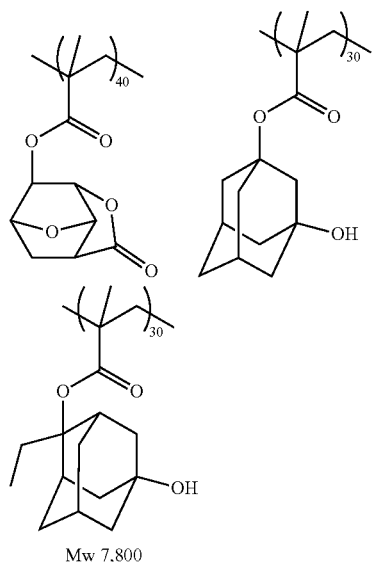

RP1

Mw 7,800

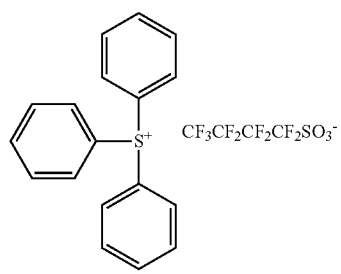

PAG1

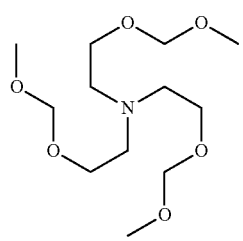

Amine1

The liquid immersion top coat material (TC-1) was prepared by dissolving: a top coat polymer (PP1) in organic solvents according to proportions in Table 11; and filtering the solution through a 0.1-μm filter made of a fluorinated resin.

TABLE 11

| | Polymer (parts by mass) | Organic solvent (parts by mass) |
|---|---|---|
| TC-1 | PP1 (100) | diisoamyl ether (2700) 2-methyl-1-butanol (270) |

The structural formula of the polymer (PP1) thus used is shown below.

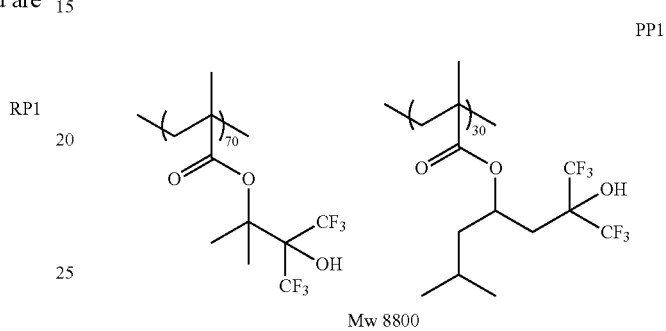

PP1

Mw 8800

The silicon-containing resist underlayer film material (SOG-1) was prepared by: dissolving a polymer represented by an ArF silicon-containing middle layer film polymer (SiP1) and a crosslinking catalyst (CAT1) in an organic solvent containing 0.1 mass % FC-4430 (manufactured by Sumitomo 3M Ltd.) according to proportions shown in Table 12; and filtering the solution through a filter having a pore size of 0.1 μm and made of a fluorinated resin.

TABLE 12

| | Polymer (parts by mass) | Thermal crosslinking catalyst (parts by mass) | Organic solvent (parts by mass) |
|---|---|---|---|
| SOG-1 | SiP1 (100) | CAT1 (1) | propylene glycol monoethyl ether (4000) |

The structural formulae of the ArF silicon-containing middle layer film polymer (SiP1) and crosslinking catalyst (CAT1) thus used are shown below.

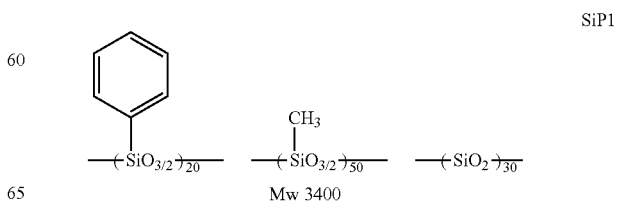

SiP1

Mw 3400

-continued

CAT1

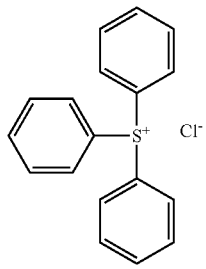

Next, the resulting substrate was exposed to light at various exposure levels with an ArF liquid immersion exposure apparatus (NSR-S610C manufactured by Nikon Corporation, NA: 1.30, σ: 0.98/0.65, 35° s-polarized dipole illumination, 6% halftone phase shift mask), baked (PEB) at 100° C. for 60 seconds, and developed with a 2.38 mass % tetramethylammonium hydroxide (TMAH) aqueous solution for 30 seconds. Thus, a positive line and space pattern was obtained with the pitch of 100 nm and the resist line width ranging from 50 nm to 30 nm.

Next, dry-etching processing with an etching apparatus Telius manufactured by Tokyo Electron Limited was performed successively as follows. The silicon-containing resist underlayer film was processed using the resist pattern as a mask; the organic film was processed using the silicon-containing resist underlayer film as a mask; and the $SiO_2$ film was processed using the organic film as a mask. The etching conditions were as follows.

Conditions for Transferring the Resist Pattern to the SOG Film:

| Chamber pressure | 10.0 | Pa |
|---|---|---|
| RF power | 1,500 | W |
| $CF_4$ gas flow rate | 15 | sccm |
| $O_2$ gas flow rate | 75 | sccm |
| Time | 15 | sec |

Conditions for Transferring the SOG Film Pattern to the Organic Film:

| Chamber pressure | 2.0 | Pa |
|---|---|---|
| RF power | 500 | W |
| Ar gas flow rate | 75 | sccm |
| $O_2$ gas flow rate | 45 | sccm |
| Time | 120 | sec |

Conditions for Transferring the Organic Film Pattern to the $SiO_2$ Film:

| Chamber pressure | 2.0 | Pa |
|---|---|---|
| RF power | 2,200 | W |
| $C_5F_{12}$ gas flow rate | 20 | sccm |
| $C_2F_6$ gas flow rate | 10 | sccm |
| Ar gas flow rate | 300 | sccm |
| $O_2$ gas flow rate | 60 | sccm |
| Time | 90 | sec |

The pattern cross sections were observed with an electron microscope (S-4700) manufactured by Hitachi, Ltd. The profiles were compared and summarized in Table 13.

TABLE 13

| | Material for forming organic film | Pattern profile after develoment | Profile after etching for transferring to silicon-containing resist underlayer film | Profile after etching for transferring to organic film | Profile after etching for transferring to substrate | Minimum dimension (nm) without pattern twisting after etching for transferring to substrate |
|---|---|---|---|---|---|---|
| Example 5-1 | UDL-1 | vertical profile | vertical profile | vertical profile | vertical profile | 33 |
| Example 5-2 | UDL-2 | vertical profile | vertical profile | vertical profile | vertical profile | 35 |
| Example 5-3 | UDL-3 | vertical profile | vertical profile | vertical profile | vertical profile | 30 |
| Example 5-4 | UDL-4 | vertical profile | vertical profile | vertical profile | vertical profile | 30 |
| Example 5-5 | UDL-5 | vertical profile | vertical profile | vertical profile | vertical profile | 31 |
| Example 5-6 | UDL-6 | vertical profile | vertical profile | vertical profile | vertical profile | 33 |
| Example 5-7 | UDL-7 | vertical profile | vertical profile | vertical profile | vertical profile | 34 |
| Example 5-8 | UDL-8 | vertical profile | vertical profile | vertical profile | vertical profile | 35 |
| Example 5-9 | UDL-9 | vertical profile | vertical profile | vertical profile | vertical profile | 35 |
| Example 5-10 | UDL-10 | vertical profile | vertical profile | vertical profile | vertical profile | 31 |
| Example 5-11 | UDL-11 | vertical profile | vertical profile | vertical profile | vertical profile | 32 |
| Example 5-12 | UDL-12 | vertical profile | vertical profile | vertical profile | vertical profile | 33 |
| Example 5-13 | UDL-13 | vertical profile | vertical profile | vertical profile | vertical profile | 34 |
| Example 5-14 | UDL-14 | vertical profile | vertical profile | vertical profile | vertical profile | 31 |

TABLE 13-continued

|  | Material for forming organic film | Pattern profile after develoment | Profile after etching for transferring to silicon-containing resist underlayer film | Profile after etching for transferring to organic film | Profile after etching for transferring to substrate | Minimum dimension (nm) without pattern twisting after etching for transferring to substrate |
|---|---|---|---|---|---|---|
| Example 5-15 | UDL-15 | vertical profile | vertical profile | vertical profile | vertical profile | 32 |
| Example 5-16 | UDL-16 | vertical profile | vertical profile | vertical profile | vertical profile | 35 |
| Comparative Example 5-1 | Comparative UDL-1 | vertical profile | vertical profile | vertical profile | vertical profile | 40 |
| Comparative Example 5-2 | Comparative UDL-2 | vertical profile | vertical profile | vertical profile | vertical profile | 34 |

As shown from the results of the inventive materials for forming an organic film (Examples 5-1 to 5-16) in Table 13, the resist upper layer film patterns were favorably transferred to the final substrates in all the cases. This confirmed that the inventive materials for forming an organic film are suitably used as organic film materials in multilayer resist method. Meanwhile, in accordance with the resist line widths formed by the light exposure, the pattern dimension transferred to the substrate was also changed. In Comparative Example 5-1, the patterns were twisted at the line width of approximately 40 nm. In contrast, in Examples 5-1 to 5-16 using the inventive compounds and/or polymers, no twisting occurred even when the pattern dimension was 35 nm or less. This revealed that the twisting resistance was high. It is understood that as in the case of the inventive compounds and polymers, when a fine and high-strength film having a hardness exceeding 0.60 GPa is formed, high twisting resistance is obtained by using such an organic film.

Example 6: Planarizing Property Evaluation
(Examples 6-1 to 6-13, Comparative Example 6-1)

The materials (UDL-2 to -3, -5 to -8, -10 to -16, Comparative UDL-2) for forming an organic film were respectively applied onto SiO$_2$ substrates (8 in FIG. 2) each having a giant isolated trench pattern (trench width: 10 μm, trench depth: 0.10 μm), and baked in the atmosphere at 350° C. for 60 seconds. Then, a step (delta in FIG. 2) between the trench portion and the non-trench portion of the resulting organic film (7 in FIG. 2) was observed with an atomic force microscope (AFM) NX10 manufactured by Park systems Corp. Table 14 shows the result. In this evaluation, the smaller the step, the better the planarizing property. Note that, in this evaluation, a trench pattern having a depth of 0.10 μm was planarized using a material for forming an organic film to have a film thickness of approximately 0.2 μm. This is a strict evaluation condition to evaluate the planarizing property.

TABLE 14

| | Material for forming organic film | Step (nm) |
|---|---|---|
| Example 6-1 | UDL-2 | 40 |
| Example 6-2 | UDL-3 | 45 |
| Example 6-3 | UDL-5 | 75 |
| Example 6-4 | UDL-6 | 80 |
| Example 6-5 | UDL-7 | 85 |
| Example 6-6 | UDL-8 | 70 |
| Example 6-7 | UDL-10 | 60 |
| Example 6-8 | UDL-11 | 65 |
| Example 6-9 | UDL-12 | 65 |
| Example 6-10 | UDL-13 | 30 |
| Example 6-11 | UDL-14 | 40 |
| Example 6-12 | UDL-15 | 70 |
| Example 6-13 | UDL-16 | 65 |
| Comparative Example 6-1 | Comparative UDL-2 | 90 |

As shown in Table 14, the organic films obtained from the inventive materials for forming an organic film had smaller steps between the trench and non-trench portions than that in Comparative Example 6-1. This verified that the inventive materials are excellent in planarizing property. This is because the inventive polymers are excellent in heat resistance as demonstrated in Example 2, so that the film shrinkage by baking is suppressed. Moreover, the comparison between Examples 6-10 to 6-13 with the high-boiling-point solvent added and Examples 6-1 to 6-3, 6-6 without the high-boiling-point solvent shows that adding the high-boiling-point solvent improves the planarizing property. Further, the comparison between Examples 6-7 to 6-9, in which the polymer was mixed with the compound, and Examples 6-3 to 6-5, in which the polymer was alone, shows that the planarizing property was improved in the former. According to this result, the planarizing property can be improved without impairing various properties required for organic films, such solvent resistance, heat resistance, twisting resistance, and etching resistance as in the above-described results of Example 1 to Example 5.

From the above, the inventive material for forming an organic film enables heat resistance, high etching resistance, and excellent twisting resistance during etching. The inventive material is quite useful for an organic film used in multilayer resist processes, particularly three-layer resist process, for ultrafine and highly precise patterning.

The invention claimed is:
1. A material for forming an organic film, comprising:
(A) a compound shown by the following general formula (1) and/or a polymer comprising a repeating unit shown by the following general formula (4); and

(B) an organic solvent,

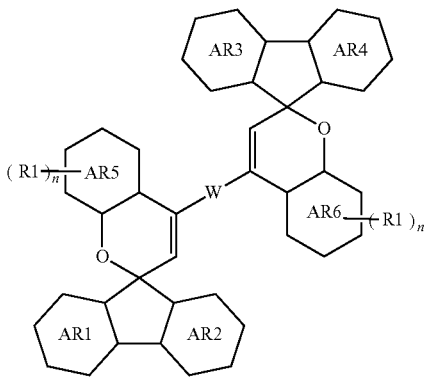

(1)

wherein AR1, AR2, AR3, AR4, AR5, and AR6 each represent a benzene ring or a naphthalene ring; R1 represents any group shown in the following formula (2); "n" represents an integer of 1 or 2; and W represents a divalent organic group having 2 to 50 carbon atoms,

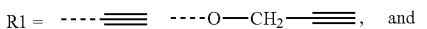

(2)

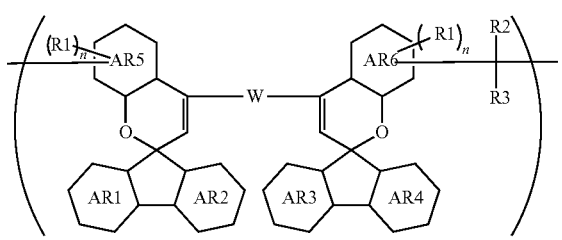

(4)

wherein AR1, AR2, AR3, AR4, AR5, AR6, R1, "n", and W are as defined above; and R2 and R3 each represent a hydrogen atom or an organic group having 1 to 20 carbon atoms, and optionally bond to each other within a molecule to form a cyclic organic group.

2. The material for forming an organic film according to claim 1, wherein
the compound is a compound shown by the following general formula (3),

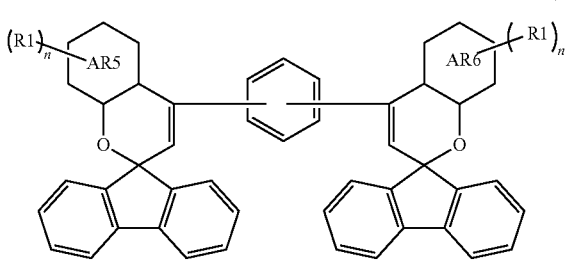

(3)

wherein AR5, AR6, R1, and "n" are as defined above.

3. The material for forming an organic film according to claim 1, wherein
the polymer is a polymer comprising a repeating unit shown by the following general formula (5),

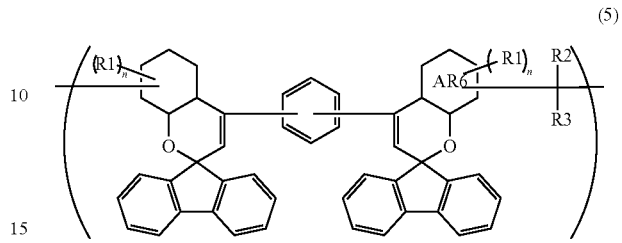

(5)

wherein AR5, AR6, R1, R2, R3, and "n" are as defined above.

4. The material for forming an organic film according to claim 2, wherein
the polymer is a polymer comprising a repeating unit shown by the following general formula (5),

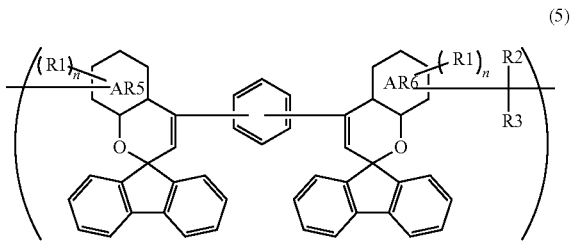

(5)

wherein AR5, AR6, R1, R2, R3, and "n" are as defined above.

5. The material for forming an organic film according to claim 1, wherein the polymer has a weight-average molecular weight of 1000 to 10000.

6. The material for forming an organic film according to claim 1, wherein the organic solvent is a mixture of one or more organic solvents each having a boiling point of lower than 180° C. and one or more organic solvents each having a boiling point of 180° C. or higher.

7. The material for forming an organic film according to claim 1, further comprising one or more of (C) an acid generator, (D) a surfactant, (E) a crosslinking agent, and (F) a plasticizer.

8. A patterning process for forming a pattern in a substrate to be processed, comprising:
   forming an organic film by using the material for forming an organic film according to claim 1 on a substrate to be processed;
   forming a silicon-containing resist underlayer film by using a silicon-containing resist underlayer film material on the organic film;
   forming a resist upper layer film by using a photoresist composition on the silicon-containing resist underlayer film;
   forming a circuit pattern in the resist upper layer film;
   transferring the pattern to the silicon-containing resist underlayer film by etching while using the resist upper layer film having the formed pattern as a mask;
   transferring the pattern to the organic film by etching while using the silicon-containing resist underlayer film having the transferred pattern as a mask; and further forming the pattern in the substrate to be processed by etching while using the organic film having the transferred pattern as a mask.

9. A patterning process for forming a pattern in a substrate to be processed, comprising:
forming an organic film by using the material for forming an organic film according to claim 1 on a substrate to be processed;
forming a silicon-containing resist underlayer film by using a silicon-containing resist underlayer film material on the organic film;
forming an organic antireflective coating film on the silicon-containing resist underlayer film;
forming a resist upper layer film by using a photoresist composition on the organic antireflective coating film, so that a 4-layered film structure is constructed;
forming a circuit pattern in the resist upper layer film;
transferring the pattern to the organic antireflective coating film and the silicon-containing resist underlayer film by etching while using the resist upper layer film having the formed pattern as a mask;
transferring the pattern to the organic film by etching while using the silicon-containing resist underlayer film having the transferred pattern as a mask; and
further forming the pattern in the substrate to be processed by etching the substrate to be processed while using the organic film having the transferred pattern as a mask.

10. A patterning process for forming a pattern in a substrate to be processed, comprising:
forming an organic film by using the material for forming an organic film according to claim 1 on a substrate to be processed;
forming an inorganic hard mask selected from a silicon oxide film, a silicon nitride film, and a silicon oxynitride film on the organic film;
forming a resist upper layer film by using a photoresist composition on the inorganic hard mask;
forming a circuit pattern in the resist upper layer film;
transferring the pattern to the inorganic hard mask by etching while using the resist upper layer film having the formed pattern as a mask;
transferring the pattern to the organic film by etching while using the inorganic hard mask having the transferred pattern as a mask; and
further forming the pattern in the substrate to be processed by etching the substrate to be processed while using the organic film having the transferred pattern as a mask.

11. A patterning process for forming a pattern in a substrate to be processed, comprising:
forming an organic film by using the material for forming an organic film according to claim 1 on a substrate to be processed;
forming an inorganic hard mask selected from a silicon oxide film, a silicon nitride film, and a silicon oxynitride film on the organic film;
forming an organic antireflective coating film on the inorganic hard mask;
forming a resist upper layer film by using a photoresist composition on the organic antireflective coating film, so that a 4-layered film structure is constructed;
forming a circuit pattern in the resist upper layer film;
transferring the pattern to the organic antireflective coating film and the inorganic hard mask by etching while using the resist upper layer film having the formed pattern as a mask;
transferring the pattern to the organic film by etching while using the inorganic hard mask having the transferred pattern as a mask; and
further forming the pattern in the substrate to be processed by etching the substrate to be processed while using the organic film having the transferred pattern as a mask.

12. The patterning process according to claim 10, wherein the inorganic hard mask is formed by a CVD method or an ALD method.

13. The patterning process according to claim 8, wherein the pattern is formed in the resist upper layer film by a method of a photolithography with a wavelength of 10 nm or more and 300 nm or less, a direct drawing with electron beam, nanoimprinting, or a combination thereof.

14. The patterning process according to claim 8, wherein alkaline development or organic solvent development is employed as a development method in the patterning process.

15. The patterning process according to claim 8, wherein the substrate to be processed is a semiconductor device substrate, a metal film, a metal carbide film, a metal oxide film, a metal nitride film, a metal oxycarbide film, or a metal oxynitride film.

16. The patterning process according to claim 15, wherein the metal is silicon, titanium, tungsten, hafnium, zirconium, chromium, germanium, cobalt, copper, silver, gold, aluminum, indium, gallium, arsenic, palladium, iron, tantalum, iridium, manganese, molybdenum, ruthenium, or an alloy thereof.

17. A compound shown by the following general formula (1),

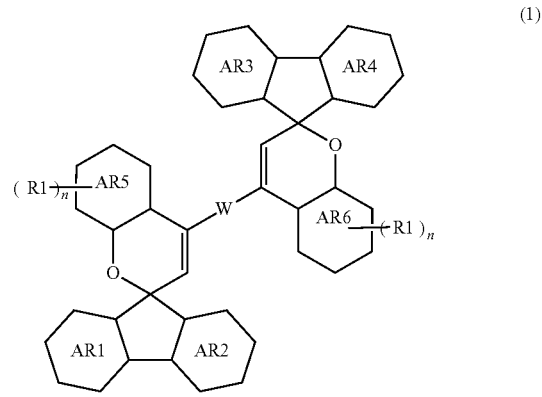

wherein AR1, AR2, AR3, AR4, AR5, and AR6 each represent a benzene ring or a naphthalene ring; R1 represents any group shown in the following formula (2); "n" represents an integer of 1 or 2; and W represents a divalent organic group having 2 to 50 carbon atoms,

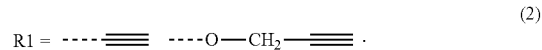

18. The compound according to claim 17, wherein the compound is shown by the following general formula (3), (3)

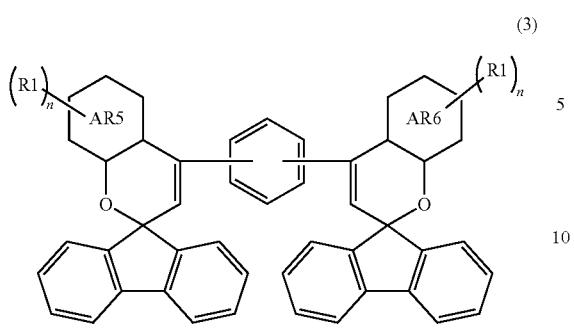

wherein AR5, AR6, R1, and "n" are as defined above.

19. A polymer comprising a repeating unit shown by the following general formula (4), (4)

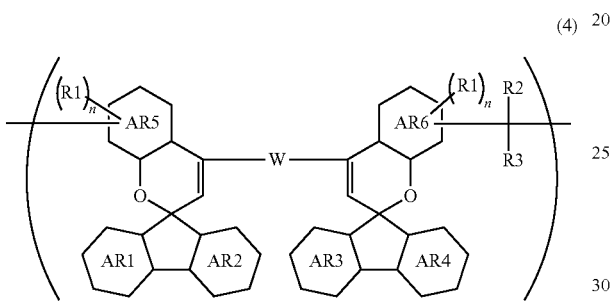

wherein AR1, AR2, AR3, AR4, AR5, and AR6 each represent a benzene ring or a naphthalene ring; R1 represents any group shown in the following formula (2); "n" represents an integer of 1 or 2; W represents a divalent organic group having 2 to 50 carbon atoms; and R2 and R3 each represent a hydrogen atom or an organic group having 1 to 20 carbon atoms, and optionally bond to each other within a molecule to form a cyclic organic group, $$R1 = \text{-----}\equiv\text{----}O\text{---}CH_2\text{---}\equiv\cdot \qquad (2)$$

20. The polymer according to claim 19, wherein the polymer comprises a repeating unit shown by the following general formula (5), (5)

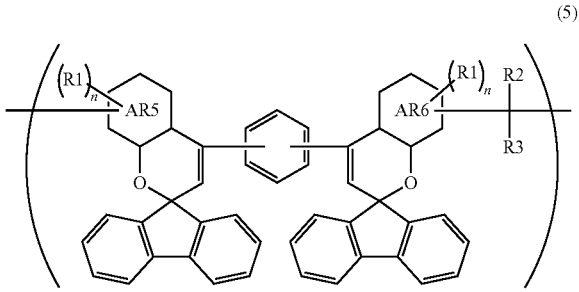

wherein AR5, AR6, R1, R2, R3, and "n" are as defined above.

* * * * *